(12) United States Patent
Kunz et al.

(10) Patent No.: US 6,380,134 B1
(45) Date of Patent: Apr. 30, 2002

(54) N-PYRIDYL HERBICIDE COMPOUNDS

(75) Inventors: Walter Kunz, Oberwil; Kurt Nebel, Hochwald; Jean Wenger, Wallbach, all of (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/685,671

(22) Filed: Oct. 10, 2000

Related U.S. Application Data

(63) Continuation of application No. PCT/EP99/02312, filed on Apr. 6, 1999.

(30) Foreign Application Priority Data

Apr. 8, 1998 (CH) ................................................ 0839/98

(51) Int. Cl.⁷ ........................ C07D 401/00; A01N 43/40
(52) U.S. Cl. ........................ 504/238; 504/243; 504/244; 504/253; 504/260; 544/238; 544/333; 546/272.4; 546/274.4; 546/305; 546/306; 546/309
(58) Field of Search ................................ 504/238, 243, 504/244, 253, 260; 546/272.4, 274.4, 309, 305, 306; 544/238, 333

(56) References Cited

U.S. PATENT DOCUMENTS 4,406,689 A * 9/1983 Anderson et al. ........... 504/253
5,306,694 A * 4/1994 Phillips et al. .............. 504/253

* cited by examiner

*Primary Examiner*—Zinna Northington Davis
(74) *Attorney, Agent, or Firm*—William A. Teoli, Jr.

(57) ABSTRACT

Compounds of the formula I

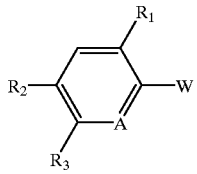
(I)

in which
A is =N— or

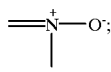

$R_1$ is hydrogen, fluorine, chlorine, bromine or methyl;
$R_2$ is $C_1$–$C_4$alkyl, $C_1$–$C_4$haloalkyl, halogen, $R_6O$—, nitro, amino or cyano;
W is a group

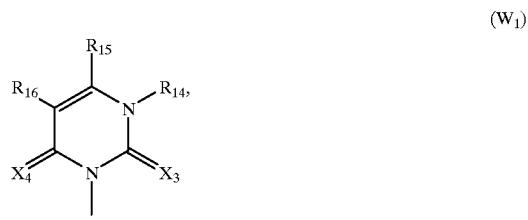
(W₁)

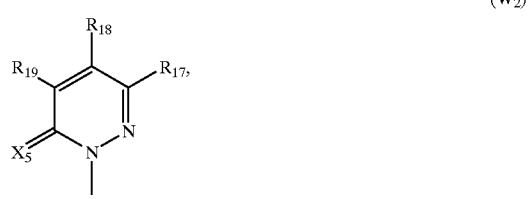

(W₂)

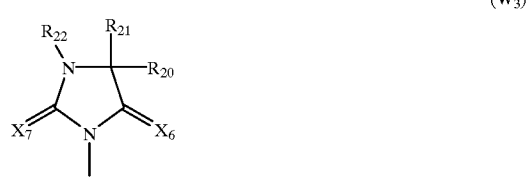

(W₃)

or

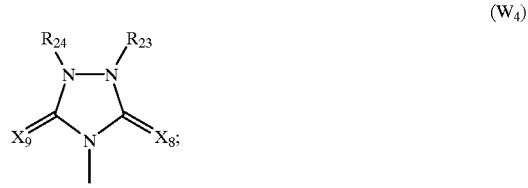
(W₄)

and
$R_3$, $R_6$, $R_{14}$ to $R_{24}$ and $X_3$ to $X_9$ have the meanings given in claim 1 and the agrochemically tolerated salts and stereoisomers of these compounds of the formula I are suitable for use as herbicides.

9 Claims, No Drawings

N-PYRIDYL HERBICIDE COMPOUNDS

This application is a Continuation of PCT/EP99/023012 filed Apr. 6, 1999.

The present invention relates to novel herbicidally active substituted N-pyridyl-nitrogen heterocycles, processes for their preparation, compositions comprising these compounds, and their use for controlling weeds, especially in crops of useful plants such as, for example, cereals, maize, rice, cotton, soya, oil seed rape, sorghum, sugar cane, sugar beet, sunflowers, vegetables, plantation crops and forage plants, or for inhibiting the growth of plants, and for nonselective weed control.

N-phenyl- and n-pyridyl-pyrazole compounds and N-pyridyltetramethylene triazolidine diones which are herbicidally active are described, for example, in EP-A-0 370 332, DE-A-3 917 469, DE-A-19 518 054, DE-A-19 530 606, U.S. Pat. No. 5,306,694 and U.S. Pat. No. 4,406,689. Also known as herbicides are N-pyridylimides, N-(2-pyridyl) pyridazinones and N-phenyluracils, as described, for example, in WO 92/00976, JP-A-58-213 776 and EP-A-0 438 209. N-(phenyl)tetrahydroimidazoles having herbicidal activity are described, for example, in U.S. Pat. No. 5,112,383.

There have now been found novel substituted N-pyridyl-nitrogen heterocycles which have herbicidal and growth-inhibitory properties.

The present invention thus relates to compounds of the formula I

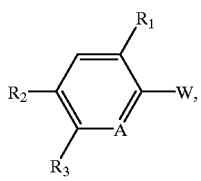

(I)

in which

A =N— or

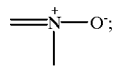

$R_1$ is hydrogen, fluorine, chlorine, bromine or methyl;

$R_2$ is $C_1$–$C_4$alkyl, $C_1$–$C_4$haloalkyl, halogen, $R_6O$—, nitro, amino or cyano;

$R_3$ is halogen, nitro, amino, $R_4NH$—, $R_4R_5N$—, azido or $ClS(O)_2$—;

$R_4$ and $R_5$ independently of one another are $C_1$–$C_8$alkyl, $C_3$–$C_8$alkenyl, $C_3$–$C_8$alkynyl, $C_3$–$C_6$cycloalkyl, $C_1$–$C_8$haloalkyl, $C_3$–$C_8$haloalkenyl, HCO—, $C_1$–$C_4$alkylcarbonyl, $C_1$–$C_4$haloalkylcarbonyl, $C_1$–$C_4$alkylsulfonyl, $C_1$–$C_4$haloalkylsulfonyl, benzyl or benzyl which is mono- to trisubstituted on the phenyl ring by halogen, $C_1$–$C_4$alkyl or $C_1$–$C_4$haloalkyl; or $R_4$ and $R_5$ together with the N atom to which they are bonded form a saturated or unsaturated heterocyclic ring which contains O, N or S as further hetero atoms and which can be substituted by halogen, $C_1$–$C_3$alkyl, $C_1$–$C_3$haloalkyl, $C_1$–$C_3$alkoxy, $C_1$–$C_4$alkoxycarbonyl, $C_1$–$C_3$alkylS(O)_{n1}$—, nitro or cyano; or $R_3$ is $R_6O$—;

$R_6$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl, cyano-$C_1$–$C_8$alkyl, $C_3$–$C_8$haloalkenyl, hydroxy-$C_1$–$C_4$alkyl, $C_1$–$C_4$alkoxy-$C_1$–$C_4$alkyl, $C_3$–$C_6$alkenyloxy-$C_1$–$C_4$alkyl, $C_3$–$C_6$alkynyloxy-$C_1$–$C_4$alkyl, $C_1$–$C_4$alkoxy-$C_1$–$C_4$alkoxy-$C_1$–$C_4$alkyl, $C_1$–$C_4$alkylthio-$C_1$–$C_4$alkyl, $C_1$–$C_8$alkylcarbonyl, $C_1$–$C_8$alkoxycarbonyl, $C_3$–$C_8$alkenyloxycarbonyl, benzyloxy-$C_1$- or —$C_2$alkyl, benzylcarbonyl, benzyloxycarbonyl, phenyl,phenyl-$C_2$–$C_8$alkyl, benzyl, pyridyl, pyrimidinyl, pyrazinyl or pyridazinyl, it being possible for these aromatic and heteroaromatic rings to be optionally mono- to trisubstituted by halogen, $C_1$–$C_4$alkyl or $C_1$–$C_4$haloalkyl; or $R_6$ is $R_7X_1C(O)$—$C_1$–$C_8$alkyl- or

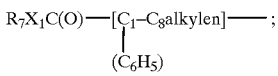

$X_1$ is oxygen, sulfur or

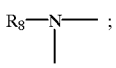

$R_7$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl, $C_3$–$C_8$haloalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is mono- to trisubstituted by halogen, $C_1$–$C_4$alkyl or $C_1$–$C_4$haloalkyl, or benzyl or benzyl which is mono- to trisubstituted on the phenyl ring by halogen, $C_1$–$C_4$alkyl or $C_1$–$C_4$haloalkyl;

$R_8$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl or benzyl; or $R_3$ is $R_9S(O)_{n1}$—;

$n_1$ is 0, 1 or 2;

$R_9$ is $C_1$–$C_8$alkyl, $C_3$–$C_8$alkenyl, $C_3$–$C_8$alkynyl, $C_3$–$C_6$cycloalkyl, $C_1$–$C_8$haloalkyl, carboxy-$C_1$–$C_4$alkyl, $C_1$–$C_4$alkoxycarbonyl-$C_1$–$C_4$alkyl, benzyloxycarbonyl-$C_1$–$C_4$alkyl, $C_1$–$C_4$alkylthio-C(O)—$C_1$–$C_4$alkyl, $C_3$–$C_5$alkenyloxycarbonyl-$C_1$–$C_4$alkyl, $C_1$–$C_4$alkylaminocarbonyl-$C_1$–$C_4$alkyl, di-$C_1$–$C_4$alkylaminocarbonyl-$C_1$–$C_4$alkyl, $C_3$–$C_5$alkenylaminocarbonyl-$C_1$–$C_4$alkyl, $C_3$–$C_8$haloalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is mono- to trisubstituted by halogen, $C_1$–$C_4$alkyl or $C_1$–$C_4$haloalkyl, or benzyl or benzyl which is mono- to trisubstituted on the phenyl ring by halogen, $C_1$–$C_4$alkyl or $C_1$–$C_4$haloalkyl, and, if $n_1$ is 0, $R_9$ is additionally hydrogen, $C_1$–$C_8$alkylcarbonyl, $R_{10}X_2C(O)$— or $R_{10}X_2C(O)$—$C_1$— or —$C_2$alkyl;

$X_2$ is oxygen, sulfur or

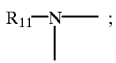

$R_{10}$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl, $C_3$–$C_8$haloalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is mono- to trisubstituted by halogen, $C_1$–$C_4$alkyl or $C_1$–$C_4$haloalkyl, or benzyl or benzyl which is mono- to trisubstituted on the phenyl ring by halogen, $C_1$–$C_4$alkyl or $C_1$–$C_4$haloalkyl;

$R_{11}$ is hydrogen, $C_1$–$C_8$alkyl or $C_3$–$C_8$alkenyl; or $R_3$ is $R_{12}R_{13}NS(O)_2$—;

$R_{12}$ is hydrogen, $C_1$–$C_8$alkyl, $C_2$–$C_8$alkenyl, $C_3$–$C_8$alkynyl or $C_3$–$C_6$cycloalkyl;

$R_{13}$ is hydrogen, $C_1$–$C_8$alkyl, $C_3$–$C_8$alkenyl, $C_3$–$C_8$alkynyl, $C_1$–$C_8$haloalkyl, $C_1$–$C_4$alkoxy-$C_1$–$C_4$alkyl, $C_1$–$C_4$alkylcarbonyl, $C_1$–$C_4$haloalkylcarbonyl, benzyl, benzoyl, or benzyl or benzoyl which are mono- to trisubstituted on the phenyl ring by halogen, $C_1$–$C_4$alkyl or $C_1$–$C_4$haloalkyl;

W is a group

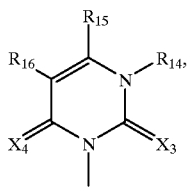

(W₁)

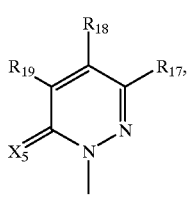

(W₂)

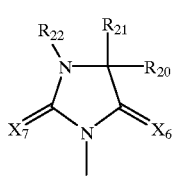

(W₃)

or

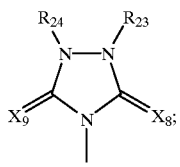

(W₄)

$R_{14}$ is $C_1$–$C_3$alkyl, $C_1$–$C_3$haloalkyl or amino;

$R_{15}$ is $C_1$–$C_3$haloalkyl, $C_1$–$C_3$alkyl-$S(O)_{n2}$—, $C_1$–$C_3$haloalkyl-$S(O)_{n2}$— or cyano; or $R_{15}$ and $R_{14}$ together form a $C_3$ or $C_4$alkylene bridge which can be substituted by halogen, $C_1$–$C_3$haloalkyl or cyano;

$n_2$ is 0, 1 or 2;

$R_{16}$ is hydrogen, $C_1$–$C_3$alkyl, halogen, $C_1$–$C_3$haloalkyl or cyano; or $R_{16}$ and $R_{15}$ together form a $C_3$ or $C_4$alkylene bridge which can be substituted by halogen, $C_1$–$C_3$haloalkyl or cyano;

$R_{17}$ is hydrogen, $C_1$–$C_3$alkyl, halogen or cyano; $R_{18}$ is $C_1$–$C_3$haloalkyl; or $R_{18}$ and $R_{17}$ together form a $C_3$ or $C_4$alkylene or $C_3$ or $C_4$alkenylene bridge, both of which can be substituted by halogen, $C_1$–$C_3$alkyl or $C_1$–$C_3$haloalkyl;

$R_{19}$ is hydrogen, $C_1$–$C_3$alkyl or halogen; or $R_{19}$ and $R_{18}$ together form a $C_3$ or $C_4$alkylene or $C_3$ or $C_4$alkenylene bridge, both of which can be substituted by halogen, $C_1$–$C_3$alkyl or $C_1$–$C_3$haloalkyl;

$R_{20}$ and $R_{21}$ independently of one another are hydrogen or $C_1$–$C_4$alkyl; or $R_{20}$ and $R_{21}$ together are a group of

;

$R_{25}$ and $R_{26}$ independently of one another are $C_1$–$C_4$alkyl; or $R_{25}$ and $R_{26}$ together form a $C_4$ or $C_5$alkylene bridge;

$R_{22}$ is hydrogen or $C_1$–$C_3$alkyl; or $R_{22}$ and $R_{21}$ together form a $C_3$–$C_5$alkylene bridge which can be interrupted by oxygen and substituted by halogen, $C_1$–$C_4$alkyl, $C_1$–$C_3$haloalkyl, $C_2$–$C_4$alkenyl, $C_1$–$C_3$alkylcarbonyloxy, $C_1$–$C_3$alkoxycarbonyl, $C_1$–$C_3$alkylsulfonyloxy, hydroxyl or =O;

$R_{23}$ and $R_{24}$ independently of one another are hydrogen or $C_1$–$C_3$alkyl; or $R_{23}$ and $R_{24}$ together form a $C_2$–$C_5$alkylene bridge which can be interrupted by oxygen, sulfur, —C(O)— or —$S(O)_2$—; and $X_3$, $X_4$, $X_5$, $X_6$, $X_7$, $X_8$ and $X_9$ independently of one another are oxygen or sulfur, and the agrochemically tolerated salts and stereoisomers of these compounds of the formula I.

In the abovementioned definitions, halogen is to be understood as meaning iodine, preferably fluorine, chlorine and bromine.

The alkyl, alkenyl and alkynyl groups in the definitions of substituents can be straight-chain or branched, and this also applies to the alkyl, alkenyl and alkynyl moiety of the alkylcarbonyl, alkylcarbonyloxy, alkoxycarbonyl, alkenyloxycarbonyl, alkenyloxyalkyl, alkynyloxyalkyl-, $alkylS(O)_{n2}$—, alkylsulfonyloxy, alkylthioalkyl, alkoxyalkyl, alkoxyalkoxyalkyl, alkylamino, dialkylamino, phenylalkyl and $R_7X_1C(O)$—$C_1$–$C_8$alkyl groups. Alkyl groups, are, for example, methyl, ethyl, n-propyl, iso-propyl, n-butyl, sec-butyl, iso-butyl, tert-butyl and the various isomeric pentyl, hexyl, heptyl and octyl radicals. Preferred are methyl, ethyl, n-propyl, iso-propyl and n-butyl.

Examples which may be mentioned of alkenyls are vinyl, allyl, methallyl, 1-methylvinyl, but-2-en-1-yl, pentenyl, 2-hexenyl, 3-heptenyl and 4-octenyl, preferably alkenyl radicals having a chain length of 3 to 5 carbon atoms.

Examples of alkynyls which may be mentioned are propargyl, 1-methylpropargyl, 3-butinyl, but-2-yn-1-yl, 2-methylbutin-2-yl, but-3-yn-2-yl, 1-pentinyl, pent-4-yn-1-yl, 2-hexinyl, 3-heptin-1-yl and 4-octin-1-yl, preferably alkynyl radicals having a chain length of 3 or 4 carbon atoms.

Suitable as haloalkyl are alkyl groups which are mono- or polysubstituted, in particular mono- to trisubstituted, by halogen, halogen being specifically iodine and in particular fluorine, chlorine and bromine, for example fluoromethyl, difluoromethyl, trifluoromethyl, chloromethyl, dichloromethyl, trichloromethyl, 2-fluoroethyl, 2,2-difluoroethyl, 2-chloroethyl, 2,2-dichloroethyl, 2,2,2-trifluoroethyl, 2,2,2-trichloroethyl and pentafluoroethyl.

Suitable as haloalkenyl are alkenyl groups which are mono- or polysubstituted by halogen, halogen being specifically bromine, iodine and in particular fluorine and chlorine, for example 2- and 3-fluoropropenyl, 2- and 3-chloropropenyl, 2- and 3-bromopropenyl, 2,3,3-trifluoropropenyl, 2,3,3-trichloropropenyl, 4,4,4-trifluorobut-2-en-1-yl and 4,4,4-trichlorobut-2-en-1-yl. Preferred amongst the alkenyl radicals which are mono-, di- or trisubstituted by halogen are those which have a chain length of 3 or 4 carbon atoms. The alkenyl groups can be substituted by halogen on saturated or unsaturated carbon atoms.

Alkylsulfonyl is, for example, methylsulfonyl, ethylsulfonyl, propylsulfonyl, iso-propylsulfonyl, n-butylsulfonyl, iso-butylsulfonyl, sec-butylsulfonyl, tert-butylsulfonyl; preferably methylsulfonyl and ethylsulfonyl.

Haloalkylsulfonyl is, for example, fluoromethylsulfonyl, difluoromethylsulfonyl, trifluoromethylsulfonyl, chloromethylsulfonyl, trichloromethylsulfonyl, 2-fluoroethylsulfonyl, 2,2,2-trifluoroethylsulfonyl and 2,2,2-trichloroethylsulfonyl.

Haloalkenylsulfonyl is, for example, 2- and 3-fluoropropenylsulfonyl, 2- and 3-chloropropenylsulfonyl, 2- and 3-bromopropenylsulfonyl, 2,3,3-trifluoropropenylsulfonyl, 2,3,3-trichloropropenylsulfonyl, 4,4,4-trifluoro-but-2-en-1-yl-sulfonyl and 4,4,4-trichlorobut-2-en-1-yl-sulfonyl.

Alkylcarbonyl is, in particular, acetyl and propionyl.

Haloalkylcarbonyl is, in particular, trifluoroacetyl, trichloroacetyl, 3,3,3-trifluoropropionyl and 3,3,3-trichloropropionyl.

Cyanoalkyl is, for example, cyanomethyl, cyanoethyl, cyanoeth-1-yl and cyanopropyl.

Hydroxyalkyl is, for example, 2-hydroxyethyl, 3-hydroxypropyl and 2,3-dihydroxypropyl.

Alkoxyalkyl is, for example, methoxymethyl, methoxyethyl, ethoxymethyl, ethoxyethyl, n-propoxymethyl, n-propoxyethyl, iso-propoxymethyl and iso-propoxyethyl.

Alkenyloxyalkyl is, for example, allyloxyalkyl, methallyloxyalkyl and but-2-en-1-yl-oxyalkyl.

Alkynyloxyalkyl is, for example, propargyloxyalkyl and 1-methylpropargyloxyalkyl.

Alkoxycarbonyl is, for example, methoxycarbonyl, ethoxycarbonyl, n-propoxycarbonyl, iso-propoxycarbonyl and n-butoxycarbonyl, preferably methoxycarbonyl and ethoxycarbonyl.

Alkenyloxycarbonyl is, for example, allyloxycarbonyl, methallyloxycarbonyl, but-2-en-1-yl-oxycarbonyl, pentenyloxycarbonyl and 2-hexenyloxycarbonyl.

The cycloalkyl radicals which are suitable as substituents are, for example, cyclopropyl, cyclobutyl, cyclopentyl and cyclohexyl.

Alkylthio is, for example, methylthio, ethylthio, propylthio and iso-propylthio.

Alkylthioalkyl is, for example, methylthioethyl, ethylthioethyl, methylthiopropyl and ethylthiopropyl.

L in the reagents of the formulae V, VII, XXI, XXX, XXXIIIa and XXXIIIb in reaction schemes 1, 2, 4, 6 and 7 is a leaving group such as, for example, halogen, for example chlorine, bromine or iodine, or sulfate, for example $CH_3S(O)_2O—$ or

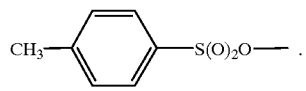

$L_1$ in the reagent of the formula XXII (reaction scheme 4) is a leaving group such as, for example, $HOS(O)_2O—$,

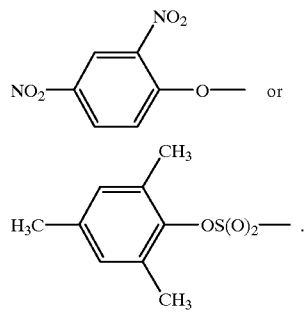

$R_4$ and $R_5$ together with the N atom to which they are bonded form a saturated or unsaturated heterocyclic ring which can contain O, N or S as further heteroatoms, for example the following heterocycles:

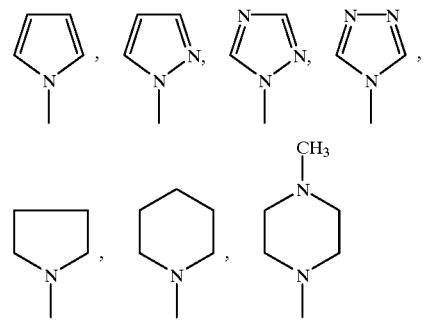

and

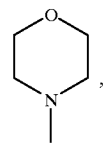

it being possible for these heterocycles additionally to be substituted by halogen, $C_1$–$C_3$alkyl, $C_1$–$C_3$haloalkyl, $C_1$–$C_3$alkoxy, $C_1$–$C_4$alkoxycarbonyl, $C_1$–$C_3$alkylS(O)$_{n1}$—, nitro or cyano.

Corresponding meanings may also be assigned to the substituents in composite definitions such as, for example, alkenyloxycarbonylalkyl, alkenylaminocarbonylalkyl, alkylthio-C(O)-alkyl, haloalkylS(O)$_{n2}$, $R_4$NH—, $R_4R_5$N—, $R_{10}X_2C(O)$—, $R_6O$—, $R_9S(O)_{n1}$—, $R_{10}X_2C(O)$—, $R_{10}X_2C(O)$—$C_1$ or -$C_2$alkyl and $R_{12}R_{13}NS(O)_2$—.

In the definition of $R_6$, the group

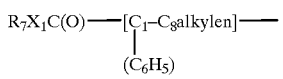

means that the $R_7X_1C(O)$-substituted $C_1$–$C_8$alkylene chain is additionally phenyl-substituted on one of the 8 carbon atoms, it being possible for the phenyl ring to be mono- to trisubstituted by halogen, $C_1$–$C_4$alkyl or $C_1$–$C_4$haloalkyl and for the alkylene chain to be straight-chain or branched, for example methylene, ethylene, methylethylene, propylene, 1-methylpropylene and butylene.

In the definitions cyanoalkyl, carboxyalkyl, alkylcarbonyl, alkylcarbonyloxy, alkoxycarbonyl, alkenyloxycarbonyl and haloalkylcarbonyl, the carbonyl carbon atom is not included in the lower and upper limits of carbon atoms given in each case.

The invention also extends to the salts which the compounds of the formula I which have an acidic hydrogen, in particular the derivatives having carboxyl and sulfonamide groups (for example carboxyl-substituted alkyl and alkylene groups ($R_6$), alkylS(O)$_2$NH— and haloalkylS(O)$_2$NH— substituted pyridyl groups ($R_3$)), can form with bases. These salts are, for example, alkali metal salts such as, for example, sodium salts and potassium salts; alkaline earth metal salts such as, for example, calcium salts and magnesium salts; ammonium salts, i.e. unsubstituted ammonium salts and mono- or polysubstituted ammonium salts such as, for example, triethylammonium salts and methylammonium salts; or salts with other organic bases.

Amongst the alkali metal hydroxides and alkaline earth metal hydroxides, examples of salt formers which must be emphasized are the hydroxides of lithium, sodium, potassium, magnesium or calcium, but in particular those of sodium and potassium. Suitable salt formers are described, for example, in WO 97/41112.

Possible examples for amines which are suitable for ammonium salt formation are ammonia and also primary, secondary and tertiary $C_1$–$C_{18}$alkylamines, $C_1$–$C_4$hydroxyalkylamines and $C_2$–$C_4$alkoxyalkylamines, for example methylamine, ethylamine, n-propylamine, iso-propylamine, the four butylamine isomers, n-amylamine, iso-amylamine, hexylamine, heptylamine, octylamine, nonylamine, decylamine, pentadecylamine, hexadecylamine, heptadecylamine, octadecylamine, methylethylamine, methyl-iso-propylamine, methylhexylamine, methyinonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-iso-propylamine, di-n-butylamine, di-n-amylamine, di-iso-amylamine, dihexylamine, diheptylamine, dioctylamine, ethanolamine, n-propanolamine, iso-propanolamine, N,N-diethanolamine, N-ethylpropanolamine, N-butylethanolamine, allylamine, n-butenyl-2-amine, n-pentenyl-2-amine, 2,3-dimethylbutenyl- 2-amine, di-butenyl-2-amine, n-hexenyl-2-amine, propylenediamine, trimethylamine, triethylamine, tri-n-propylamine, tri-iso-propylamine, tri-n-butylamine, tri-iso-butylamine, tri-sec-butylamine, tri-n-amylamine, methoxyethylamine and ethoxyethylamine; heterocyclic amines such as, for example, pyridine, quinoline, isoquinoline, morpholine, thiomorpholine, piperidine, pyrrolidine, indoline, quinuclidine and azepine; primary arylamines such as, for example, anilines, methoxyanilines, ethoxyanilines, o,m,p-toluidines, phenylenediamines, benzidines, naphthylamines and o,m,pchloroanilines; but in particular triethyl amine, iso-propylamine and di-iso-propylamine.

The salts of the compounds of the formula I which have basic groups, in particular basic pyridyl, pyrimidinyl, pyrazinyl, pyridazinyl and pyrazolyl rings or of the derivatives having amino groups such as, for example, alkylamino and dialkylamino groups in the definition of $R_2$ or $R_3$ are, for example, salts with inorganic and organic acids such as, for example, hydrohalic acids such as hydrofluoric acid, hydrochloric acid, hydrobromic acid or hydriodic acid, and also sulfuric acid, phosphoric acid, nitric acid and organic acids such as acetic acid, trifluoroacetic acid, trichloroacetic acid, propionic acid, glycolic acid, thiocyanic acid, citric acid, benzoic acid, oxalic acid, formic acid, benzenesulfonic acid, p-toluenesulfonic acid and methanesulfonic acid.

The presence of an asymmetric carbon atom in the compounds of the formula I, for example in the substituent $R_2$ or $R_3$=$OR_6$, in which $R_6$ is a branched alkyl, alkenyl, haloalkyl or alkoxyalkyl group, or $R_3$=$S(O)_{n1}R_9$, in which, for example, $n_1$=1 and/or $R_9$ is a branched alkyl, alkenyl, haloalkyl or alkoxyalkyl group, results in the fact that the compounds may occur not only in optically active single isomers, but also in the form of racemic mixtures. The present invention is to be understood as meaning, by active ingredients of the formula I, not only the pure optical antipodes but also the racemates or diastereomers.

If an aliphatic C=C double bond is present, geometric isomerism may occur. The present invention also extends to these isomers.

Preferred compounds of the formula I are those in which $R_2$ is methyl, halogen, hydroxyl, nitro, amino or cyano; $R_3$ is nitro, amino, $R_4NH—$, $R_4R_5N—$, azido or $ClS(O)_2—$; $R_9$, if $n_1$ is 0, is additionally hydrogen, $C_1$–$C_8$alkylcarbonyl or $R_{10}X_2C(O)—$; $R_{13}$ is hydrogen, $C_1$–$C_8$alkyl, $C_3$–$C_8$alkenyl, $C_3$–$C_8$alkynyl, $C_1$–$C_8$haloalkyl, $C_1$–$C_4$alkoxy-$C_1$–$C_4$alkyl, $C_1$–$C_4$alkylcarbonyl, $C_1$–$C_4$haloalkylcarbonyl, benzoyl or benzoyl which is mono- to trisubstituted on the phenyl ring by halogen, $C_1$–$C_4$alkyl or $C_1$–$C_4$haloalkyl; and $R_4$, $R_5$, $R_{10}$ and $X_2$ have the meanings given under formula I.

Other preferred compounds of the formula I are those in which W is the group

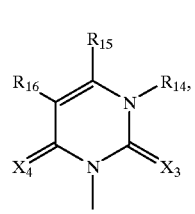

(W$_1$)

and $R_{14}$, $R_{15}$, $R_{16}$, $X_3$ and $X_4$ have the meanings given under formula I. Especially preferred amongst those are compounds in which $R_{14}$ is methyl, $R_{15}$ is trifluoromethyl, $R_{16}$ is hydrogen, and $X_3$ and $X_4$ are oxygen.

Other preferred compounds of the formula I are those in which W is the group

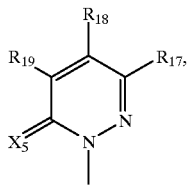
(W$_2$)

and R$_{17}$, R$_{18}$, R$_{19}$ and X$_5$ have the meanings given under formula I. Especially preferred compounds are, in particular, those in which R$_{17}$ and R$_{19}$ independently of one another are hydrogen or C$_1$–C$_3$alkyl; R$_{18}$ is trifluoromethyl, and X$_5$ is oxygen.

Other preferred compounds of the formula I are those in which W is the group

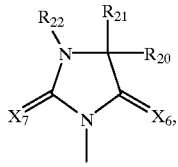
(W$_3$)

R$_{20}$, R$_{21}$ and R$_{22}$ have the meanings given under formula I, and X$_6$ and X$_7$ are oxygen. Especially preferred amongst these compounds are, in particular, those in which R$_{21}$ and R$_{22}$ together form a C$_4$alkylene bridge which can be substituted by halogen, hydroxyl or =O.

Other preferred compounds of the formula I are those in which W is the group

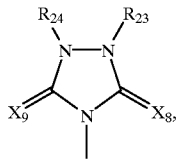
(W$_4$)

R$_{23}$ and R$_{24}$ have the meanings given under formula I, and X$_8$ and X$_9$ are oxygen. Especially preferred amongst these compounds are those in which R$_{23}$ and R$_{24}$ together form a C$_3$ or C$_4$alkylene bridge.

Other preferred compounds of the formula I are those in which R$_1$ is fluorine or chlorine, R$_2$ is chlorine, bromine or cyano, R$_3$ is R$_6$O—, and R$_6$ is C$_1$–C$_4$alkyl, C$_1$–C$_4$alkoxy-C$_1$–C$_4$alkyl, C$_3$–C$_6$alkenyloxy-C$_1$–C$_4$alkyl, C$_3$–C$_6$alkenyl, C$_3$–C$_6$alkynyl or benzyl. Especially important amongst these compounds are, in particular, those in which R$_2$ is chlorine or cyano.

Preferred compounds of the formula I, are, furthermore, those in which R$_2$ is methyl, halogen, hydroxyl, nitro, amino, cyano, C$_1$–C$_4$haloalkyl, C$_1$–C$_4$alkoxy or C$_1$–C$_4$haloalkoxy.

The process according to the invention for the preparation of compounds of the formula I is carried out in a manner similar to known processes and comprises, to prepare those compounds of the formulae I$_a$, I$_{aa}$, I$_b$ and I$_{bb}$

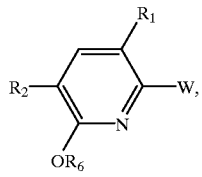
(I$_a$)

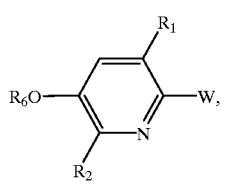
(I$_{aa}$)

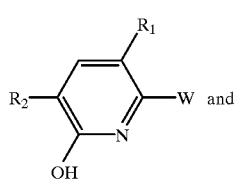
(I$_b$)

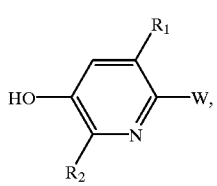
(I$_{bb}$)

in which R$_1$, R$_2$, R$_6$ and W have the meanings given under formula I, R$_2$ preferably being halogen, oxidizing, for example, a compound of the formula III

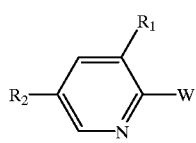
(III)

in a suitable solvent to first give the compound of the formula IV

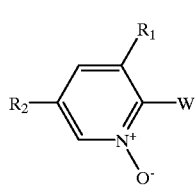
(IV)

subsequently subjecting this compound to a rearrangement reaction in an inert solvent in the presence of an anhydride or of antimony pentachloride (so-called Katada reaction) and, after aqueous workup, obtaining the compounds of the formulae I$_b$ and I$_{bb}$

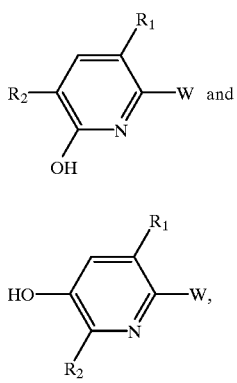
(I_b)

(I_bb)

the radicals $R_1$, $R_2$ und W in the compounds of the formulae IIII, IV, $I_b$ and $I_{bb}$ having the abovementioned meanings, and converting these compounds with a compound of the formula V $$R_6\text{—L} \qquad (V)$$

in which $R_6$ has the meaning given under formula I, with the exception of $R_6$ being hydrogen, and L is a leaving group such as, for example, halogen, in particular chlorine, bromine or iodine, or a sulfonate, in particular $CH_3S(O)_2O$— or

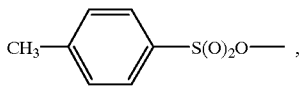

in the presence of an inert solvent and of a base to give the isomeric compounds of the formulae $I_a$, $I_{aa}$ and II

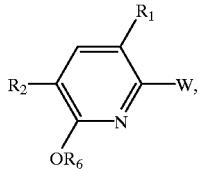
(I_a)

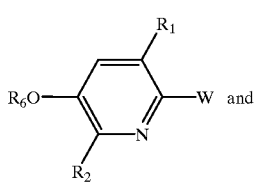
(I_aa)
and

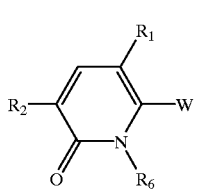
(II)

in which $R_1$, $R_2$, $R_6$ and W have the abovementioned meanings, subsequently removing the compounds of the formula $I_a$ and $I_{aa}$ from the pyridone by-product of the formula II and, if appropriate, further functionalizing the compounds as defined for $R_3$ under formula I.

The process according to the invention for the preparation of compounds of the formula I is carried out by a method similar to known processes and comprises, to prepare those compounds of the formula $I_c$

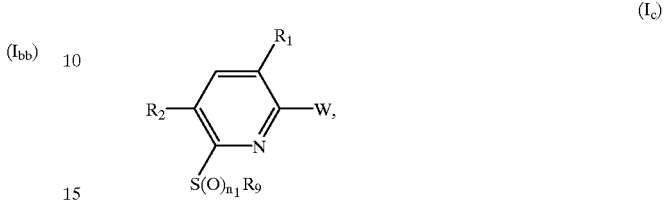
(I_c)

in which $R_1$, $R_2$, $R_9$, $n_1$ and W have the meanings given under formula I, halogenating, for example, a compound of the formula $I_b$

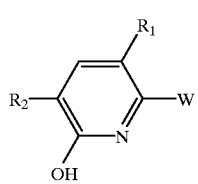
(I_b)

in which $R_1$, $R_2$ and W have the abovementioned meanings, with a halogenating agent such as, for example, phosphorus oxychloride, if appropriate in the presence of a base and of a suitable solvent and obtaining the compound of the formula VI

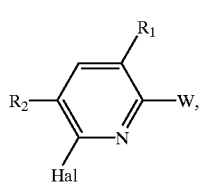
(VI)

the radicals $R_1$, $R_2$ and W in the compounds of the formulae $I_b$ and VI having the abovementioned meanings and Hal in the compound of the formula VI being fluorine, chlorine or bromine, converting these compounds with a sulfur reagent such as, for example, hydrogen sulfide or its alkaline earth metal salt in the presence of a base and of a suitable solvent to give the compound of the formula $I_d$

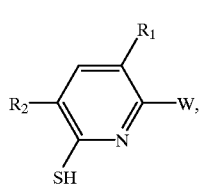
(I_d)

subsequently reacting this compound with a compound of the formula VII

$$R_9\text{—L} \qquad (VII)$$

in which $R_9$ has the meaning given under formula I with the exception of $R_9$ being hydrogen, and L is a leaving group, if appropriate in the presence of a solvent and of a base, to give the compound of the formula $I_c$

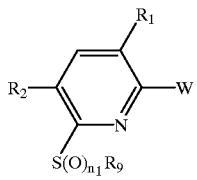

(I$_c$)

in which $R_1$, $R_2$, $R_9$ and W have the abovementioned meanings and $n_1$ is 0, and, if appropriate, oxidizing this compound to give the compound of the formula $I_c$, in which $n_1$ is 1 or 2.

The compounds of the formula $I_c$ in which $n_1$ is 2 and $R_9$ is an unsubstituted or substituted $C_1$–$C_4$alkyl or phenyl can—like the compounds of the formula VI which are substituted in the 6-position by halogen—be used as intermediates for the preparation of compounds of the formula I by substituting the group $R_9S(O)_2$— with O—, N— or S-nucleophiles. The substitution of an alkylsulfonyl or phenylsulfonyl group on pyridine rings with nucleophiles is described, for example, in Bull. Chem. Soc. Jp. 60 (1987), 335 and 343, Het. 24 (1986), 3019 and J. Het. Chem. 22 (1985),1583.

The process according to the invention for the preparation of compounds of the formula I is carried out by a method similar to known processes and comprises, to prepare those compounds of the formula I

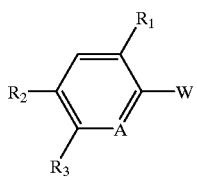

(I)

in which A, $R_1$, $R_2$ and W have the meanings given under formula I and $R_3$ is $R_6O$—, $R_9S(O)_{n1}$—, amino, $R_4NH$— or $R_4R_5N$—, halogenating, for example, a compound of the formula III or IV

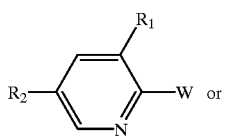

(III)

or

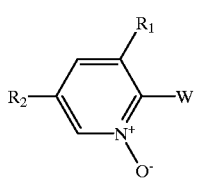

(IV)

and obtaining the compound of the formula VI

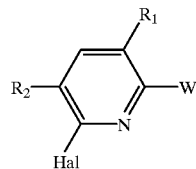

(VI)

and subsequently either converting this compound a) with a compound of the formula IX, if appropriate in the presence of a base and of an inert solvent, or IXa

or

where $R_6$ has the meaning given under formula I, M in the compound of the formula IXa is an alkali metal atom or alkaline earth metal atom and t is 1 or 2 or b) with a compound of the formula X, if appropriate in the presence of a base and of an inert solvent, or Xa

or

where $R_9$ has the meanings given under formula I, M in the compound of the formula Xa is an alkali metal atom or alkaline earth metal atom and t is 1 or 2, to give first the compound of the formula $I_c$

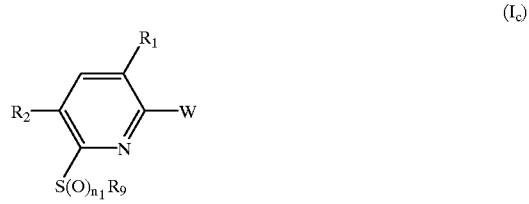

(I$_c$)

in which $R_1$, $R_2$, $R_9$ and W have the abovementioned meanings and $n_1$ is 0, and, if appropriate, oxidizing this compound to give the compound of the formula $I_c$ in which $n_1$ is 1 or 2, for example using hydrogen peroxide, or reacting the compound of the formula VI c) with a compound of the formula XI

(XI)

in which $R_9$ has the abovementioned meaning and $M_1^+$ is an alkali metal ion or d) with a compound of the formula XII, if appropriate in the presence of a base and of an inert solvent, or XIIa

  (XII)

or

  (XIIa)

in which $R_4$ has the meaning given under formula I and $M_1^+$ is an alkali metal ion or e) with a compound of the formula XII, if appropriate in the presence of a base and of an inert solvent, or XIIIa

  (XIII)

or

  (XIIIa)

in which $R_4$ and $R_5$ have the meanings given under formula I and $M_1^+$ is an alkali metal ion, and, if appropriate, subsequently oxidizing the compounds of the formula I (A=N—) which have been obtained by the above variants a) to e)

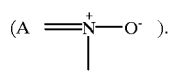

The process according to the invention for the preparation of compounds of the formula I is carried out by a method similar to known processes such as described, for example, in EP-A-0 438 209 or DE-OS-19 604 229 and comprises, to prepare those compounds of the formula $I_e$

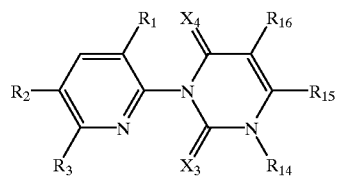  ($I_e$)

in which $R_1$, $R_2$, $R_3$, $R_{14}$, $R_{15}$, $R_{16}$, $X_3$ and $X_4$ have the meanings given under formula I and $R_3$ is additionally hydrogen, converting, for example a compound of the formula XIV

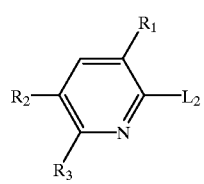  (XIV)

in which $R_1$, $R_2$ and $R_3$ have the abovementioned meanings and $L_2$ is a leaving group such as, for example, halogen, e.g. fluorine, chlorine or bromine, or $C_1$–$C_4$alkyl- or phenylsulfonyl group or a $C_1$–$C_4$alkyl- or phenylsulfonyloxy group in the presence of an inert solvent and of ammonia, if appropriate in an autoclave, at temperatures of –10 to 180° C. to give the compound of the formula XV

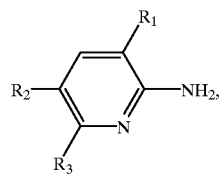  (XV)

converting this compound in the presence of a base and of a solvent a) with chloroformic ester of the formula XVI

  (XVI)

in which $X_3$ has the meaning given under formula I to give the compound of the formula XVII

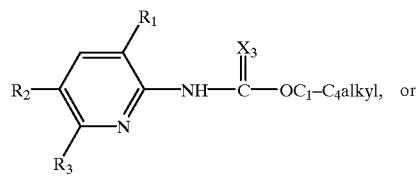  (XVII)

b) with oxalyl chloride, phosgene or thiophosgene to give the compound of the formula XVIII

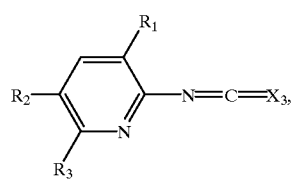  (XVIII)

subsequently subjecting the compound of the formula XVII or XVIII to a cyclization reaction with an enamine derivative of the formula XIX

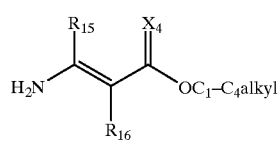  (XIX)

in which $R_{15}$ and $R_{16}$ have the meanings given under formula I and $X_4$ is oxygen in the presence of 0.1–1.5 equivalents of a base in an inert solvent, and obtaining the compound of the formula XX

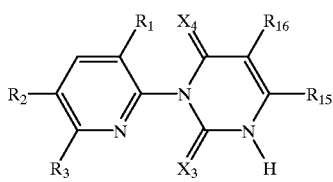

(XX)

in which $R_1$, $R_2$, $R_3$, $R_{15}$, $R_{16}$, $X_3$ and $X_4$ have the abovementioned meanings, further reacting this compound in the presence of an inert solvent and a base with a) a compound of the formula XXI $R_{14}$—L  (XXI), in which $R_{14}$ is $C_1$–$C_3$alkyl or $C_1$–$C_3$haloalkyl and L is a leaving group or b) with a hydroxylamine derivative of the formula XXII $NH_2$—$L_1$  (XXII)

in which $L_1$ is a leaving group, and, if appropriate, treating the compounds of tho formula $I_e$ in which $X_4$ is oxygen, which have been obtained by the above variants a) and b), with a thionizing reagent ($X_4$ sulfur).

The process according to the invention for the preparation of compounds of the formula I is carried out by a method similar to known processes and comprises, to prepare those compounds of the formula $I_f$

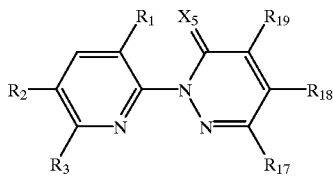

$(I_f)$ in which $R_1$, $R_2$, $R_3$, $R_{17}$, $R_{18}$, $R_{19}$ and $X_5$ have the meanings given under formula I and $R_3$ is additionally hydrogen, for example, either a) converting a compound of the formula XIV

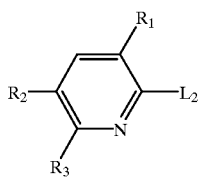

(XIV)

in which $R_1$, $R_2$ and $R_3$ have the abovementioned meanings and $L_2$ is a leaving group such as, for example, halogen, e.g. fluorine, chlorine or bromine, or $C_1$–$C_4$alkyl- or phenylsulfonyl group or a $C_1$–$C_4$alkyl- or phenylsulfonyloxy group, with hydrazine, preferably in a protic solvent, to give the compound of the formula XXIII

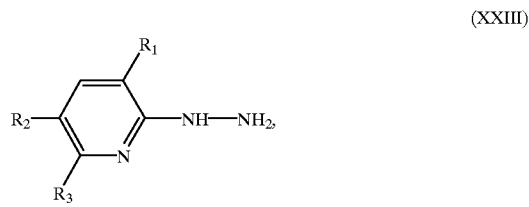

(XXIII)

further reacting this compound with a compound of the formula XXIV or XXIVa

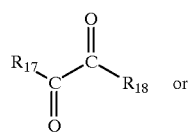

(XXIV)

or

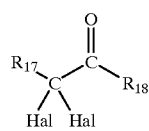

(XXIVa)

in which $R_{17}$ and $R_{18}$ have the meanings given under formula I and Hal in the compound of the formula XXIVa is chlorine and bromine, or b) first diazotizing, advantageously with exclusion of water, a compound of the formula XV

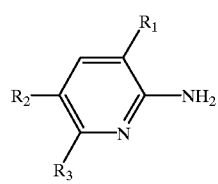

(XV)

in which $R_1$, $R_2$ and $R_3$ have the abovementioned meanings, subsequently further reacting this compound with a compound of the formula XXVI

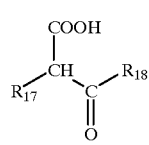

(XXVI)

in which $R_{17}$ and $R_{18}$ have the abovementioned meanings, and obtaining the compound of the formula XXV

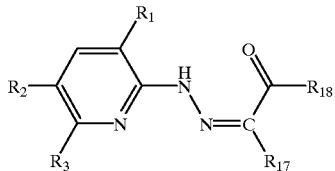

(XXV)

which is cyclized, if appropriate in the presence of a base such as, for example, 4-dimethylaminopyridino, and of a compound of the formula XXVII

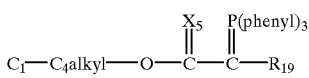

(XXVII)

in which $R_{19}$ has the abovementioned meaning and $X_5$ is oxygen, and, if appropriate, treating this compound with a thionizing reagent ($X_5$ sulfur).

The process according to the invention for the preparation of compounds of the formula I is carried out by a method similar to known methods such as described in, for example, EP-A-0 272 594, EP-A-0 493 323, DE-A-3 643 748, WO 95/23509, U.S. Pat. No. 5,665,681 and U.S. Pat. No. 5,661,109 and comprises, to prepare those compounds of the formula $I_g$

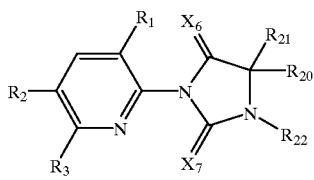

($I_g$)

in which $R_1$, $R_2$, $R_3$, $R_{20}$, $R_{21}$, $R_{22}$, $X_6$ and $X_7$ have the meanings given under formula I and $R_3$ is additionally hydrogen, for example, either reacting a) in the presence of a solvent or of a base, a compound of the formula XVIIa

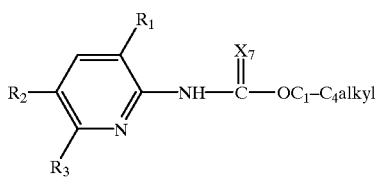

(XVIIa)

or b) if appropriate in a suitable solvent, a compound of the formula XVIIa

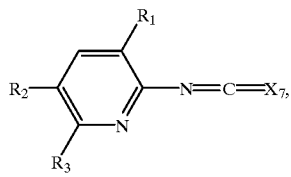

(XVIIIa)

the radicals $R_1$, $R_2$, $R_3$ and $X_7$ in the compounds of the formulae XVIIa and XVIIIa having the abovementioned meaning, with a compound of the formula XXVIII

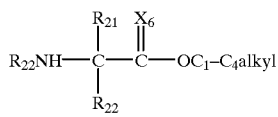

(XXVIII)

in which $R_{20}$, $R_{21}$, $R_{22}$ and $X_6$ have the abovementioned meanings and obtaining the compound of the formula XXIX

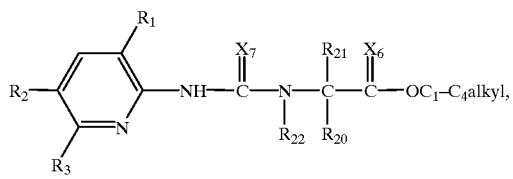

(XXIX)

subjecting this compound to cyclization in the presence of a suitable solvent and of a base, and, subsequently, if appropriate, c) if $R_{22}$ is hydrogen, reacting this compound with a compound of the formula XXX $R_{22}$—L  (XXX)

in which $R_{22}$ is $C_1$–$C_3$alkyl and L is a leaving group and, d) if $X_6$ and/or $X_7$ are oxygen, treating this compound with a thionizing reagent ($X_6$ and/or $X_7$ sulfur).

The process according to the invention for the preparation of compounds of the formula I is carried out by a method similar to known methods such as described in, for example, EP-A-0 210 137, DE-A-2 526 358, EP-A-0 075 267 and EP-A-0 370 955 and comprises, to prepare those compounds of the formula $I_h$

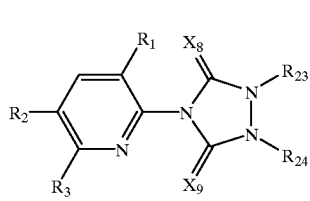

($I_h$)

in which $R_1$, $R_2$, $R_3$, $R_{23}$, $R_{24}$, $X_8$ and $X_9$ have the meanings given under formula I and $R_3$ is additionally hydrogen, reacting, for example, a) in the presence of a solvent and of a base, a compound of the formula XVIIb

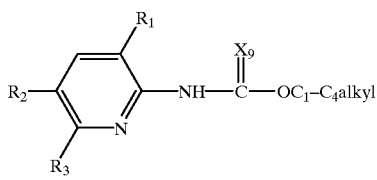

(XVIIb)

or b) if appropriate in a suitable solvent, a compound of the formula XVIIIb

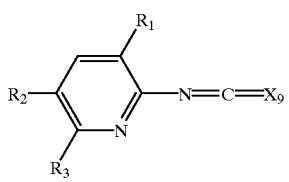

(XVIIIb)

in which the radicals $R_1$, $R_2$, $R_3$ and $X_9$ in the compounds of formulae XVIIb and XVIIIb having the abovementioned meanings with a compound of the formula XXXI

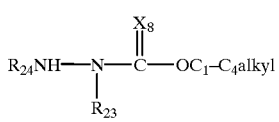

(XXXI)

in which $R_{23}$, $R_{24}$ and $X_8$ have the abovementioned meanings, and obtaining the compound of the formula XXXII

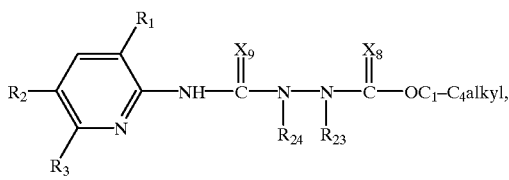

(XXXII)

subjecting this compound to cyclization in the presence of a suitable solvent and of a base, and subsequently if appropriate, c) if $R_{23}$ and/or $R_{24}$ are hydrogen, further reacting this compound with a compound of the formula XXXIIIa or XXXIIIb $R_{23}$—L  (XXXIIIa)

or $R_{24}$—L  (XXXIIIb)

in which the radicals $R_{14}$ to $R_{24}$ and $X_3$ to $X_9$ have the meanings given under formula I, if appropriate in the presence of a suitable solvent and of a base, and subjecting the resulting compounds of the formula I (A =N—) to oxidation in which $R_{23}$ and $R_{24}$ independently of one another are $C_1$–$C_3$alkyl and L is a leaving group, or with a Michael acceptor, and, d) if $X_8$ and/or $X_9$ are oxygen, treating this compound with a thionizing reagent ($X_8$ and/or $X_9$ sulfur).

The process according to the invention for the preparation of compounds of the formula I is carried out by a method similar to known processes such as described, for example, in J. Het. Chem. 15 (1978), 1221, and comprises reacting, for example, a compound of the formula XIV

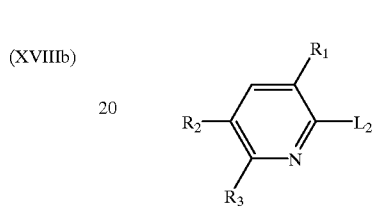

(XIV)

in which $R_1$, $R_2$ and $R_3$ have the meanings given under formula I, $R_3$ is additionally hydrogen and $L_2$ is a leaving group such as, for example, halogen, e.g. fluorine, chlorine or bromine, or a $C_1$–$C_4$alkyl- or penyl-sulfonyl group or a $C_1$–$C_4$alkyl- or phenyl-sulfonyloxy group with a compound of the formula $W_{O1}$, $W_{O2}$, $W_{O3}$ or $W_{O4}$

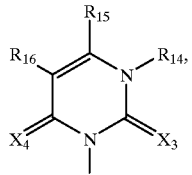

($W_{O1}$)

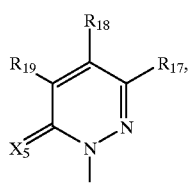

($W_{O2}$)

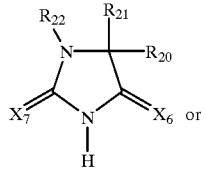

($W_{O3}$)

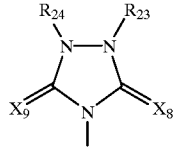

($W_{O4}$)

in which the radicals $R_{14}$ to $R_{24}$ and $X_3$ to $X_9$ have the meanings given under formula I, if appropriate in the presence of a suitable solvent and of a base, and subjecting the resulting compounds of the formula I (A=N—) to oxidation

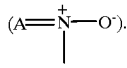

A further process according to the invention for the preparation of specifically substituted compounds of the formula I is carried out by a manner similar to known processes and comprises, to prepare those compounds of the formula $I_j$;

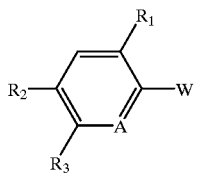
(I$_j$)

in which $R_1$ is hydrogen or fluorine, $R_2$ is cyano, $R_3$ is halogen, amino, $R_4NH$—, $R_4R_5N$—, azido, $R_6O$— or $R_9S(O)_{n1}$— and $R_4$, $R_5$, $R_6$, $R_9$, $n_1$, A and W have the meanings given under formula I, reacting, for example, a compound of the formula XIVa

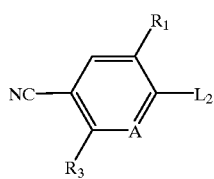
(XIVa)

in which $L_2$ is a leaving group such as, for example, chlorine, bromine or $C_1$–$C_4$alkylsulfonyl, $R_3$ is chlorine or bromine and $R_1$ has the abovementioned meaning, with a compound of the formula $W_{01}$, $W_{02}$, $W_{03}$ or $W_{04}$

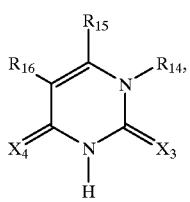
(W$_{01}$)

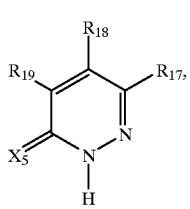
(W$_{02}$)

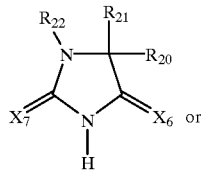
(W$_{03}$)

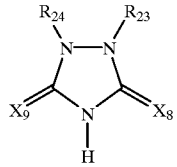
(W$_{04}$)

in which the radicals $R_{14}$ to $R_{24}$ and $X_3$ to $X_9$ have the meanings given under formula I, or salts of these, if appropriate in a suitable organic solvent and in the presence of a base, such as, for example, carbonates, e.g. potassium carbonate, at elevated temperature or at the reflux temperature of the solvent used to give the compound of the formula $I_i$;

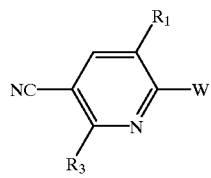
(I$_i$)

in which $R_3$ is chlorine or bromine and $R_1$ and W have the abovementioned meanings, and subjecting this compound to a nucleophilic aromatic substitution reaction, either a) with a compound of the formula IX, if appropriate in the presence of a base and of an inert solvent, or IXa

$R_6OH$ (IX)

or

$[R_6$—$O]^-_tM^{t+}$ (IXa)

in which $R_6$ has the meaning given under formula I, M in the compound of the formula IXa is an alkali metal atom or alkaline earth metal atom and t is 1 or 2, or b) with a compound of the formula X, if appropriate in the presence of a base and of an inert solvent, or Xa

$R_9SH$ (X)

or

$[R_9$—$S]^-_tM^{t+}$ (Xa)

in which $R_9$ has the meaning given under formula I, M in the compound of the formula Xa is an alkali metal atom or alkaline earth metal atom and t is 1 or 2, and first converting it into the compound of the formula $I_i$;

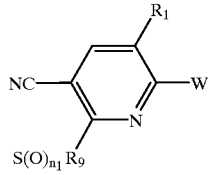 (I<sub>i</sub>)

in which $R_1$, $R_9$ and W have the abovementioned meanings and $n_1$ is 0 and, if appropriate, oxidizing this compound to give the compound of the formula $I_i$ in which $n_1$ is 1 or 2, for example using hydrogen peroxide, or c) with a compound of the formula XI

 (XI)

in which $R_9$ has the abovementioned meanings and $M_1^+$ is an alkali metal ion, or d) with a compound of the formula XII, if appropriate in the presence of a base and of an inert solvent, or XIIa

 (XII)

or

 (XIIa)

in which $R_4$ has the meaning given under formula I and $M_1^+$ is an alkali metal ion or e) with a compound of the formula XIII, if appropriate in the presence of a base and of an inert solvent, or XIIIa

 (XIII)

or

 (XIIIa)

in which $R_4$ and $R_5$ have the meanings given under formula I and $M_1^+$ is an alkali metal ion, and, if appropriate, subsequently oxidizing the compounds of the formula $I_i$ (A =N—) obtained by the above variants a) to e)

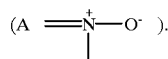

The preparation of compounds of the formulae $I_a$, $I_{aa}$, $I_b$ and $I_{bb}$

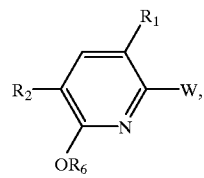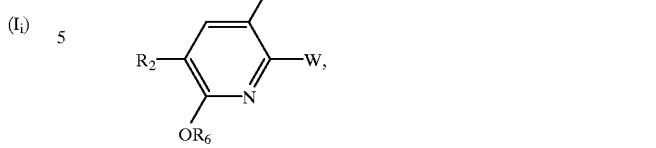 (I<sub>a</sub>)

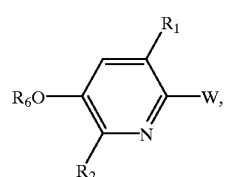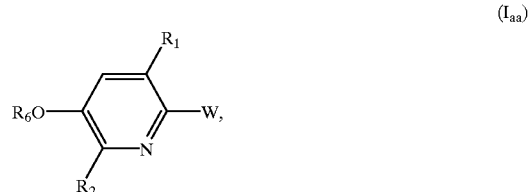 (I<sub>aa</sub>)

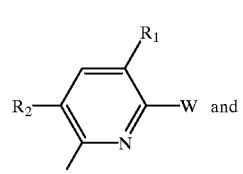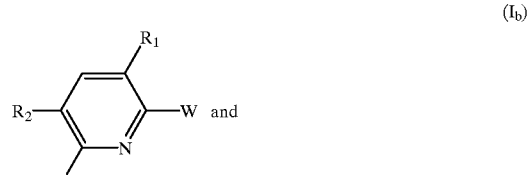 (I<sub>b</sub>)

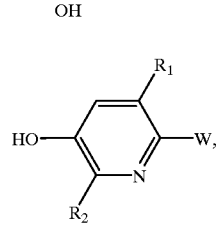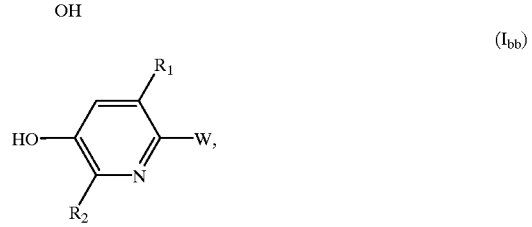 (I<sub>bb</sub>)

in which $R_1$, $R_2$, $R_6$ and W have the meanings given under formula I, $R_2$ preferably being halogen, is illustrated in reaction scheme 1 which follows.

Reaction scheme 1:

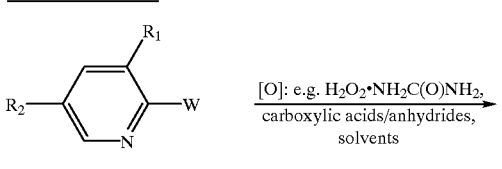

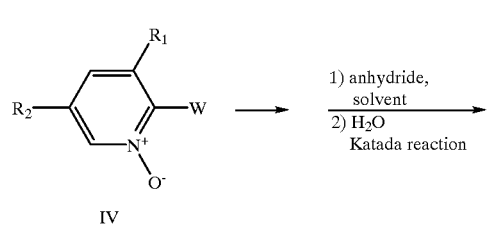

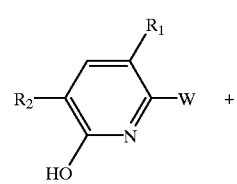

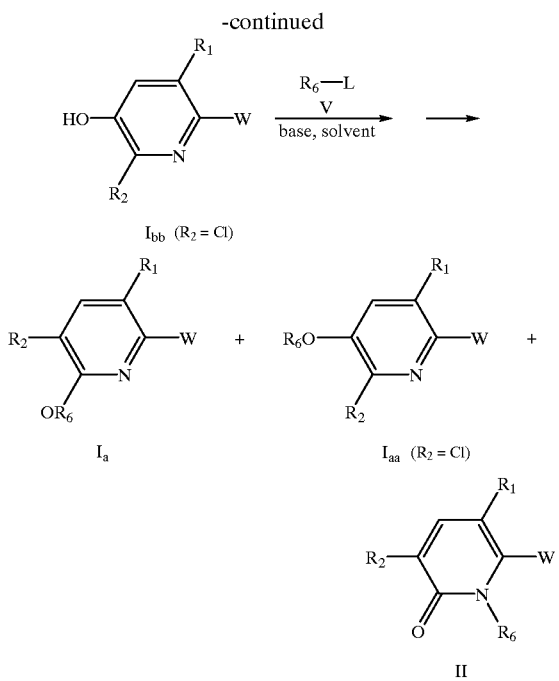

The pyridine N-oxides of the formula IV (reaction scheme 1) can be prepared by known methods (for example Org. Synth. 4 (1963), 828; ibid. 3 (1955), 619; U.S. Pat. No. 3,047,579; and B. Iddon and H. Suschitzky in "Polychloroaromatic Compounds", Editor H. Suschitzky, Plenum Press, London 1974, page 197), expediently by reacting the pyridine derivatives of the formula III with oxidants such as, for example, organic peracids, for example m-chloroperbenzoic acid (MCPBA), peracetic acid and pertrifluoroacetic acid, or aqueous hydrogen peroxide solution or hydrogen peroxide/urea adduct together with carboxylic acids and/or carboxylic anhydrides, or inorganic peracids, for example pertungstic acid (Caro's acid). Suitable solvents are, for example, water, organic acids such as, for example, acetic acid and trifluoroacetic acid, halogenated hydrocarbons such as, for example, dichloromethane and 1,2-dichloroethane, esters, such as, for example, ethyl acetate, ethers such as, for example, tetrahydrofuran and dioxane, or mixtures of these. The reaction temperatures are in the range of −20° C. to 100° C., depending on the solvent or solvent mixture used.

The 6-hydroxypyridine derivatives of the formula $I_b$ can be prepared by known methods (for example Quart. Rev. 10 (1956), 395; J. Am. Chem. Soc. 85 (1963), 958; and J. Org. Chem. 26 (1961), 428), expediently by means of subjecting the pyridine N-oxides of the formula IV to a rearrangement reaction in the presence of anhydrides, for example acetic anhydride, trifluoroacetic anhydride and methanesulfonic anhydride, in a suitable inert solvent such as, for example, halogenated hydrocarbons, e.g. dichloromethane and 1,2-dichloroethane, amides, e.g. N,N-dimethylformamide and 1-methyl-2-pyrrolidone (NMP), if appropriate in the presence of sodium acetate. The reaction temperatures are generally in the range of from −30° C. to 80° C. The same reaction, in particular where $R_2$ is chlorine, also gives the isomeric 6-chloro-5-hydroxypyridine derivatives of the formula $I_{bb}$ by further rearranging the N-oxides of the formula IV. The primary products 6-O-acyl- or 6-O-sulfonylpyridines can be hydrolyzed readily by means of aqueous work-up of the reaction mixture to give the desired 6-hydroxypyridines of the formula $I_b$. Similarly to Tetrahedron 37 (1981), 187, antimony pentachloride (Katada reaction) is also suitable for the above rearrangement reaction as further variant. The same applies to the isomeric 5-O-acylated derivatives. If appropriate, the isomers of the formula $I_b$ or $I_{bb}$ can be separated by known methods. However, they may also be reacted further as isomer mixture, the compounds of the formulae $I_a$, $I_{aa}$ and II being obtained under identical reaction conditions.

The subsequent alkylation can be effected by known methods (for example Org. Prep. Proced. Int. 9 (1977), 5; J. Org. Chem. 35 (1970), 2517; ibid. 32 (1967), 4040; and Tetrahedron Lett. 36 (1995), 8917, and Preparation Example H6), expediently with the aid of an alkylating reagent of the formula V. As a rule, alkylation leads to an isomer mixture composed of the compounds of the formulae $I_a$ and, if appropriate, $I_{aa}$ (O-alkylation) and II (N-alkylation). A further variant of preparing the alkylation products is to react the hydroxypyridines of the formula $I_b$ or $I_{bb}$ with an alcohol of the formula $R_6OH$ in which $R_6$ has the meaning given under formula I in an inert solvent such as, for example, tetrahydrofuran, dioxane or dimethoxyethane in the presence of a phosphine such as, for example, triphenylphosphine and an azodicarboxylic acid derivative such as, for example, diethyl azodicarboxylate. Such Mitsunobu reactions are described, for example, in Tetrahedron Letters 1994, 2819.

Suitable solvents are, for example, alcohols, e.g. methanol, ethanol and isopropanol, amides, e.g. N,N-dimethylformamide (DMF) and 1-methyl-2-pyrrolidone (NMP), sulfoxides, e.g. dimethyl sulfoxide (DMSO) and sulfones, e.g. sulfolane, or mixtures of these with water, ethers, e.g. diethyl ether, tert-butyl methyl ether, dimethoxyethane (DME), dioxane and tetrahydrofuran (THF), esters, e.g. ethyl acetate, ketones, e.g. acetone and methyl ethyl ketone, and hydrocarbons, e.g. n-hexane, toluene and xylenes. Suitable bases are organic and inorganic bases such as, for example, alkali metal alkoxides, e.g. sodium mothoxida, sodium ethoxide and potassium tert-butoxide, trialkylammonium hydroxides, trialkylammonium halides, e.g. triethylammonium iodide, alkali metal and alkaline earth metal hydrides, e.g. sodium hydride together with lithium bromide (2 equivalents), alkali metal carbonates, e.g. potassium carbonate, alkali metal hydroxides, e.g. sodium hydroxide and potassium hydroxide, and caesium fluoride. The reaction temperatures for the alkylation are in the range of from −20° C. to reflux temperature of the solvent used, preferably 0° C. to 100° C. The isomers of the formulae $I_a$, $I_{aa}$, $I_{bb}$ and II can be separated readily by silica gel chromatography or fractional crystallization.

If appropriate, the desired pyridine derivatives of the formulae $I_a$, $I_{aa}$ and $I_{bb}$, which have been separated from the by-product of the formula II, can readily be functionalized further by known methods in accordance with the definition of $R_3$ under formula I.

The preparation of the compounds of the formula $I_c$

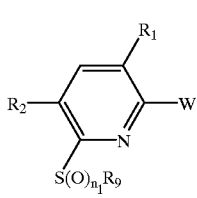

(1c)

in which $R_1$, $R_2$, $R_9$, $n_1$ and W have the meanings given under formula I is illustrated in reaction scheme 2 which follows.

Reaction scheme 2:

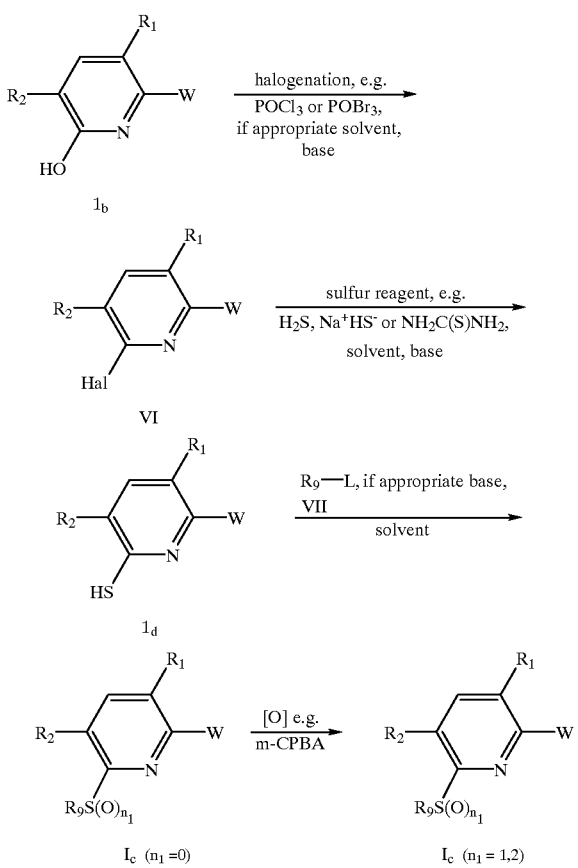

In accordance with reaction scheme 2, the 6-halopyddines of the formula VI can be obtained from the corresponding 6-hydroxypyridines of the formula $I_b$ by means of halogenation, for example by means of phosphorus oxychloride or phenyl dichlorophosphate, if appropriate in the presence of a base in an inert solvent, by methods similar to "Pyridine and its Derivatives", Part 2, Editor E. Klingsberg, New York 1961, page 326 et seq. The 6-halopyridines of the formula VI can be converted into the corresponding 6-mercaptopyridines of the formula $I_d$ by a method similar to known processes (for example as described in "Methoden der Organischen Chemie" [Methods in Organic Chemistry] (Houben-Weyl), Volume E/b, Heteroarene part 2, Georg Thieme Verlag Stuttgart, 1992, page 286 et seq.) using a suitable sulfur reagent such as, for example, hydrogen sulfide or its alkali metal salt, or thiourea in the presence of an inert solvent and of a base such as, for example, tertiary amines, alkali metal and alkaline earth metal hydroxides, or the corresponding alkali metal or alkaline earth metal oxides. The 6-mercaptopyridine derivative of the formula $I_d$ or its alkali metal salt is subsequently reacted with an alkylating reagent of the formula VII in which L is a leaving group, if appropriate in the presence of a base and of a suitable solvent, to give the 6-alkylmercapto derivative of the formula $I_c$. If appropriate, the thioethers of the formula $I_c$ ($n_1=0$) can be converted into the sulfoxides or sulfones $I_c$ ($n_1=1$ or 2) by known methods using an oxidant such as, for example, hydrogen peroxide, sodium periodate or m-chloroperbenzoic acid (m-CPBA) in an inert solvent such as, for example, dichloromethane. If appropriate, the reaction may also be stopped at the sulfoxide level.

The preparation of the compounds of the formula I in which A, $R_1$, $R_2$ and W have the meanings given under formula I and $R_3$ is $R_6O—$, $R_9S(O)_{n1}—$, amino, $R_4NH—$ or $R_4R_5N—$ is illustrated in reaction scheme 3 which follows.

Reaction scheme 3:

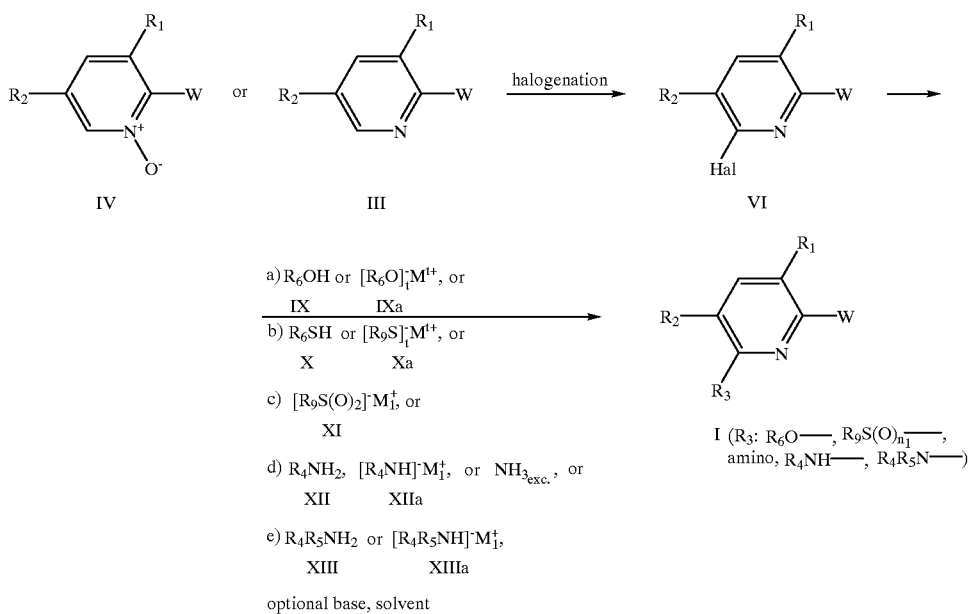

The 6-halopyridines of the formula VI can be obtained readily from the corresponding pyridine N-oxides of the formula IV or else from the pyridine derivatives of the formula III in accordance with reaction scheme 3 by known standard methods by means of halogenation, for example using phosphorus oxychloride or phosphorus oxybromide. The reactive 6-halopyridines of the formula VI, in turn, can be reacted either a) with an alcohol of the formula IX, if appropriate in the presence of a base and of an inert solvent, or with the corresponding alkali metal alkoxide of the formula IXa, b) with a thiol of the formula X, if appropriate in the presence of a base and of an inert solvent, or with the corresponding alkali metal thiolate of the formula Xa, c) with an alkali metal sulfinate of the formula XI, or d) and e) with an excess of ammonia, with an amine of the formula XII or XIII, if appropriate in the presence of a base and of an inert solvent, or with the corresponding alkali metal salt of the formula XIIa or XIIIa to give the desired compounds of the formula I in which $R_3$ is either $R_6O$—, $R_9S(O)_{n1}$—, amino, $R_4NH$— or $R_4R_5N$— by methods similar to known nucleophilic substitution reactions. The 6-mercaptopyridines of the formula I obtained in accordance with variant b) in which $R_3$ is $R_9S(O)_{n1}$ and $n_1$ is 0 can be converted, if appropriate, by known oxidation methods, for example using hydrogen peroxide, organic peracids, sodium perborate ($NaBO_3$), $(NH_4)_2Ce(NO_3)_6$, sodium periodate ($NaIO_4$) or manganese dioxide ($MnO_2$) to give the compounds of the formula I in which $R_3$ is $R_9S(O)_{n1}$— and $n_1$ is 1 or 2. Such oxidations are described, for example, in "Oxidations in Organic Chemistry", Editor M. Hudlicky, ACS Monograph 186, Washington D.C., 1990. The resulting sulfonyl derivatives of the formula I in which $R_3$ is $R_9S(O)_{n1}$ and $n_1$ is 2 can be further derivatized in accordance with the definition of $R_3$ by known methods, for example by nucleophilic aromatic substitution.

The above reactions in accordance with variants a), b), d) and e) are carried out with the non-deprotonated reagents of the formulae IX, X, XII and XIII, preferably in the presence of a base such as, for example, alkali metal hydroxides, alkaline earth metal hydroxides, alkaline earth metal oxides, alkali metal hydrides, e.g. sodium hydride, alkoxides, e.g. potassium tert-butoxide, quaternary ammonium hydroxides or tertiary amines, in a suitable inert solvent. Compounds of the formula I in which $R_3$ is nitro can be f) either obtained directly by means of nitration and separation of undesired position-isomeric nitro derivatives, g) obtained readily by means of oxidizing the amino group of the corresponding 6-aminopyridine derivative of the formula I ($R_3$ amino), or can be obtained by a method similar to what has been described, for example, in "Oxidations in Organic Chemistry", Editor M. Hudlicky, ACS Monograph 186, Washington D.C., 1990, from the corresponding pyridine azides

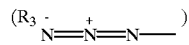

or from the corresponding amines by oxidation, for example with an alkali metal peroxodisulfate or ammonium peroxodisulfate, for example in concentrated sulfuric acid as solvent at reaction temperatures of from −20° to +30° C. Compounds of the formula I in which $R_3$ is an amino group ($NH_2$) can furthermore be obtained by rearranging corresponding acetamides ($R_3$=—$OCH_2CONH_2$) in the presence of a base, such as, for example, alkali metal carbonates, in an inert solvent such as, for example, dimethyl sulfoxide at temperatures of from 70° to 150° C.

Compounds of the formula I in which $R_2$ or $R_3$ is an amino group ($NH_2$) can furthermore also be obtained by reducing the corresponding azides. For example, these azides can be prepared by a Mitsunobu reaction from the hydroxyintermediates, hydrazoic acid ($HN_3$), a phosphine such as, for example, triphenylphosphine and an azo compound such as, for example, diethyl azodicarboxylate in an inert solvent. Such reactions are described, for example, in Synthesis 1992, 367.

The other compounds which come under the scope of the formula I can be prepared readily by methods similar to known standard processes taking into consideration the chemical reactivities of the pyridyl moiety and of the pyridyl -(Heterocyclyl)-W moiety (groups $W_1$ to $W_4$).

The preparation of the compounds of the formula $I_e$

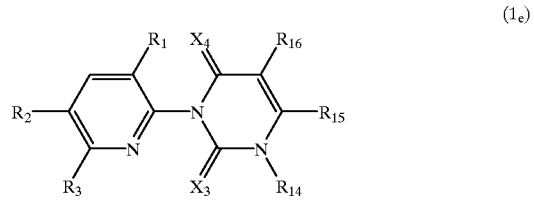

(1e)

in which $R_1$, $R_2$, $R_3$, $R_{14}$, $R_{15}$, $R_{16}$, $X_3$ and $X_4$ have the meanings given under formula I and $R_3$ is additionally hydrogen is illustrated in reaction scheme 4 which follows.

Reaction scheme 4:

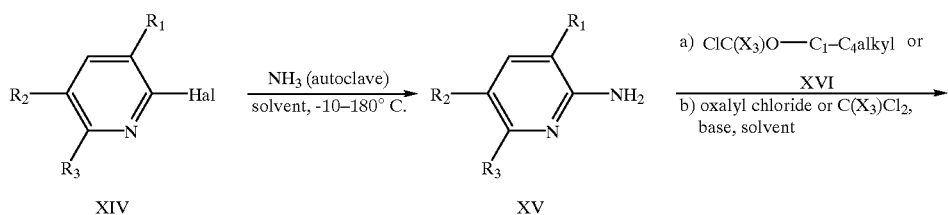

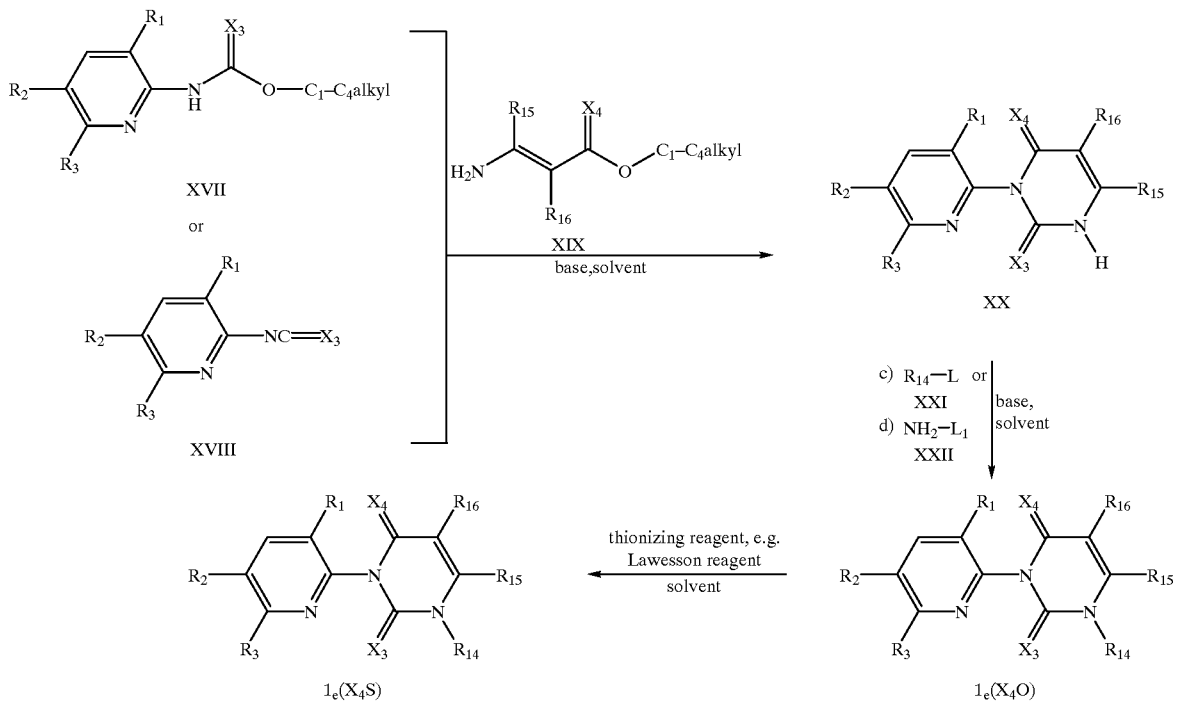

A multiplicity of known standard processes such as described, for example, in EP-A-0 438 209 and DE-OS-19 604 229 ($R_{15}$ cyano) is suitable for the preparation of the compounds of the formula $I_e$ according to the invention. Reaction scheme 4 shows a selection of suitable preparation methods, the choice of reaction routes and reagents depending on the reactivities of the substituents at the intermediate levels. For example, starting by reacting a compound of the formula XIV with ammonia in an inert solvent, if appropriate in an autoclave, at temperatures of −10 to 180° C., the aminopyridine of the formula XV can be obtained. The latter can be converted, in the presence of a base and of a solvent, either a) with chloroformic ster of the formula XVI ($X_3$ oxygen or sulfur) to give a pyridylcarbamate of the formula XVII, or b) with oxalyl chloride, phosgene ($X_3$ oxygen) or thiophosgene ($X_3$ sulfur) to give an iso(thio)cyanate of the formula XVIII. Such reactions are described, for example, in Angew. 1971, 407.

The carbamate and the iso(thio)cyanate of the formulae XVII and XVIII can be cyclized in the presence of the enamine derivative of the formula XIX in an inert solvent to give the urecil derivative of the formula XX, the reaction of the iso(thio)cyanate of the formula XVIII advantageously being carried out in the presence of 0.1–1.5 equivalents of a base such as, for example, sodium hydride, potassium tert-butoxide or alkaline earth metal oxide or alkaline earth metal hydroxide, for example barium hydroxide. The desired compounds of the formula $I_e$ can be obtained by standard processes by converting the uracils of the formula XX in the presence of an inert solvent and at least 1 equivalent of a base, for example alkali metal carbonate, e.g. potassium carbonate, c) with an alkylating agent of the formula XXI to give the N-alkyl derivative of the formula $I_e$ ($R_{14}$ alkyl), or d) by a method similar to WO 97/05116 with a hydroxylamine derivative of the formula XXII, in which $L_1$ is a leaving group, such as, for example, $HOS(O)_2O-$,

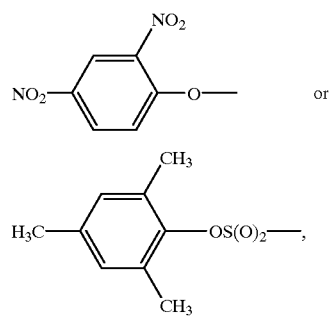

for example 2,4-dinitrophenyl-hydroxylamine or hydroxylamine-O-sulfonic acid, to give the N-amino derivative of the formula $I_e$ ($R_{14}$ amino). The thiono derivatives of the formula $I_e$ ($X_3$, $X_4$ sulfur) can be obtained by means of thionation, for example with phosphorus pentasulfide or Lawesson reagent.

The preparation of the compounds of the formula $I_f$

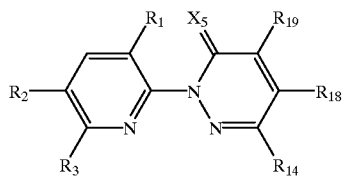

(1f)

in which $R_1$, $R_2$, $R_3$, $R_{17}$, $R_{18}$, $R_{19}$ and $X_5$ have the meanings given under formula I and $R_3$ is additionally hydrogen is illustrated in reaction scheme 5 which follows.

scheme 5 by reacting a 2-halopyridine derivative of the formula XIV with hydrazine, preferably in a protic solvent such as, for example, alcohols, by a method similar to GB-A-2 230 261 to give the 2-hydrazino derivative of the formula XXIII. The latter is reacted with a diketone of the formula XXIV by a method similar to DE-OS-19 754 348 or a dihaloketone of the formula XXIVa by a method similar to WO 97/07104 to give the hydrazone derivative of the formula XXV. The subsequent cyclization which yields the desired compound of the formula $I_f$ is carried out in the presence of the phosphorane derivative of the formula XXVII, if appropriate in the presence of a base, for example 4-dimethylaminopyridine. In the event that, in the compound of the formula $I_f$, $X_5$ is O, the product may subsequently be thionized by a method similar to what has been described under reaction scheme 4 ($X_5$ S). In accordance Reaction scheme 5:

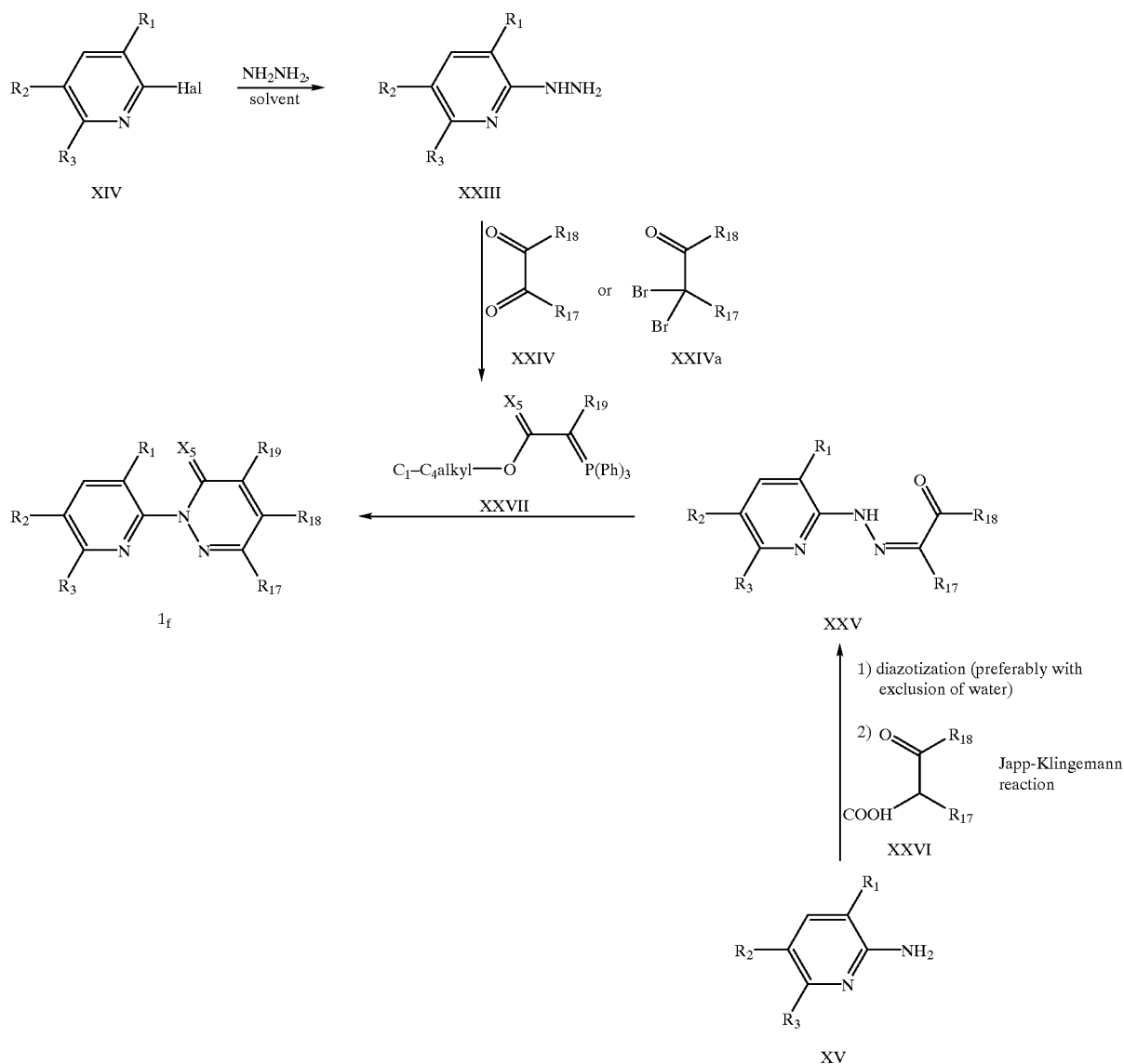

The compounds of the formula $I_f$ can be prepared by known methods, for example in accordance with reaction with reaction scheme 5, the hydrazone derivative of the formula XXV may also be obtained via diazotization, preferably with exclusion of water, and subsequent coupling with the keto acid of the formula XXVI (Japp-Klingemann reaction, similar to DE-OS-19 754 348), starting from the 2-aminopyridine derivative of the formula XV.

The preparation of the compounds of the formula $I_g$

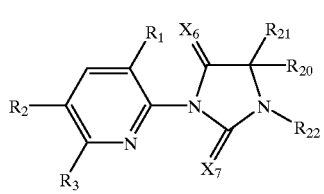

(1$_g$)

in which $R_1$, $R_2$, $R_3$, $R_{20}$, $R_{21}$, $R_{22}$, $X_6$ and $X_7$ have the meanings given under formula I and $R_3$ is additionally hydrogen is illustrated in reaction scheme 6 which follows.

The compounds of the formula $I_g$ can be prepared similarly to known methods such as described, for example, in EP-A-0 272 594, EP-A-0 493 323, DE-A-3 643 748, WO 95/23509, U.S. Pat. Nos. 5,665,681 or 5,661,109. In accordance with reaction scheme 6, for example, either
  a) a carbamate derivative of the formula XVIIa in the presence of a solvent and of a base or
  b) an iso(thio)cyanate of the formula XVIIa, if appropriate in a suitable solvent,
may be cyclized with an amino acid derivative of the formula XXVIII via the compound of the formula XXIX in the presence of a base and of a suitable solvent to give the compound of the formula $I_g$. In the event that, in the compound of the formula $I_g$, $R_{22}$ is hydrogen and $X_6$ and/or $X_7$ are oxygen, the product can, if appropriate, be subsequently alkylated with an alkylating agent of the formula XXX on the free N atom of the hydantoin ring and the ring carbonyl group can be thionated ($X_6$ and/or $X_7$ sulfur). In the starting compounds of the formulae XVIIa and XVIIIa in reaction scheme 6, $R_3$ may also be hydrogen. Functionalization in accordance with the definition of the substituent $R_3$ in the compounds of the formula $I_g$ may then be carried out by processes similar to those given in reaction schemes 1 to 3.

Reaction scheme 6:

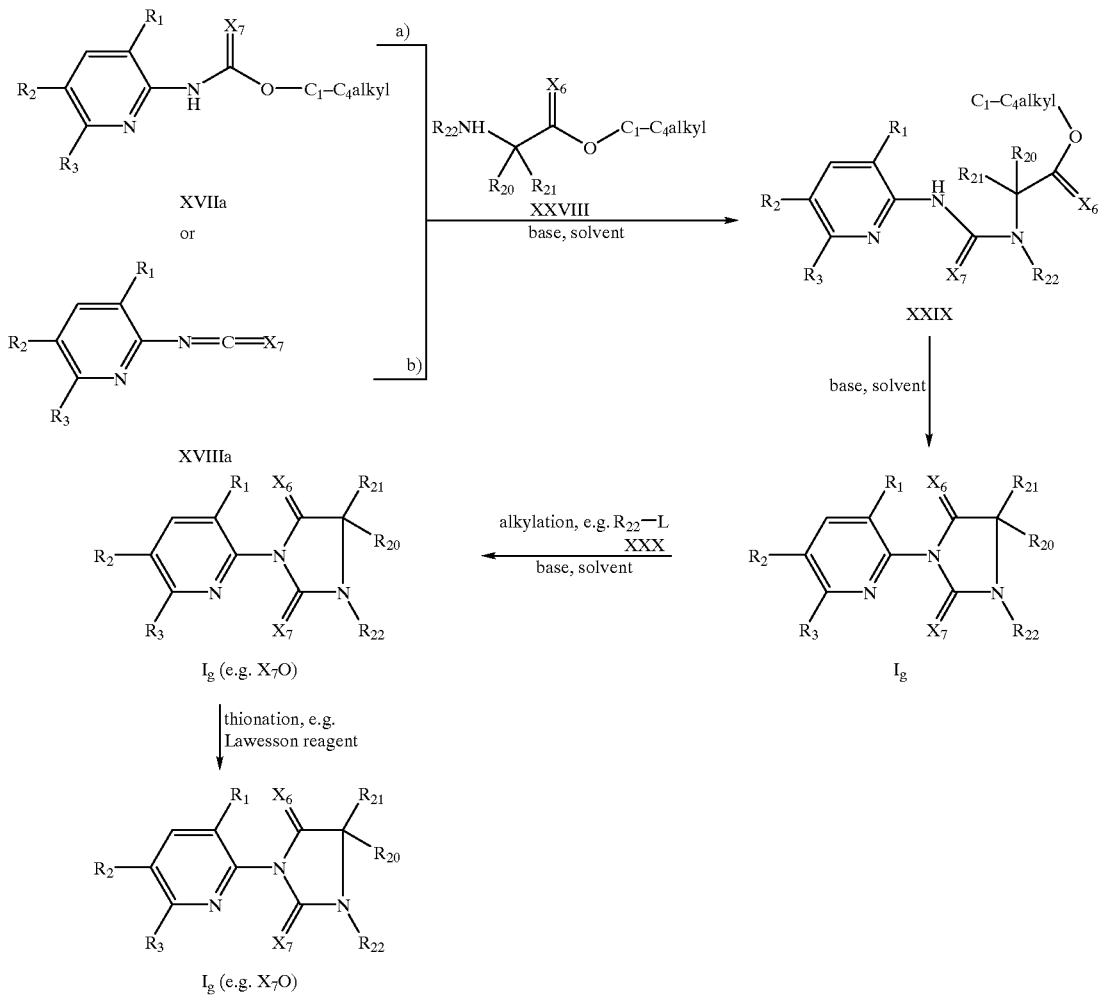

The preparation of the compounds of the formula $I_h$

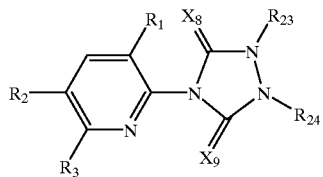

(1$_h$)

in which $R_1$, $R_2$, $R_3$, $R_{23}$, $R_{24}$, $X_8$ and $X_a$ have the meanings given under formula I and $R_3$ is additionally hydrogen is illustrated in reaction scheme 7 which follows.

may be cyclized with a carbazate of the formula XXXI via the compound of the formula XXXII in the presence of a base and of a suitable solvent to give the compound of the formula $I_h$. In the event that, in the compound of the formula $I_h$, $R_{23}$ and/or $R_{24}$ are hydrogen and $X_8$ and/or $X_9$ are oxygen, the product can subsequently be alkylated with an alkylating reagent of the formula XXXIIIa or XXXIIIb on the free N-atoms and the ring carbonyl group can be thionated with the thionating reagent ($X_8$ and/or $X_9$ sulfur). To prepare compounds of the formula $I_h$ in reaction scheme 7 in which $R_{23}$ and $R_{24}$ together form an alkylene bridge which is interrupted by, for example, —C(O)— or —S(O)$_2$—, for example the compound of the formula $I_h$, in which $R_{23}$ and $R_{24}$ are hydrogen can be reacted with a suitable Michael acceptor, such as, for example, $CH_2=CH—C(O)CH_3$, $CH_2=CH—S(O)_2CH_3$ or Reaction scheme 7:

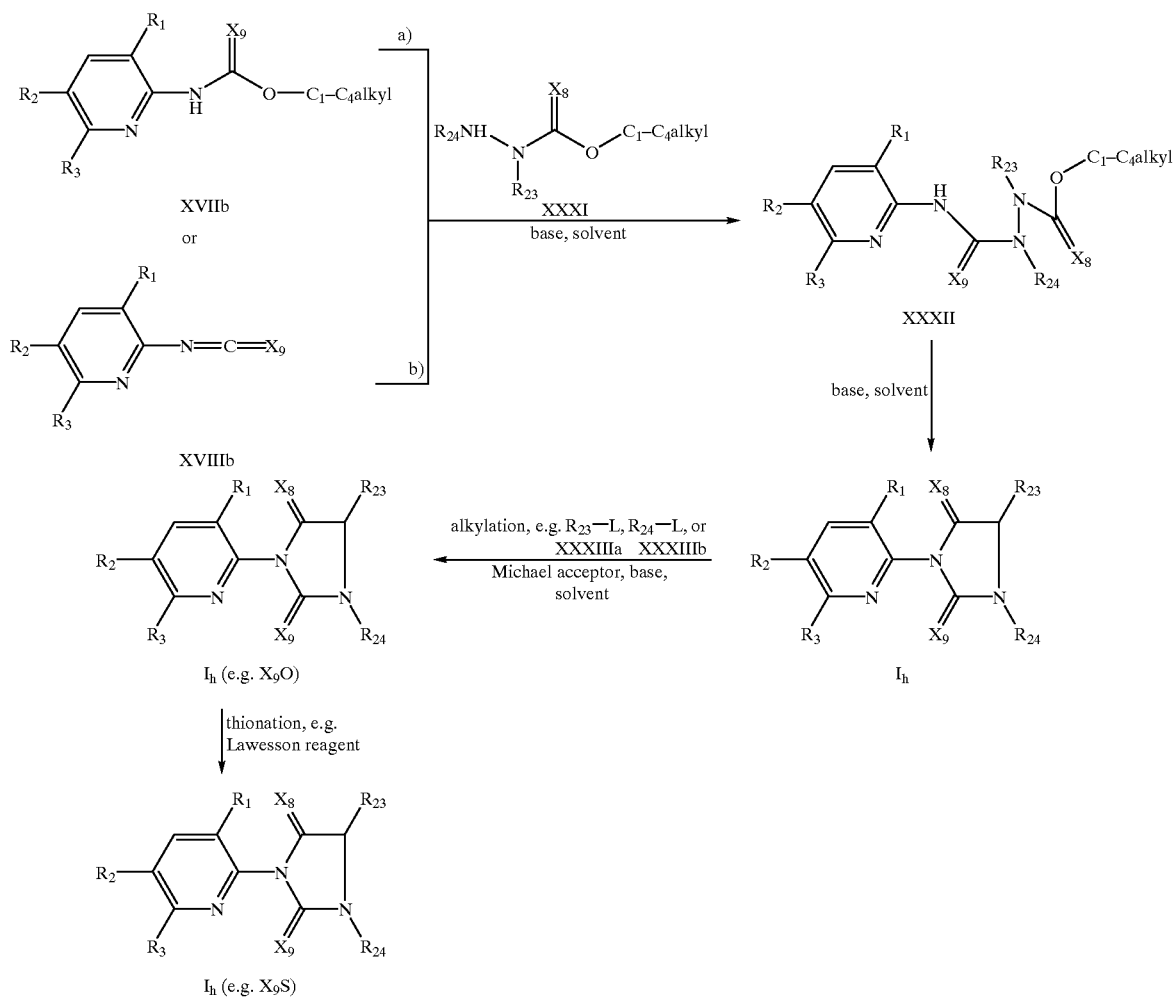

The compounds of the formula $I_h$ can be prepared similarly to known processes such as described, for example, in EP-A-0 210 137, DE-OS-2 526 358, EP-A-0 075 267 or EP-A-0 370 955. In accordance with reaction scheme 7, for example, either
a) a carbamate derivative of the formula XVIIb in the presence of a solvent and of a base, or
b) an iso(thio)cyanate of the formula XVIIIb, if appropriate in a suitable solvent, $CH_2=CH—S(O)_2—CH=CH_2$ and the resulting Michael adducts can be functionalized further.

The compounds of the formulae $I_e$, $I_f$, $I_g$ and $I_h$ in the preceding reaction schemes 4 to 7 in which $X_4$, $X_5$, $X_7$ and $X_9$ are O and $R_3$ is hydrogen can subsequently be functionalized, for example as shown in reaction schemes 1 to 3, to give the compounds of the formulae $I_e$, $I_f$, $I_g$ and $I_h$ in which $R_3$ has the meaning given under formula I.

In accordance with reaction scheme 8 which follows, the compounds of the formula I may also be obtained expediently directly by substituting a 2-halopyridine of the formula XIV or XIVa ($R_2$=CN) with the desired heterocycles $W_{01}$ to $W_{04}$ or salts thereof (for example alkali metal salts), if appropriate in the presence of a suitable solvent and of a base (variant a)). Similar reactions are described, for example, in J. Het. Chem. 15, (1978), 1221. In some cases it may be expedient to couple the heterocyclic group $W_1$ to $W_4$, for example as shown in variant b) in reaction scheme 8 with reference to $W_1$, to the pyridyl moiety by means of direct alkylation with an imino-ether-modified heterocycle of the formula $W_{001}$.

Reaction scheme 8:

Variant a):

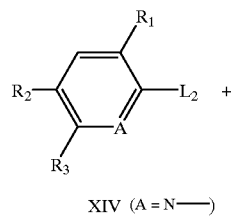 + 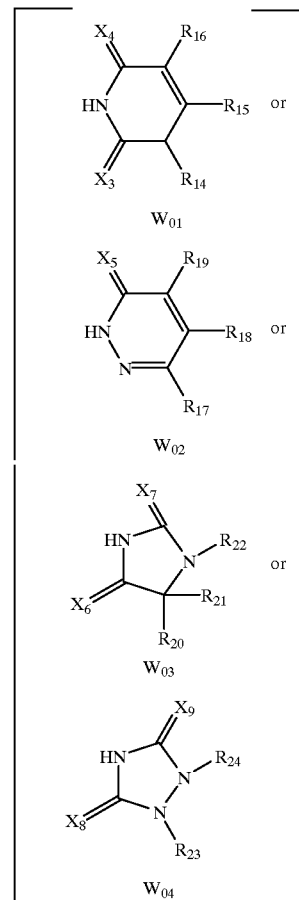 →(base, solvent) 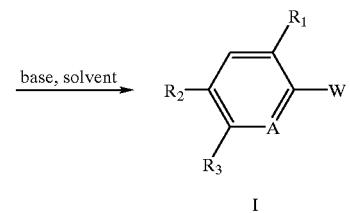

XIV (A = N—)

Variant b)

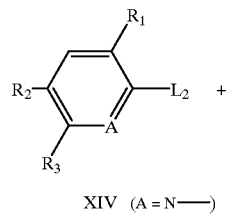 + 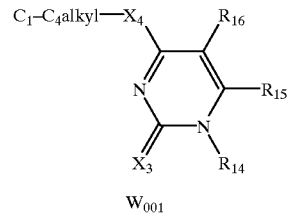 →(base, solvent) 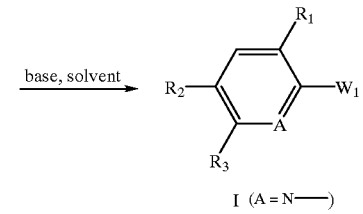

XIV (A = N—)     $W_{001}$     I (A = N—)

$L_2$ in the compound of the formula XIV in reaction scheme 8 is a leaving group such as, for example, halogen or a $C_1$–$C_4$alkyl or phenyl-sulfonyl group.

The heterocyles of formula $W_{01}$ in reaction scheme 8 above, wherein $R_{14}$ is $C_1$–$C_3$alkyl (e.g. methyl), $R_{15}$ is $C_1$–$C_3$haloalkyl (e.g. $CF_3$), $R_{16}$ is hydrogen and $X_3$ and $X_4$ are oxygen, are obtained either according to WO 98/08824 or by the reaction sequence as follows:

An enamine derivative of formula XXXIV

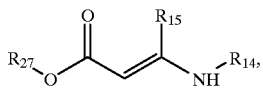

(XXXIV)

wherein $R_{14}$ is $C_1$–$C_3$alkyl, $R_{15}$ is $C_1$–$C_3$haloalkyl and $R_{27}$ is $C_1$–$C_4$alkyl, $C_1$- or $C_2$haloalkyl or optionally substituted benzyl, is converted in the presence of chlorocarbonyl isocyanate (CICONCO) in inert organic solvents to the compound of formula XXXV

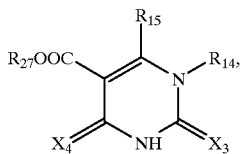

(XXXV)

the ester function of which is then transferred to the corresponding carboxylic acid function as represented by compound of formula XXXVI

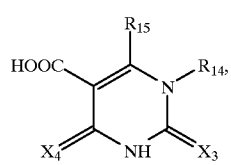

(XXXVI)

which then is decarboxylated to yield the compound of formula $W_{01}$

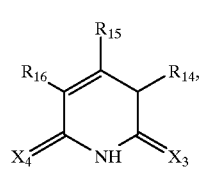

($W_{01}$)

the radicals $R_{14}$, $R_{15}$, $R_{27}$, $X_3$, $X_4$ and $R_{16}$ in the compounds of formulae XXXV, XXXVI and $W_{01}$, having the abovementioned meaning. This reaction sequence is novel and therefore instant invention also relates to this method of preparation.

Above reaction sequence is illustrated in reaction scheme 9 which follows.

Reaction scheme 9:

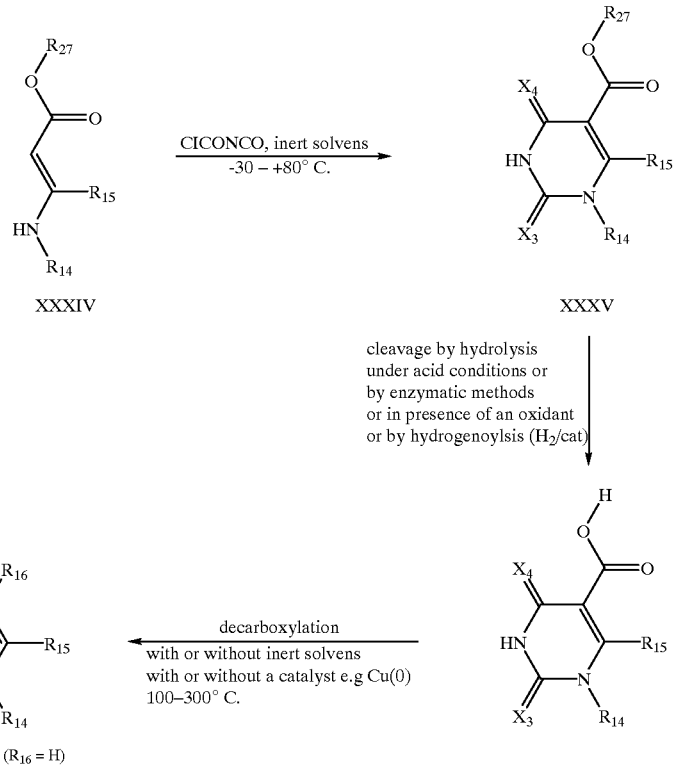

According to reaction scheme 9 above the enamine derivative of formula XXXIV, wherein $R_{14}$ and $R_{15}$ are as defined and $R_{27}$ is $C_1$–$C_4$alkyl (e.g. t-butyl), $C_1$–$C_2$haloalkyl (e.g. 2,2,2-trichloroethyl) or optionally substituted benzyl (e.g. p-methoxybenzyl) is reacted with chlorocarbonyl isocyanate (CICONCO) in inert sovents such as dichloromethane at temperatures in the range of from −30° C. to +8° C. to obtain the pyrimidine derivative of formula XXXV. The carboxylic ester function $COOR_{27}$ of compound of formula XXXV is then cleaved for example by hydrolysis or hydrogenolysis to yield the corresponding carboxylic acid function of compound of formula XXXVI according to the following methods as described in 'Protective Groups in Organig Synthesis', Editor Th. Greene, New York, 1981; and Houben-Weyl, Band E5, 'Carbonsäuren und Carbonsäurederivate', Stuttgart, 1985:

- treatment with an acid (formic acid containing catalytic amounts of sulfuric acid as described in Houben-Weyl above, p. 227) if $R_{27}$ in compound of formula XXXV is alkyl or benzyl;
- treatment with formic acid, trifluoroacetic acid or HBr if $R_{27}$ in compound of formula XXXV is t-butyl or benzyl;
- treatment with tin (Zn) in acetic acid if $R_{27}$ in compound of formula XXXV is 2,2,2-trichloroethyl;
- treatment with an oxidant such as ceric ammonium nitrate in water/acetonitril if $R_{27}$ in compound of formula XXXV is 4-methoxybenzyl;
- cleavage by hydrogenolysis ($H_2$/appropriate catalyst such as Pd—C in inert solvent) if $R_{27}$ in compound of formula XXXV is benzyl or substituted benzyl;
- or by enzymatic cleavage (Ann. Rep. Med. Chem. 19, 263 (1984); Angew. 24, 617 (1985)).

Decarboxylation of the carboxylic acid derivative of formula XXXVI to the uracil compound of formula $W_{01}$, wherein $R_{16}$ is hydrogen is achieved finally by heating net or in inert solvents such as decaline or quinoline with or without additional catalysts such as Cu(O) or Cu(I)-salts such as CuCl.

The compounds of the formulae XIV, XIVa and XV which are not already known can be prepared by known methods such as described in, for example, DE-A-3 917 469; WO 97/07114; WO 92/00976; JP-A-58-213 776; EP-A-0 012 117; EP-A-0 306 547; EP-A-0 030 215; EP-A-0 272 824; EP-A-0 500 209; U.S. Pat. Nos. 4,996,323; 5,017,705; WO 97/05112; J. Het. Chem. 11 (1974), 889; J. Het. Chem 21 (1984), 97; Tetrahedron 41 (1985), 4057; Heterocycles 22,117; Synth. 1988, 938; J. Med. Chem. 25 (1982), 96, Chem. Pharm. Bull. 35 (1987), 2280 and WO 98/11071. The 2-aminopyridines of the formula XV can also be prepared from the corresponding pyridine derivatives which have carboxylic acid, carboxylic acid chloride, carboxylic acid azide, and carboxylic acid ester or carboxamide functions in the 2-position by Curtius, Hofmann or Lossen degradation reactions.

The reagents and starting compounds of the formulae V, VII, IX, IXa, X, Xa, XI, XII, XIIa, XIII, XIIIa, XVI, XVIIa, XVIIb, XVIIIa, XVIIIb, XIX, XXI, XXII, XXIV, XXIVa, XXVI, XXVII, XXVIII, XXX, XXXI, XXXIIIa, XXXIIIb and XXXIV which have been used in reaction schemes 1 to 9 are either known or can be prepared analogously to known processes.

The intermediates of the formulae III and IV

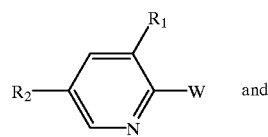

(III)

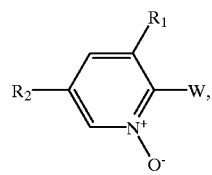

(IV)

in which $R_1$, $R_2$ and W have the meanings given under formula I, are novel. The invention thus also relates to these compounds.

The intermediates of the formula XVIIb

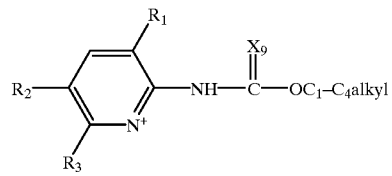

(XVIIb)

in which $R_1$, $R_2$, $R_3$ and $X_9$ have the meanings given under formula I and $R_3$ is additionally hydrogen are novel. The invention thus also relates to these compounds.

The reactions which give compounds of the formula I are advantageously carried out in aprotic, inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitrites such as acetonitrile or proprionitrile, amides such as N,N-dimethylformamide, N,N-diethylformamide or N-methylpyrrolidinone. The reaction temperatures are preferably between −20° C. and +120° C. In some cases, the reactions are slightly exothermic and, as a rule, they may be carried out at room temperature. To reduce the reaction time, or else to start up the reaction, the reaction mixture may be warmed briefly to boiling point, if appropriate. The reaction times may also be reduced by adding a few drops of base as reaction catalyst. Suitable bases are, in particular, tertiary amines such as trimethylamine, triethylamine, quinuclidine, 1,4-diazabicyclo-[2.2.2]-octane, 1,5-diazabicyclo-[4.3.0]-non-5-ene, 1,5-diazabicyclo-[5.4.0]-undec-7-ene or 4-dimethylaminopyridine. However, inorganic bases such as hydrides, e.g. sodium hydride or calcium hydride, hydroxides such as sodium hydroxide or potassium hydroxide, carbonates such as sodium carbonate or potassium carbonate, or hydrogen carbonates such as potassium hydrogen carbonate and sodium hydrogen carbonate, may also be used as bases.

The compounds of the formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons, or by means of column chromatography and a suitable eluent.

Suitable uses according to the invention of the compounds of the formula I or compositions comprising them are all application methods which are customary in agriculture such as, for example, pre-emergence application, post-emergence application and seed treatment, and a variety of methods and techniques, such as, for example, the controlled release of active ingredient. To this end, the dissolved active ingredient is applied to mineral granule carriers or to polymerized granules (urea/formaldehyde) and dried. If appropriate, an additional coating can be applied (coated granules) which allows controlled release of the active ingredient over a specific period.

The compounds of the formula I can be employed as herbicides as pure active ingredients, i.e. as obtained in synthesis. Preferably, however, they are processed in the customary manner with the auxiliaries conventionally used in the art of formulation, for example to give emulsifiable concentrates, directly sprayable or dilutable solutions, dilute emulsions, wettable powders, soluble powders, dusts, granules or microcapsules. Such formulations are described, for example, in WO 97/34485 on pages 9 to 13. The application methods, such as spraying, atomizing, dusting, wetting, scattering or pouring, and the nature of the compositions are chosen to suit the intended aims and prevailing circumstances.

The formulations, i.e. the compositions, preparations or combinations which comprise the active ingredient of the formula I or at least one active ingredient of the formula I and, as a rule, one or more solid or liquid formulation auxiliaries, are prepared in the known manner, for example by intimately mixing and/or grinding the active ingredients with the formulation auxiliaries such as, for example, solvents or solid carriers. Furthermore, surface-active compounds (surfactants) may additionally be used when preparing the formulations. Examples of solvents and solid carriers are given, for example, in WO 97/34485 on page 6.

Suitable surface-active compounds are, depending on the nature of the active ingredient of the formula I to be formulated, non-ionic, cationic and/or anionic surfactants and surfactant mixtures which have good emulsifying, dispersing and wetting properties.

Examples of suitable anionic, non-anionic and cationic surfactants are listed, for example, in WO 97/34485 on pages 7 and 8.

The surfactants conventionally used in the art of formulation described in, inter alia, "McCutcheon's Detergents and Emulsifiers Annual" MC Publishing Corp., Ridgewood N.J., 1981, Stache, H., "Tensid-Taschenbuch" [Surfactants Guide], Carl Hanser Verlag, Munic/Vienna, 1981, and M. and J. Ash, "Encyclopedia of Surfactants", Vol I–III, Chemical Publishing Co., New York, 1980–81 are furthermore also suitable for preparing the herbicidal compositions according to the invention.

As a rule, the herbicidal formulations comprise 0.1 to 99% by weight, in particular 0.1 to 95% by weight, of herbicide, 1 to 99.9% by weight, in particular 5 to 99.8% by weight, of a solid or liquid formulation auxiliary and 0 to 25% by weight, in particular 0.1 to 25% by weight, of a surfactant. While concentrated compositions are more preferred as commercially available goods, the end user uses, as a rule, dilute compositions. The compositions may also comprise other additives such as stabilizers, e.g. epoxidized or unepoxidized vegetable oils (epoxidized coconut oil, rapeseed oil or soya oil), antifoams, e.g. silicone oil, preservatives, viscosity regulators, binders, tackifiers and fertilizers or other active ingredients.

As a rule, the active ingredients of the formula I are applied to the plant or its environment at application rates of 0.001 to 4 kg/ha, in particular 0.005 to 2 kg/ha. The dosage required for the desired action can be determined by experiments. It depends on the type of action, the developmental stage of the crop plant and of the weed, and on the application (location, timing, method) and, due to these parameters, may vary within wide ranges.

The compounds of the formula I are distinguished by herbicidal and growth-inhibitory properties which allow them to be used in crops of useful plants, in particular in cereals, cotton, soya, sugar beet, sugar cane, plantation crops, oilseed rape, maize and rice and for non-selective weed control. Crops are also to be understood as meaning those which have been made tolerant to herbicides, or classes of herbicides, by conventional breeding or genetic engineering methods. The weeds to be controlled may be monocotyledonous or dicotyledonous weeds such as, for example, Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, lpomoea, Chrysanthemum, Galium, Viola and Veronica.

The examples which follow illustrate the invention in greater detail without imposing any limitation.

PREPARATION EXAMPLES

Example H1

Preparation of 2-N-ethoxicarbonylamino-3-fluoro-5-chloropyridine

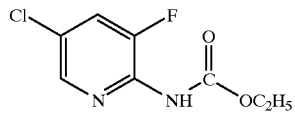

294 g of 2-amino-3-fluoro-5-chloropyridine are dissolved in 1 l of dry pyridine, the solution is cooled to 0° C., 220 g of ethyl chloroformate are added dropwise with stirring, and the mixture is stirred at 22° C. until the reaction is complete. The reaction mixture is then poured into ice-water, brought to pH 4–5 using 2N hydrochloric acid and extracted with ethyl acetate. The combined extracts are washed with water, dried over sodium sulfate, evaporated and crystallized by adding n-hexane. The resulting precipitate is filtered off, washed with n-hexane and dried in vacuo. This gives the desired title compound of m.p. 132° C.

Example H2

Preparation of 1-(3-fluoro-5-chloropyridine-2-yl)-3-methyl-4-trifluoromethyl-pyrimidine-2.6-dione

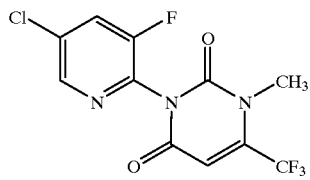

(compd. no. 600.001)

A solution of 22.7 g of ethyl 4,4,4-trifluoro-3-amino-2-butenoate is added dropwise with stirring and cooling at 0–5° C. under a nitrogen atmosphere to 5.1 g of a previously introduced sodium hydride dispersion (60%) in 60 ml of n-methylpyrrolidine, and stirring is continued at 22° C. until the evolution of hydrogen has ceased. Then, 23.7 g of 2-ethoxycarbonylamino-3-fluoro-5-chloropyridine (Example H1) are added and the reaction mixture is heated for approx. 5 hours at 120° C. It is then cooled, 16.7 9 of methyl iodide are added dropwise, and stirring is continued overnight at 22° C. After the reaction mixture has been taken up in ethyl acetate, it is washed with ice-water, dried over sodium sulfate, filtered and evaporated. The residue obtained is recrystallized from ethyl acetate/n-hexane. This gives the desired title compound of m.p. 133–134° C.

Example H3

Preparation of 1-(3-fluoro-5-chloro-2-pyridyl-N-oxide)-3-methyl-4-trifluoromethyl-pyrimidine-2.6-dione

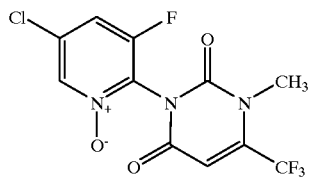

(compd. no. 617.001)

24 g of 1-(3-fluoro-5-chloropyridine-2-y)-3-methyl-4-trifluoromethylpyrimidine-2,6-dione (Example H2) in 150 ml of dichloromethane is cooled to −5° C. and treated with 2 g of hydrogen peroxide/urea adduct. 2.7 ml of trifluoroacetic anhydride, dissolved in 2 ml of dichloromethane, are subsequently metered in and, when the exothermal reaction has subsided, the reaction mixture is stirred overnight. Then, again, 3 ml of trifluoroacetic anhydride and 5 g of hydrogen peroxide/urea adduct are added in two portions in the course of 3 hours and, when the exothermal reaction has subsided, the reaction mixture is heated at 25–35° C. until the reaction is complete. It is subsequently cooled and, at −5° C., brought to pH 7.5, first with 2 N sodium hydroxide solution and then with saturated sodium hydrogen carbonate solution, the mixture is partitioned between dichloromethane and ice-water, and the organic phase which has been separated off is dried over sodium sulfate, filtered and concentrated by evaporation. The solid residue which remains is recrystallized from ethyl acetate/n-hexane. This gives the desired product of m.p. 142–143° C.

Example H4

Preparation of 1-(3-fluoro-5,6-dichloro-2-pyridyl)-3-methyl-4-trifluoromethyl-pyrimidine-2,6-dione

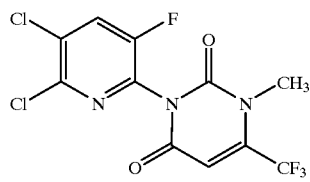

(compd. no. 1.396)

A solution of 2.4 ml of phosphorus oxytrichloride in 20 ml of 1,2-dichloroethane, heated at 70° C., is treated with 6.8 g of 1-(3-fluoro-5-chloro-2-pyridyl-N-oxide)-3-methyl-4-trifluoromethyl-pyrimidine-2,6-dione (Example H3), a little at a time, and kept overnight at this temperature, a further 4.0 ml of phosphorus oxytrichloride are added, and the mixture is heated for a further 20 hours. It is subsequently cooled, poured into ice-water and extracted with dichloroethane, and the combined extracts are washed with ice-cooled 2N sodium hydroxide solution and water, dried over sodium sulfate and concentrated by evaporation. The residue is purified by silica gel chromatography (eluent:hexane/ethyl acetate 9/1). This gives the desired title compound of m.p. 113–115° C.

Example H5

Preparation of 1-(2-hydroxy-3-chloro-5-fluoropyridine-6-yl)-3-methyl-4-trifluoromethylpyrimidine-2,6-dione and 1-(3-hydroxy-2-chloro-5-fluoropyridine-6-yl)-3-methyl-4-trifluoromethylpyrimidine-2,6-dione

 and (compd. no. 1002)

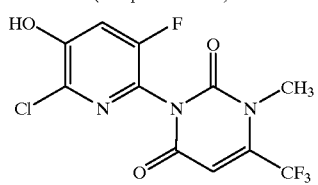

A solution of 29.6 g of 1-(3-fluoro-5-chloro-2-pyridyl-N-oxide)-3-methyl-4-trifluoromethyl-pyrimidine-2,6-dione (Example H3) in 400 ml of dimethylformamide, cooled to −30° C., is treated dropwise with 182 g of trifluoroacetic anhydride, stirred overnight at −30° C. and the next day at 22° C. Then, the mixture is freed from excess trifluoroacetic anhydride in vacuo, cooled to −5° C. and carefully neutralized, first with dilute sodium hydroxide solution and then with sodium hydrogen carbonate solution. After addition of ice-water, the mixture is extracted with ethyl acetate, and the combined extracts are washed with water and dried over sodium sulfate. The mixture is then filtered, the filtrate is concentrated by evaporation and the residue obtained is purified over a silica gel column (eluent: n-hexane/ethyl acetate 8/2, increasing ethyl acetate gradient). This gives the desired title compound (compd. no. 1.002) of m.p. 200–202° C. Besides that, a mixed fraction is obtained which, in addition to 1-(2-hydroxy-3-chloro-5-fluoro-pyridine-6-yl)-3-methyl-4-trifluoromethylpyrimidine-2,6-dione, furthermore also contains the isomer 1-(3-hydroxy-2-chloro-5-fluoropyridine-6-yl)-3-methyl-4-trifluoromethylpyrimidine-2,6-dione. The latter isomeric compound is obtained by a further rearrangement. The ratio of the two isomers 1-(2-hydroxy-3-chloro-5-fluoropyridine-6-yl)-3-methyl-4-trifluoromethylpyrimidine-2,6-dione and 1-(3-hydroxy-2-chloro-5-fluoropyridine-6-yl)-3-methyl-4-trifluoromethypyrimidine-2,6-dione varies, depending on the reaction conditions (approx. 3:1). The isomer mixture of the mixed fraction can either be used directly in the next reaction step or separated by means of HPLC (Li-Chrospher Si60; eluent: ethyl acetate/hexane 15/85 to 30/70, increasing ethyl acetate gradient). This gives pure 1-(3-hydroxy-2-chloro-5-fluoropyridine-6-yl)-3-methyl-4-trifluoromethylpyrimidine-2,6-dione of m.p. 189–192° C.

Example H6

Preparation of 1-(2-propargyloxy-3-chloro-5-fluoropyridine-6-yl)-3-methyl-4-trifluoromethylpyrimidine-2,6-dione, 1-(2-chloro-3-proparagyloxy-5-fluoropyridine-6-yl)-3-methyl-4-trifluoromethylpyrimidine-2,6-dione and 1-(1-propargyloxy-3-chloro-5-fluoro-2-pyridon-6-yl)-3-methyl-4-trifluoromethylpyrimidine-2,6-dione

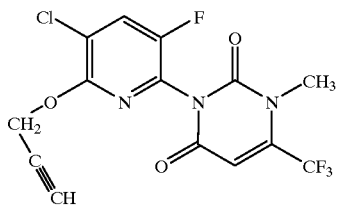

(compd. no. 1.022)

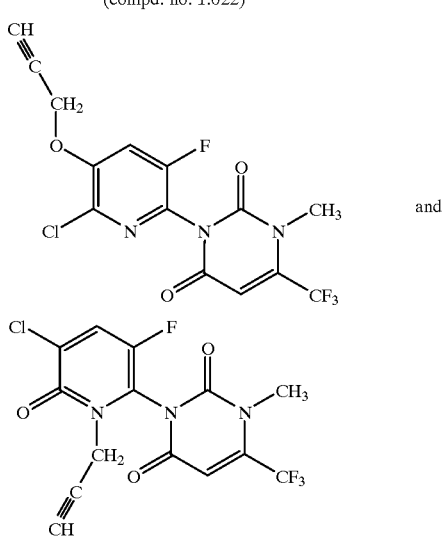

and

A suspension of 10.2 g of a mixture of 1-(2-hydroxy-3-chloro-5-fluoropyridine-6-yl)-3-methyl-4-trifluoromethylpyrimidine-2,6-dione and 1-(2-chloro-3-hydroxy-5-fluoropyridine-6-yl)-3-methyl-4-trifluoromethylpyrimidine-2,6-dione (Example H5), 7.5 g of potassium carbonate and 0.08 g of 18-crown-6 in 180 ml of acetonitrile is treated dropwise with 4.5 ml of propargyl bromide and subsequently heated overnight at 65° C. The mixture is then concentrated by evaporation in vacuo, the residue obtained is treated with ethyl acetate/ice-water mixture and 1 N hydrochloric acid until the pH is 7, the aqueous phase is separated off and extracted with ethyl acetate, and the combined organic phases are washed with water, dried over sodium sulfate and filtered, and the filtrate is concentrated by evaporation. The residue is purified by means of silica gel chromatography (eluent: n-hexane/ethyl acetate 8/2). This gives the desired isomers 1-(2-propargyloxy-3-chloro-5-fluoropyridine-6-yl)-3-methyl-4-trifluoromethylpyrimidine-2,6-dione, m.p. 121–122° C. (compd.no.1.022), 1-(2-chloro-3-propargyloxy-5-fluoropyridine-6-yl)-3-methyl-4-trifluoromethylpyrimidine-2,6-dione, m.p, 69–71° C. and 1-(1-propargyloxy-3-chloro-5-fluoro-2-pyridon-6-yl)-3-methyl-4-trifluoromethylpyrimidine-2,6-dione, m.p. 223–224° C.

Example H7

Preparation of tetrahydroimidazoro[1,5-a]pyridine-1,3-dione

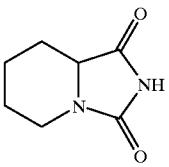

34.6 g (0.193 mol) of methyl 2-piperidinecarboxylate-hydrochloride are introduced into 260 ml of water in a reaction vessel and 17.4 g (0.216 mol) of potassium cyanate are added. 30 ml of glacial acetic acid are then added, and the homogenous solution formed is stirred for 4.5 hours at 22° C. The reaction solution is subsequently saturated with sodium chloride (NaCl) and extracted twice using in each case 200 ml of tert-butyl methyl ether. The organic fractions are combined, dried over sodium sulfate and concentrated. 11 g of a viscous oil, from which crystals separate out overnight, is obtained as residue. The crystals are separated off by decanting off the remaining oil and purified by triturating (digesting) with diethyl ether. This gives the desired product of m.p. 122–123° C. in a yield of 5.75 g.

Example H8

Preparation of 2-(3-fluoro-6-chloro-5-cyano-2-pyridyl)tetrahydroimidazo[1,5-a]pyridine-1,3-dione

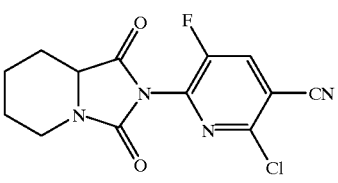

(compd. no. 81.396)

0.77 g (0.005 mol) of the hydantoin derivative of Example H7 is introduced into 50 ml of acetonitrile in a reaction vessel. This solution is treated in succession with 0.95 g (0.00688 mol) of finely pulverulent potassium carbonate and 0.96 g (0.00503 mol) of 2,6-dichloro-3-cyano-4-fluoropyridine and heated for 5 hours to reflux temperature, with stirring. After this time, starting material can no longer be detected (TLC analysis). The reaction mixture is cooled and filtered, and the solvent is evaporated. The resulting dark brown viscous oil is chromatographed over a silica gel column (30 g) under pressure (eluent: hexane/ethyl acetate 2/1). The product-containing fractions which have an $R_f$ value 0.26 are combined and freed from solvent. This gives the desired product as white crystals of m.p. 192–193° C. MS (FD): [M$^+$, 40%] 308.

Example H9

Preparation of 2-(3-fluoro-5-cyano-6-methoxy-2-pyridyl)tetrahydroimidazo[1,5-a]pyridine-1,3-dione

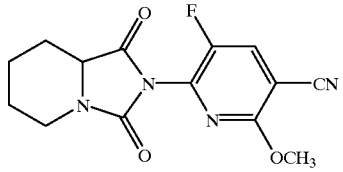

(comod. no. 81.016)

0.85 g (0.00275 mol) of the compound of Example H8 is dissolved in 50 ml of dry acetonitrile and 0.56 ml (0.003 mol) of sodium methoxide (5.4 molar in methanol) is added. This reaction mixture is heated to boiling point and kept at reflux temperature for 2.5 hours. During this process, the reaction mixture slowly turns cloudy and a solid precipitate separates out. According to TLC analysis, less than 10% starting material is still present. After the reaction mixture has been cooled, filtered and concentrated, 0.8 g of a viscous oil remains, and this is treated with 50 ml of water and extracted twice using in each case 50 ml of dichloromethane. The combined organic phases are dried over sodium sulfate and concentrated, and the residue obtained is digested in diethyl ether. This gives the desired target compound as pale yellow crystals of m.p. 159–170° C.

Example H10

Preparation of 2-(5-chloro-3-fluoropyridin-2-yl)-7-hydroxytetrahydroimidazo[1,5-a]-pyridine-1,3-dione

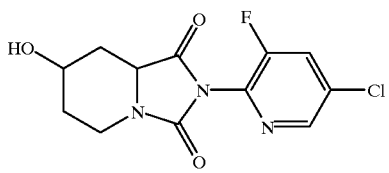

(comod. no. 604.001)

A reaction mixture composed of 100 ml of dioxane, 50 ml of N,N-dimethylformamide, 8 ml of propylene oxide, 6 ml of 1.8-diazabicyclo-[5.4.0]undec-7-ene and 8.0 g of ethyl 4-hydroxypiperidine-2-carboxylate•hydrochloride is stirred overnight at 20° C. 4.4 g of potassium tert-butoxide and 50 ml of N,N-dimethylformamide are subsequently added, and the resulting suspension is heated for approx. 4 hours at 95° C. The reaction mixture is subsequently cooled, brought to pH 6.5 to 7.0 with cold aqueous 2N hydrochloric acid solution and extracted with ethyl acetate. The combined extracts are washed with sodium chloride solution and water and concentrated by evaporation, and the solid residue is purified by means of silica gel chromatography (eluent: hexane/ethyl acetate). This gives the title compound as a mixture of two diastereomers of m.p. 183–185° C. and 184–186° C., which can be resolved.

Example H11

Preparation of 2-(5-chloro-3-fluoropyridin-2-yl)-7-fluorotetrahydroimidazo-[1,5-a]-pyridine-1,3-dione

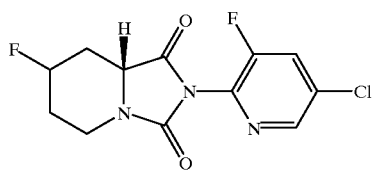

2.6 g of 2-(5-chloro-3-fluoro-pyridin-2-yl)-7-hydroxitetrahydroimidazo-[1,5-a]-pyridin-1,3-dione (isomer B, Example H10) in 80 ml dichloromethane is treated at –55° C. to –65° C. with 1.9 ml of diethylamino-sulfur trifluoride (DAST) and stirred at the same temperature for 1 hour. The reaction mixture is then allowed to stir at 20° C. over night. The resulting brownish solution is treated with ice and water and extracted with ethyl acetate. The combined extracts are washed with water, dried, filtered through a small silicagel column and evaporated to give the desired product with m.p. 154–157° C.

Example H12

Preparation of 1-(3-fluoro-5-cyano-6-chloro-2-pyridyl)-3-methyl-4-trifluoromethyl-pyrimidin-2,6-dione

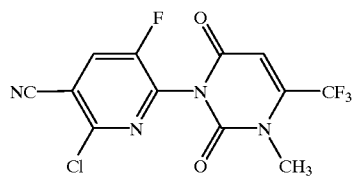

(compd. no. 3.396)

A mixture of 0.776 g 1-methyl-6-trifluoromethyl-2,4-(1H,3H)-pyrimidin-dione, 0.760 g potassium carbonate and 0.768 g 2,6-dichloro-3-fluoro-5-cyanopyridin in 40 ml dimethylsulfoxide is stirred under nitrogen at 130° C. until conversion is complete. Then the reaction mixture is cooled down and diluted with ice and water. The pH of the mixture is adjusted to neutral and the mixture is extracted several times with ethyl acetate. The organic layers are washed with water, dried, evaporated and the residue is purified by silicagel chromatography (hexane/ethyl acetate 7/3) to yield the title compound as a solid of m.p. 146–148° C.

Example H13

Preparation of 1-methyl-6-trifluoromethyl-2,4-(1H,3H)-pyrimidin-dione

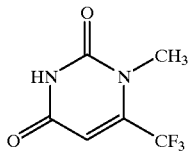

Intermediate a): Preparation of 3-methylamino-4,4,4-trifluoromethyl-2-butenoic acid benzylester

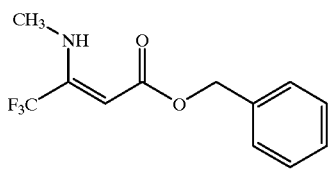

A mixture of 6.15 g 4,4,4-trifluoroaceto acetic acid benzylester and 4.6 g methylamine-hydrogene acetate in 250 ml cyclohexane is heated under nitrogen at reflux temperature for 2.5 hours. Water formed is absorbed in a column packed with molecular sieves A4. The vessel is then cooled down, and the mixture is filtered through silicagel and the filtrate evaporated to give the desired enamine as yellowish oil. $^1$H-NMR (CDCl$_3$): 8.18 ppm (broad signal, 1H); 7.35 ppm (m, 5H); 5.15 ppm (m, 3H); 2.95 ppm (m, 3H).

Intermediate b): Preparation of 1-methyl-5-benzyloxycarbonyl-6-trifluoromethyl-2,4-(1H,3H)-pyrimidin-dione

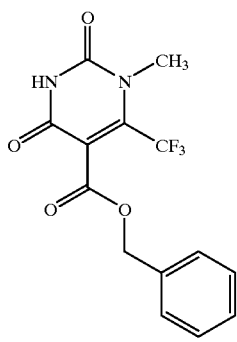

A solution of 5.7 g 3-methylamino-4,4,4-trifluoromethyl-2-butenoic acid benzylester in 120 ml dichloromethane is treated at 20° C. with a solution of 1.95 g chlorocarbonyl-isocyanate in 5 ml of dichloromethane and stirred over night. Hydrogen chloride is splitted off during the reaction. The reaction is cooled down in an ice bath, neutralised with sodium hydrogencarbonate, washed with water and dried. After evaporation, the residue is filtered through a short column packed with silicagel (hexane/ethyl acetate 7/3). Evaporation of the eluate gives the desired product of m.p. 132–134° C. Starting with 3-methylamino-4,4,4-trifuoromethyl-2-butenoic acid ethylester as the enamine leads to the corresponding 1-methyl-5-ethyoxycarbonyl-6-trifluoromethyl-2,4-(1H,3H)-pyrimidin-dione with a m.p. of 131–133° C.

Intermediate c): Preparation of 1-methyl-5-carboxy-6-trifluoromethyl-2,4-(1H,3H)-pyrimidin-dione

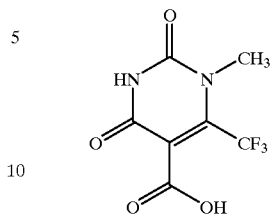

A solution of 5.5 g 1-methyl-5-benzyloxycarbonyl-6-trifluormethyl-2,4-(1H,3H)-pyrimidin-dione in 150 ml tetrahydrofurane is hydrogenated at 20° C. over 0.560 g of Pd—C (5%). Then the reaction mixture is filtrated and the filtrate evaporated to dryness. The resulting desired carboxylic acid has a m.p. of 216° C. (under decomposition).

Preparation of 1-methyl-6-trifluoromethyl-2,4-(1H,3H)-pyrimidin-dione: 2,61 g 1-methyl-5-carboxy-6-trifluoromethyl-2,4-(1H,3H)-pyrimidin-dione is heated under nitrogen at 220° C. until decarboxylation has ceased. After cooling, the title compound with m.p. 140–142° C. is obtained.

The preferred compounds given in Tables 1 to 194 below in which the substituents $R_1$ and $R_3$ are defined as shown in Table A and in Tables 500 to 512 in which the substituents $R_1$ and $R_2$ are defined as shown in Table B and in Tables 600 to 638 (intermediates with variable substituents $R_1$ and $R_2$ as shown in Tables C and D) can also be prepared in a similar manner and by methods as they are shown in the general reaction schemes 1–9 and in the references indicated.

Table 1: A preferred group of compounds of the formula I has the formula

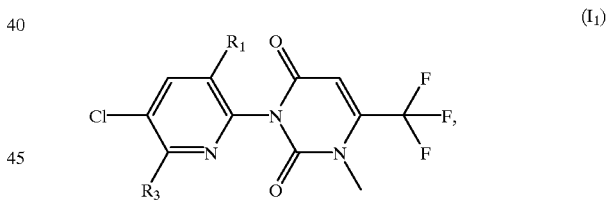

(I$_1$)

where the meanings of the respective substituents $R_1$ and $R_3$ are given in Table A, thus disclosing 412 specific compounds of the formula I$_1$.

Table 2: A further preferred group of compounds of the formula I has the formula

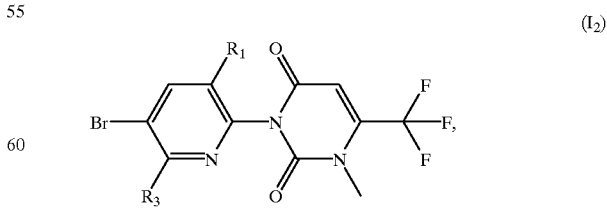

(I$_2$)

where the meanings of the respective substituents $R_1$ and $R_3$ are given in Table A, thus disclosing 412 specific compounds of the formula I$_2$.

Table 3: A further preferred group of compounds of the formula I has the formula

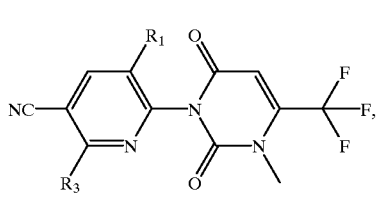
($I_3$)

where the meanings of the respective substituents $R_1$ and $R_3$ are given in Table A, thus disclosing 412 specific compounds of the formula $I_3$.

Table 4: A further preferred group of compounds of the formula I has the formula

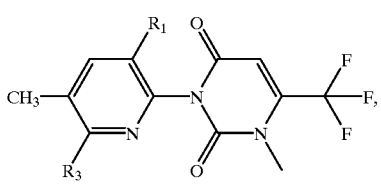
($I_4$)

where the meanings of the respective substituents $R_1$ and $R_3$ are given in Table A, thus disclosing 412 specific compounds of the formula $I_4$.

Table 5: A further preferred group of compounds of the formula I has the formula

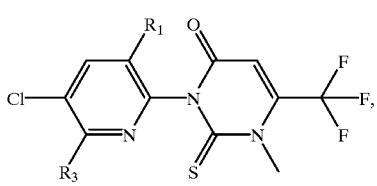
($I_5$)

where the meanings of the respective substituents $R_1$ and $R_3$ are given in Table A, thus disclosing 412 specific compounds of the formula $I_5$.

Table 6: A further preferred group of compounds of the formula I has the formula

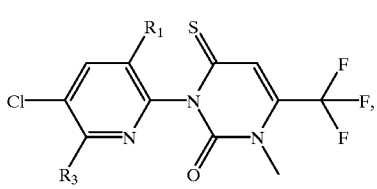
($I_6$)

where the meanings of the respective substituents $R_1$ and $R_3$ are given in Table A, thus disclosing 412 specific compounds of the formula $I_6$.

Table 7: A further preferred group of compounds of the formula I has the formula

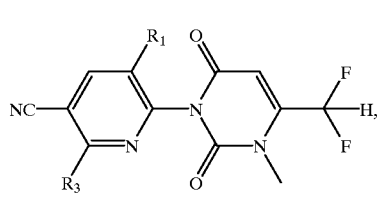
($I_7$)

where the meanings of the respective substituents $R_1$ and $R_3$ are given in Table A, thus disclosing 412 specific compounds of the formula $I_7$.

Table 8: A further preferred group of compounds of the formula I has the formula

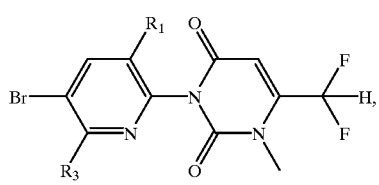
($I_8$)

where the meanings of the respective substituents $R_1$ and $R_3$ are given in Table A, thus disclosing 412 specific compounds of the formula $I_8$.

Table 9: A further preferred group of compounds of the formula I has the formula

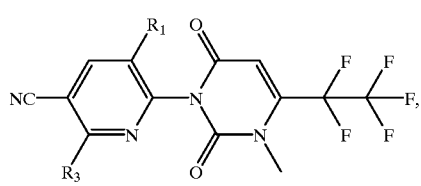
($I_9$)

where the meanings of the respective substituents $R_1$ and $R_3$ are given in Table A, thus disclosing 412 specific compounds of the formula $I_9$.

Table 10: A further preferred group of compounds of the formula I has the formula

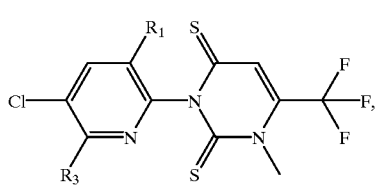
($I_{10}$)

where the meanings of the respective substituents $R_1$ and $R_3$ are given in Table A, thus disclosing 412 specific compounds of the formula $I_{10}$.

Table 11: A further preferred group of compounds of the formula I has the formula

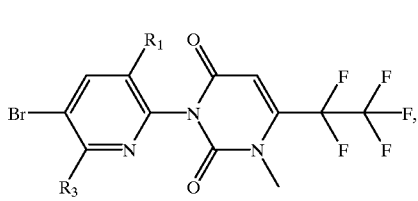

(I₁₁)

where the meanings of the respective substituents R₁ and R₃ are given in Table A, thus disclosing 412 specific compounds of the formula I₁₁.

Table 12: A further preferred group of compounds of the formula I has the formula

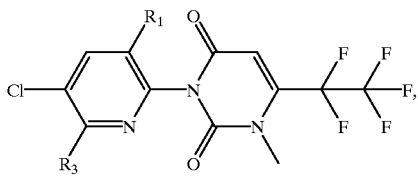

(I₁₂)

where the meanings of the respective substituents R₁ and R₃ are given in Table A, thus disclosing 412 specific compounds of the formula I₁₂.

Table 13: A further preferred group of compounds of the formula I has the formula

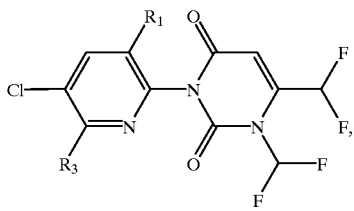

(I₁₃)

where the meanings of the respective substituents R₁ and R₃ are given in Table A, thus disclosing 412 specific compounds of the formula I₁₃.

Table 14: A further preferred group of compounds of the formula I has the formula

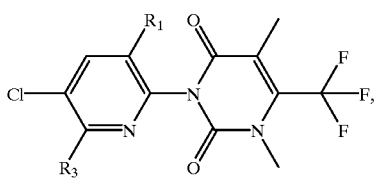

(I₁₄)

where the meanings of the respective substituents R₁ and R₃ are given in Table A, thus disclosing 412 specific compounds of the formula I₁₄.

Table 15: A further preferred group of compounds of the formula I has the formula

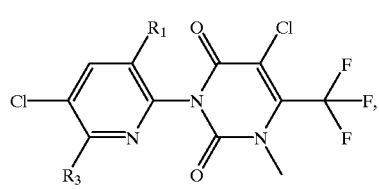

(I₁₅)

where the meanings of the respective substituents R₁ and R₃ are given in Table A, thus disclosing 412 specific compounds of the formula I₁₅.

Table 16: A further preferred group of compounds of the formula I has the formula

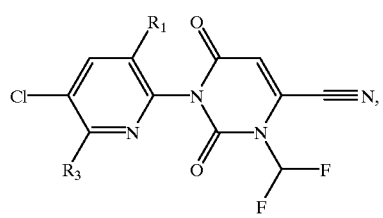

(I₁₆)

where the meanings of the respective substituents R₁ and R₃ are given in Table A, thus disclosing 412 specific compounds of the formula I₁₆.

Table 17: A further preferred group of compounds of the formula I has the formula

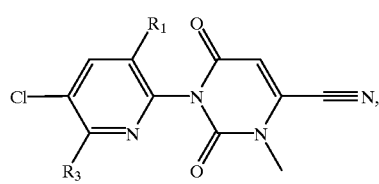

(I₁₇)

where the meanings of the respective substituents R₁ and R₃ are given in Table A, thus disclosing 412 specific compounds of the formula I₁₇.

Table 18: A further preferred group of compounds of the formula I has the formula

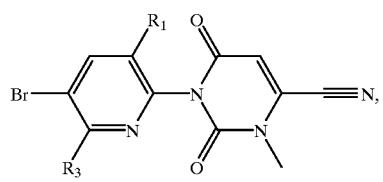

(I₁₈)

where the meanings of the respective substituents R₁ and R₃ are given in Table A, thus disclosing 412 specific compounds of the formula I₁₈.

Table 19: A further preferred group of compounds of the formula I has the formula

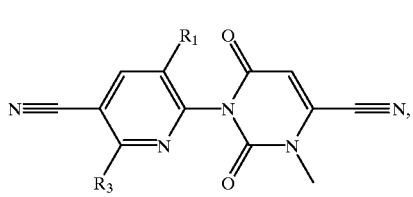

(I$_{19}$)

where the meanings of the respective substituents R$_1$ and R$_3$ are given in Table A, thus disclosing 412 specific compounds of the formula I$_{19}$.

Table 20: A further preferred group of compounds of the formula I has the formula

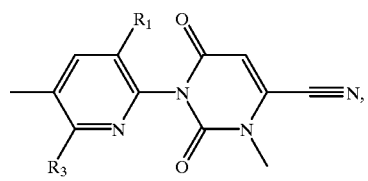

(I$_{20}$)

where the meanings of the respective substituents R$_1$ and R$_3$ are given in Table A, thus disclosing 412 specific compounds of the formula I$_{20}$.

Table 21: A further preferred group of compounds of the formula I has the formula

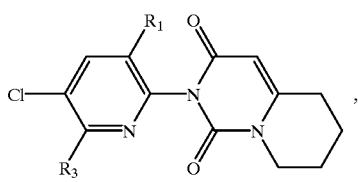

(I$_{21}$)

where the meanings of the respective substituents R$_1$ and R$_3$ are given in Table A, thus disclosing 412 specific compounds of the formula I$_{21}$.

Table 22: A further preferred group of compounds of the formula I has the formula

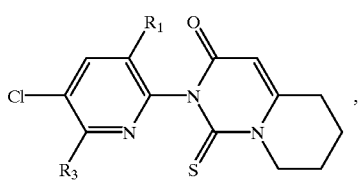

(I$_{22}$)

where the meanings of the respective substituents R$_1$ and R$_3$ are given in Table A, thus disclosing 412 specific compounds of the formula I$_{22}$.

Table 23: A further preferred group of compounds of the formula I has the formula

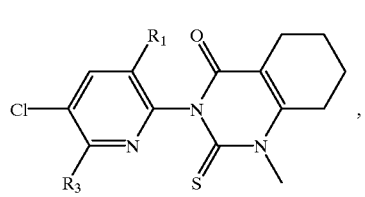

(I$_{23}$)

where the meanings of the respective substituents R$_1$ and R$_3$ are given in Table A, thus disclosing 412 specific compounds of the formula I$_{23}$.

Table 24: A further preferred group of compounds of the formula I has the formula

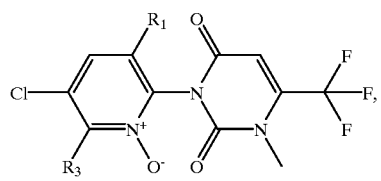

(I$_{24}$)

where the meanings of the respective substituents R$_1$ and R$_3$ are given in Table A, thus disclosing 412 specific compounds of the formula I$_{24}$.

Table 25: A further preferred group of compounds of the formula I has the formula

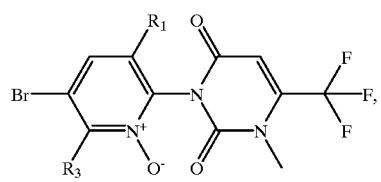

(I$_{25}$)

where the meaning of the respective substituents R$_1$ and R$_3$ are given in Table A, thus disclosing 412 specific compounds of the formula I$_{25}$.

Table 26: A further preferred group of compounds of the formula I has the formula

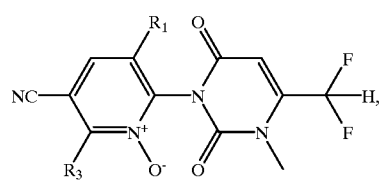

(I$_{26}$)

where the meanings of the respective substituents R$_1$ and R$_3$ are given in Table A, thus disclosing 412 specific compounds of the formula I$_{26}$.

Table 27: A further preferred group of compounds of the formula I has the formula

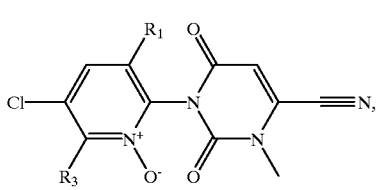

(I$_{27}$)

where the meanings of the respective substituents R$_1$ and R$_3$ are given in Table A, thus disclosing 412 specific compounds of the formula I$_{27}$.

Table 28: A further preferred group of compounds of the formula I has the formula

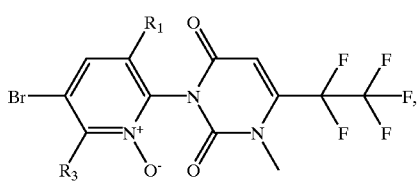

(I$_{28}$)

where the meanings of the respective substituents R$_1$ and R$_3$ are given in Table A, thus disclosing 412 specific compounds of the formula I$_{28}$.

Table 29: A further preferred group of compounds of the formula I has the formula

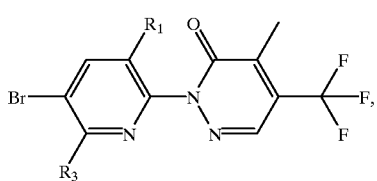

(I$_{29}$)

where the meanings of the respective substituents R$_1$ and R$_3$ are given in Table A, thus disclosing 412 specific compounds of the formula I$_{29}$.

Table 30: A further preferred group of compounds of the formula I has the formula

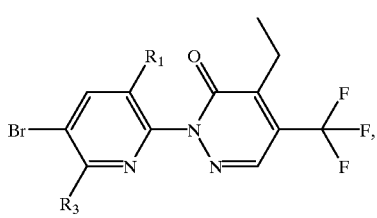

(I$_{30}$)

where the meanings of the respective substituents R$_1$ and R$_3$ are given in Table A, thus disclosing 412 specific compounds of the formula I$_{30}$.

Table 31: A further preferred group of compounds of the formula I has the formula

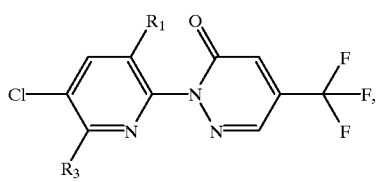

(I$_{31}$)

where the meanings of the respective substituents R$_1$ and R$_3$ are given in Table A, thus disclosing 412 specific compounds of the formula I$_{31}$.

Table 32: A further preferred group of compounds of the formula I has the formula

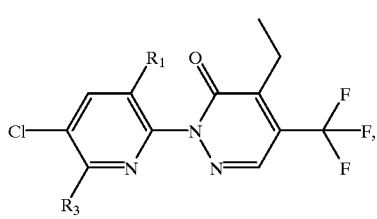

(I$_{32}$)

where the meanings of the respective substituents R$_1$ and R$_3$ are given in Table A, thus disclosing 412 specific compounds of the formula I$_{32}$.

Table 33: A further preferred group of compounds of the formula I has the formula

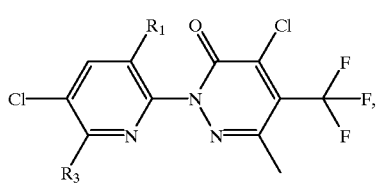

(I$_{33}$)

where the meanings of the respective substituents R$_1$ and R$_3$ are given in Table A, thus disclosing 412 specific compounds of the formula I$_{33}$.

Table 34: A further preferred group of compounds of the formula I has the formula

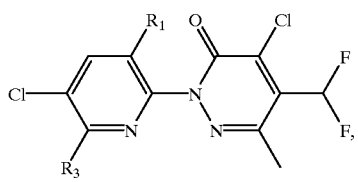

(I$_{34}$)

where the meanings of the respective substituents R$_1$ and R$_3$ are given in Table A, thus disclosing 412 specific compounds of the formula I$_{34}$.

Table 35: A further preferred group of compounds of the formula I has the formula

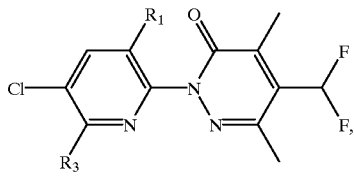

(I$_{35}$)

where the meanings of the respective substituents R$_1$ and R$_3$ given in Table A, thus disclosing 412 specific compounds of the formula I$_{35}$.

Table 36: A further preferred group of compounds of the formula I has the formula

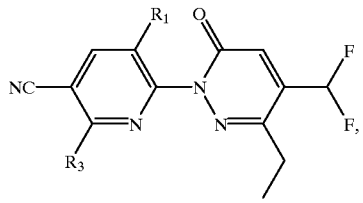

(I$_{36}$)

where the meanings of the respective substituents R$_1$ and R$_3$ are given in Table A, thus disclosing 412 specific compounds of the formula I$_{36}$.

Table 37: A further preferred group of compounds of the formula I has the formula

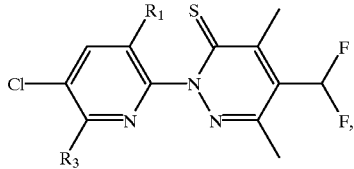

(I$_{37}$)

where the meanings of the respective substituents R$_1$ and R$_3$ are given in Table A, thus disclosing 412 specific compounds of the formula I$_{37}$.

Table 38: A further preferred group of compounds of the formula I has the formula

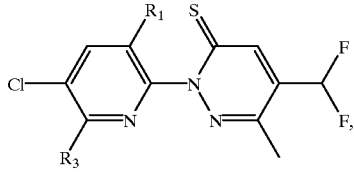

(I$_{38}$)

where the meanings of the respective substituents R$_1$ and R$_3$ are given in Table A, thus disclosing 412 specific compounds of the formula I$_{38}$.

Table 39: A further preferred group of compounds of the formula I has the formula

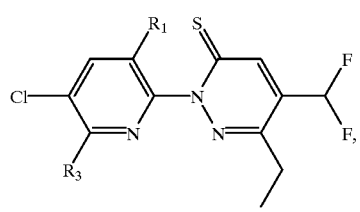

(I$_{39}$)

where the meanings of the respective substituents R$_1$ and R$_3$ are given in Table A, thus disclosing 412 specific compounds of the formula I$_{39}$.

Table 40: A further preferred group of compounds of the formula I has the formula

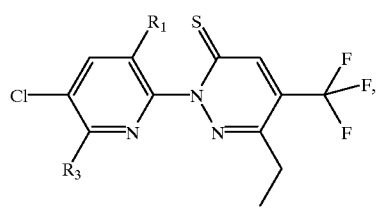

(I$_{40}$)

where the meanings of the respective substituents R$_1$ and R$_3$ are given in Table A, thus disclosing 412 specific compounds of the formula I$_{40}$.

Table 41: A further preferred group of compounds of the formula I has the formula

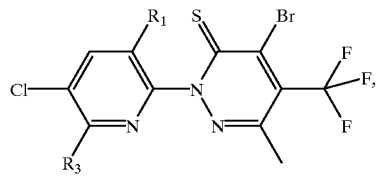

(I$_{41}$)

where the meanings of the respective substituents R$_1$ and R$_3$ are given in Table A, thus disclosing 412 specific compounds of the formula I$_{41}$.

Table 42: A further preferred group of compounds of the formula I has the formula

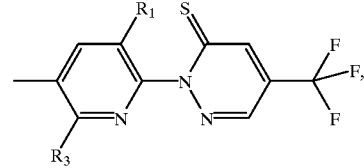

(I$_{42}$)

where the meanings of the respective substituents R$_1$ and R$_3$ are given in Table A, thus disclosing 412 specific compounds of the formula I$_{42}$.

Table 43: A further preferred group of compounds of the formula I has the formula

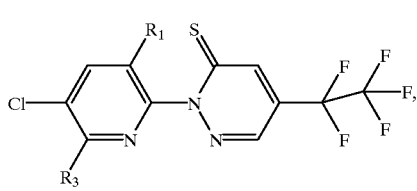
(I₄₃)

where the meaning of the respective substituents $R_1$ and $R_3$ are given in Table A, thus disclosing 412 specific compounds of the formula $I_{43}$.

Table 44: A further preferred group of compounds of the formula I has the formula

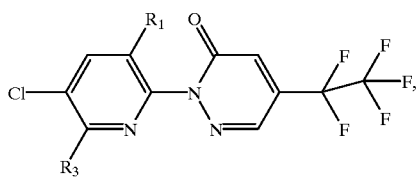
(I₄₄)

where the meaning of the respective substituents $R_1$ and $R_3$ are given in Table A, thus disclosing 412 specific compounds of the formula $I_{44}$.

Table 45: A further preferred group of compounds of the formula I has the formula

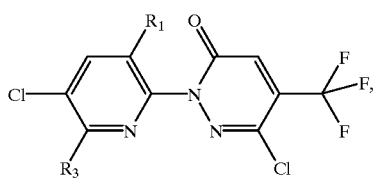
(I₄₅)

where the meaning of the respective substituents $R_1$ and $R_3$ are given in Table A, thus disclosing 412 specific compounds of the formula $I_{45}$.

Table 46: A further preferred group of compounds of the formula I has the formula

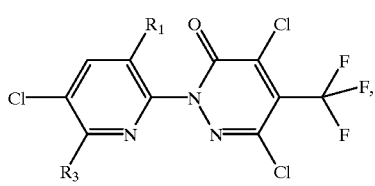
(I₄₆)

where the meaning of the respective substituents $R_1$ and $R_3$ are given in Table A, thus disclosing 412 specific compounds of the formula $I_{46}$.

Table 47: A further preferred group of compounds of the formula I has the formula

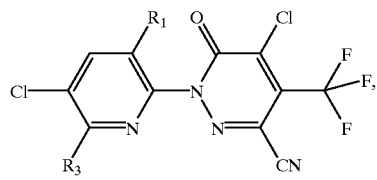
(I₄₇)

where the meaning of the respective substituents $R_1$ and $R_3$ are given in Table A, thus disclosing 412 specific compounds of the formula $I_{47}$.

Table 48: A further preferred group df compounds of the formula I has the formula

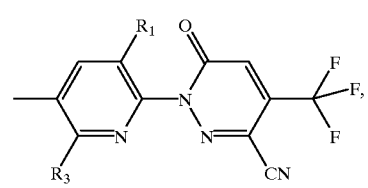
(I₄₈)

where the meaning of the respective substituents $R_1$ and $R_3$ are given in Table A, thus disclosing 412 specific compounds of the formula $I_{48}$.

Table 49: A further preferred group of compounds of the formula I has the formula

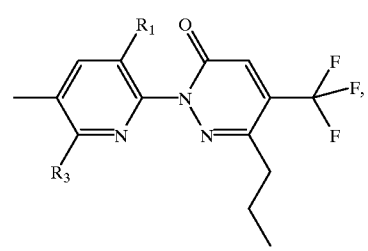
(I₄₉)

where the meaning of the respective substituents $R_1$ and $R_3$ are given in Table A, thus disclosing 412 specific compounds of the formula $I_{49}$.

Table 50. A further preferred group of compounds of the formula I has the formula

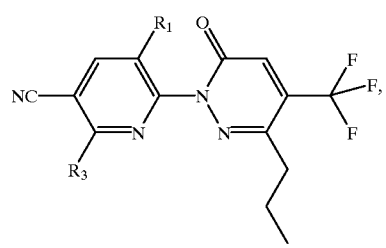
(I₅₀)

where the meaning of the respective substituents $R_1$ and $R_3$ are given in Table A, thus disclosing 412 specific compounds of the formula $I_{50}$.

Table 51: A further preferred group of compounds of the formula I has the formula

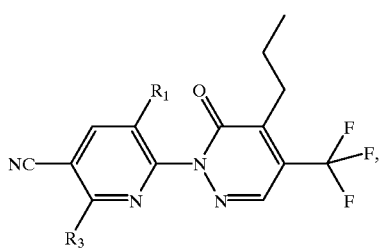

(I₅₁)

where the meaning of the respective substituents $R_1$ and $R_3$ are given in Table A, thus disclosing 412 specific compounds of the formula $I_{51}$.

Table 52: A further preferred group of compounds of the formula I has the formula

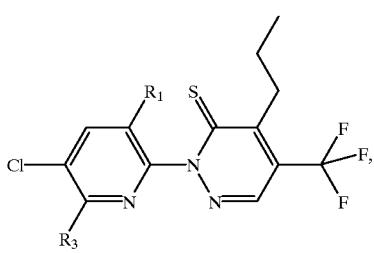

(I₅₂)

where the meaning of the respective substituents $R_1$ and $R_3$ are given in Table A, thus disclosing 412 specific compounds of the formula $I_{52}$.

Table 53: A further preferred group of compounds of the formula I has the formula

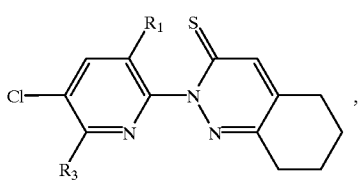

(I₅₃)

where the meaning of the respective substituents $R_1$ and $R_3$ are given in Table A, thus disclosing 412 specific compounds of the formula $I_{53}$.

Table 54: A further preferred group of compounds of the formula I has the formula

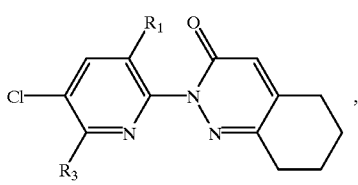

(I₅₄)

where the meaning of the respective substituents $R_1$ and $R_3$ are given in Table A, thus disclosing 412 specific compounds of the formula $I_{54}$.

Table 55: A further preferred group of compounds of the formula I has the formula

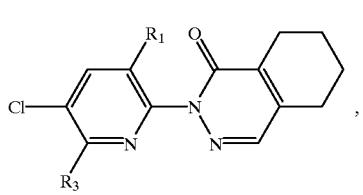

(I₅₅)

where the meaning of the respective substituents $R_1$ and $R_3$ are given in Table A, thus disclosing 412 specific compound of the formula $I_{55}$.

Table 56: A further preferred group of compounds of the formula I has the formula

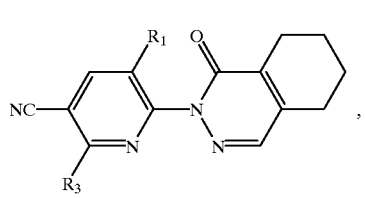

(I₅₆)

where the meaning of the respective substituents $R_1$ and $R_3$ are given in Table A, thus disclosing 412 specific compounds of the formula $I_{56}$.

Table 57: A further preferred group of compounds of the formula I has the formula

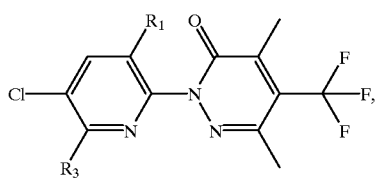

(I₅₇)

where the meaning of the respective substituents $R_1$ and $R_3$ are given in Table A, thus disclosing 412 specific compounds of the formula $I_{57}$.

Table 58: A further preferred group of compounds of the formula I has the formula

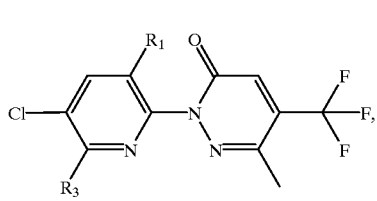

(I₅₈)

where the meaning of the respective substituents $R_1$ and $R_3$ are given in Table A, thus disclosing 412 specific compounds of the formula $I_{58}$.

Table 59: A further preferred group of compounds of the formula I has the formula

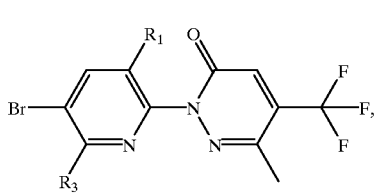

(I$_{59}$)

where the meaning of the respective substituents R$_1$ and R$_3$ are given in Table A, thus disclosing 412 specific compounds of the formula I$_{59}$.

Table 60: A further preferred group of compounds of the formula I has the formula

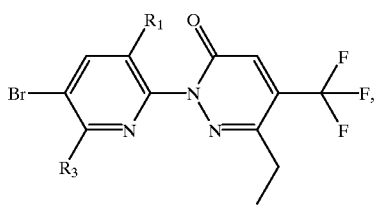

(I$_{60}$)

where the meaning of the respective substituents R$_1$ and R$_3$ are given in Table A, thus disclosing 412 specific compounds of the formula I$_{60}$.

Table 61: A further preferred group of compounds of the formula I has the formula

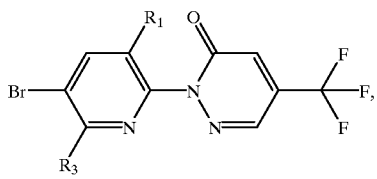

(I$_{61}$)

where the meaning of the respective substituents R$_1$ and R$_3$ are given in Table A, thus disclosing 412 specific compounds of the formula I$_{61}$.

Table 62: A further preferred group of compounds of the formula I has the formula

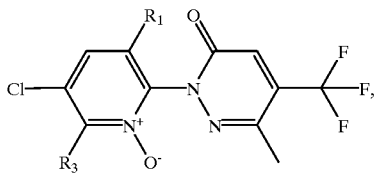

(I$_{62}$)

where the meaning of the respective substituents R$_1$ and R$_3$ are given in Table A, thus disclosing 412 specific compounds of the formula I$_{62}$.

Table 63: A further preferred group of compounds of the formula I has the formula

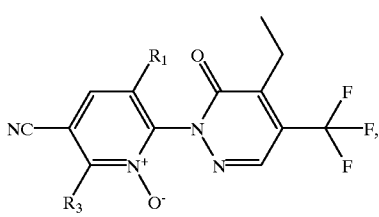

(I$_{63}$)

where the meaning of the respective substituents R$_1$ and R$_3$ are given in Table A, thus disclosing 412 specific compounds of the formula I$_{63}$.

Table 64: A further preferred group of compounds of the formula I has the formula

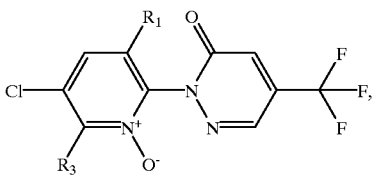

(I$_{64}$)

where the meaning of the respective substituents R$_1$ and R$_3$ are given in Table A, thus disclosing 412 specific compounds of the formula I$_{64}$.

Table 65: A further preferred group of compounds of the formula I has the formula

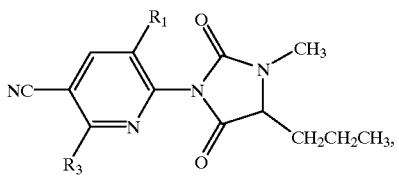

(I$_{65}$)

where the meaning of the respective substituents R$_1$ and R$_3$ are given in Table A, thus disclosing 412 specific compounds of the formula I$_{65}$.

Table 66: A further preferred group of compounds of the formula I has the formula

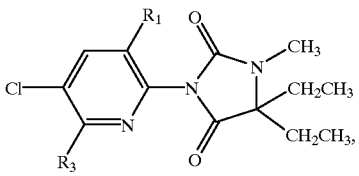

(I$_{66}$)

where the meaning the of the respective substituents R$_1$ and R$_3$ are given in Table A, thus disclosing 412 specific compounds of the formula I$_{66}$.

Table 67: A further preferred group of compounds of the formula I has the formula

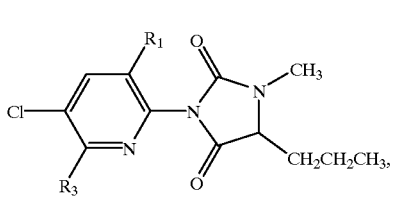
(I$_{67}$)

where the meaning of the respective substituents R$_1$ and R$_3$ are given in Table A, thus disclosing 412 specific compounds of the formula I$_{67}$.

Table 68: A further preferred group of compounds of the formula I has the formula

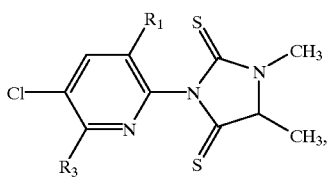
(I$_{68}$)

where the meaning of the respective substituents R$_1$ and R$_3$ are given in Table A, thus disclosing 412 specific compounds of the formula I$_{68}$.

Table 69: A further preferred group of compounds of the formula I has the formula

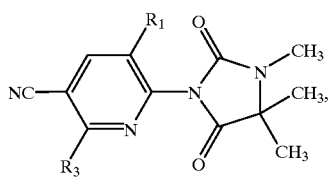
(I$_{69}$)

where the meaning of the respective substituents R$_1$ and R$_3$ are given in Table A, thus disclosing 412 specific compounds of the formula I$_{69}$.

Table 70: A further preferred group of compounds of the formula I has the formula

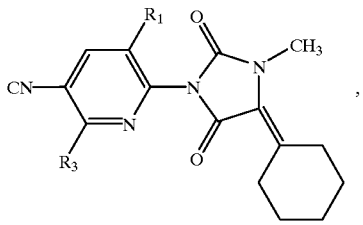
(I$_{70}$)

where the meaning of the respective substituents R$_1$ and R$_3$ are given in Table A, thus disclosing 412 specific compounds of the formula I$_{70}$.

Table 71: A further preferred group of compounds of the formula I has the formula

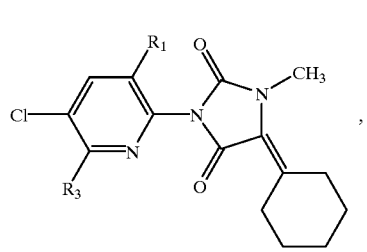
(I$_{71}$)

where the meaning of the respective substituents R$_1$ and R$_3$ are given in Table A, thus disclosing 412 specific compounds of the formula I$_{71}$.

Table 72: A further preferred group of compounds of the formula I has the formula

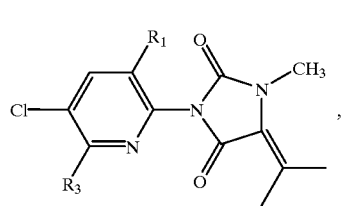
(I$_{72}$)

where the meaning of the respective substituents R$_1$ and R$_3$ are given in Table A, thus disclosing 412 specific compounds of the formula I$_{72}$.

Table 73: A further preferred group of compounds of the formula I has the formula

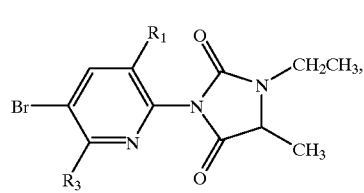
(I$_{73}$)

where the meaning of the respective substituents R$_1$ and R$_3$ are given in Table A, thus disclosing 412 specific compounds of the formula I$_{73}$.

Table 74: A further preferred group of compounds of the formula I has the formula

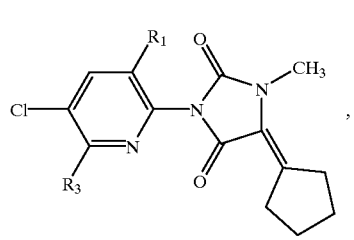
(I$_{74}$)

where the meaning of the respective substituents R$_1$ and R$_3$ are given in Table A, thus disclosing 412 specific compounds of the formula I$_{74}$.

Table 75: A further preferred group of compounds of the formula I has the formula

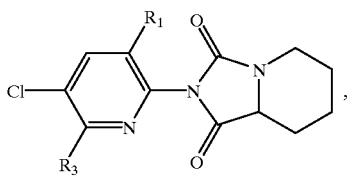
(I₇₅)

where the meaning of the respective substituents $R_1$ and $R_3$ are given in Table A, thus disclosing 412 specific compounds of the formula $I_{75}$.

Table 76: A further preferred group of compounds of the formula I has the formula

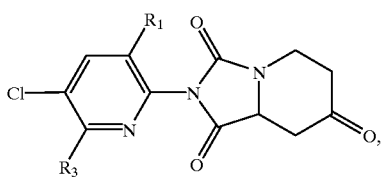
(I₇₆)

where the meaning of the respective substituents $R_1$ and $R_3$ are given in Table A, thus disclosing 412 specific compounds of the formula $I_{76}$.

Table 77: A further preferred group of compounds of the formula I has the formula

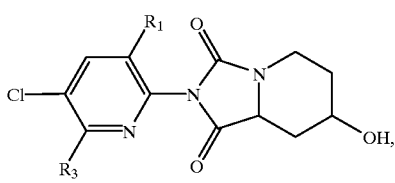
(I₇₇)

where the meaning of the respective substituents $R_1$ and $R_3$ are given in Table A, thus disclosing 412 specific compounds of the formula $I_{77}$.

Table 78: A further preferred group of compounds of the formula I has the formula

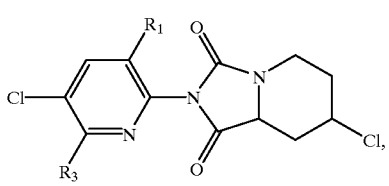
(I₇₈)

where the meaning of the respective substituents $R_1$ and $R_3$ are given in Table A, thus disclosing 412 specific compounds of the formula $I_{78}$.

Table 79: A further preferred group of compounds of the formula I has the formula

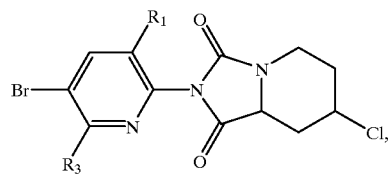
(I₇₉)

where the meaning of the respective substituents $R_1$ and $R_3$ are given in Table A, thus disclosing 412 specific compounds of the formula $I_{79}$.

Table 80: A further preferred group of compounds of the formula I has the formula

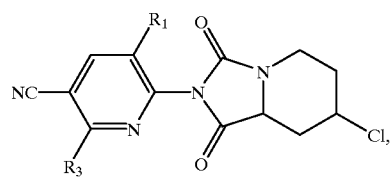
(I₈₀)

where the meaning of the respective substituents $R_1$ and $R_3$ are given in Table A, thus disclosing 412 specific compounds of the formula $I_{80}$.

Table 81: A further preferred group of compounds of the formula I has the formula

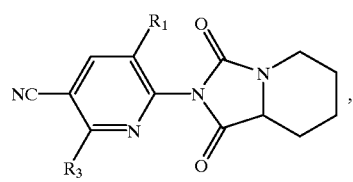
(I₈₁)

where the meaning of the respective substituents $R_1$ and $R_3$ are given in Table A, thus disclosing 412 specific compounds of the formula $I_{81}$.

Table 82: A further preferred group of compounds of the formula I has the formula

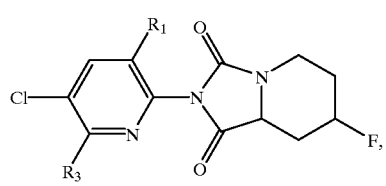
(I₈₂)

where the meaning of the respective substituents $R_1$ and $R_3$ are given in Table A, thus disclosing 412 specific compounds of the formula $I_{82}$.

Table 83: A further preferred group of compounds of the formula I has the formula

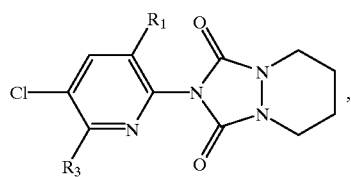

(I₈₃)

where the meaning of the respective substituents $R_1$ and $R_3$ are given in Table A, thus disclosing 412 specific compounds of the formula $I_{83}$.

Table 84: A further preferred group of compounds of the formula I has the formula

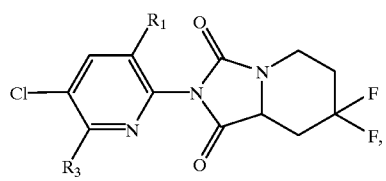

(I₈₄)

where the meaning of the respective substituents $R_1$ and $R_3$ are given in Table A, thus disclosing 412 specific compounds of the formula $I_{84}$.

Table 85: A further preferred group of compounds of the formula I has the formula

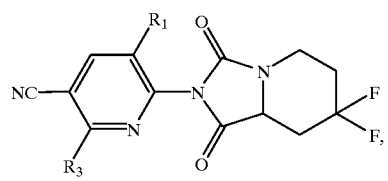

(I₈₅)

where the meaning of the respective substituents $R_1$ and $R_3$ are given in Table A, thus disclosing 412 specific compounds of the formula $I_{85}$.

Table 86: A further preferred group of compounds of the formula I has the formula

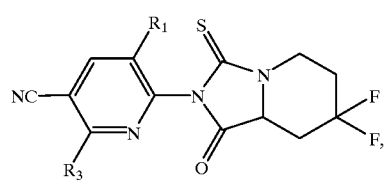

(I₈₆)

where the meaning of the respective substituents $R_1$ and $R_3$ are given in Table A, thus disclosing 412 specific compounds of the formula $I_{86}$.

Table 87: A further preferred group of compounds of the formula I has the formula

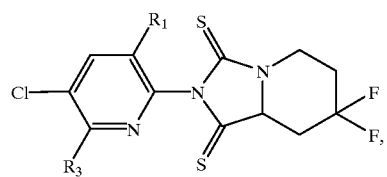

(I₈₇)

where the meaning of the respective substituents $R_1$ and $R_3$ are given in Table A, thus disclosing 412 specific compounds of the formula $I_{87}$.

Table 88: A further preferred group of compounds of the formula I has the formula

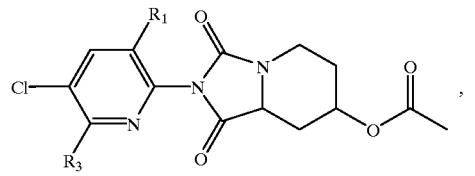

(I₈₈)

where the meaning of the respective substituents $R_1$ and $R_3$ are given in Table A, thus disclosing 412 specific compounds of the formula $I_{88}$.

Table 89: A further preferred group of compounds of the formula I has the formula

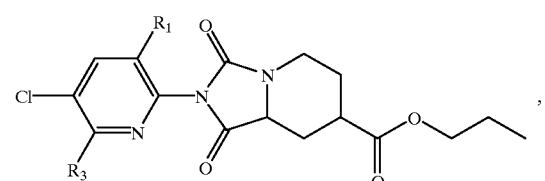

(I₈₉)

where the meaning of the respective substituents $R_1$ and $R_3$ are given in Table A, thus disclosing 412 specific compounds of the formula $I_{89}$.

Table 90: A further preferred group of compounds of the formula I has the formula

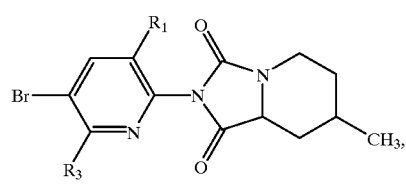

(I₉₀)

where the meaning of the respective substituents $R_1$ and $R_3$ are given in Table A, thus disclosing 412 specific compounds of the formula $I_{90}$.

Table 91: A further preferred group of compounds of the formula I has the formula

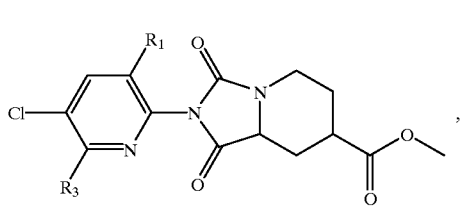
(I₉₁)

where the meaning of the respective substituents $R_1$ and $R_3$ are given in Table A, thus disclosing 412 specific compounds of the formula $I_{91}$.

Table 92: A further preferred group of compounds of the formula I has the formula

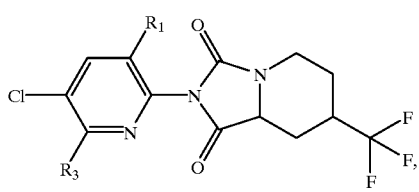
(I₉₂)

where the meaning of the respective substituents $R_1$ and $R_3$ are given in Table A, thus disclosing 412 specific compounds of the formula $I_{92}$.

Table 93: A further preferred group of compounds of the formula I has the formula

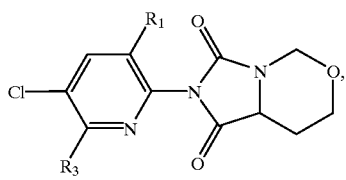
(I₉₃)

where the meaning of the respective substituents $R_1$ and $R_3$ are given in Table A, thus disclosing 412 specific compounds of the formula $I_{93}$.

Table 94: A further preferred group of compounds of the formula I has the formula

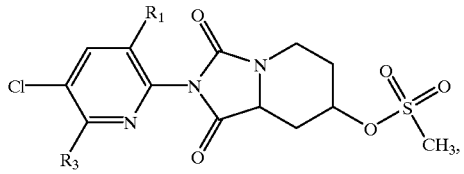
(I₉₄)

where the meaning of the respective substituents $R_1$ and $R_3$ are given in Table A, thus disclosing 412 specific compounds of the formula $I_{94}$.

Table 95: A further preferred group of compounds of the formula I has the formula

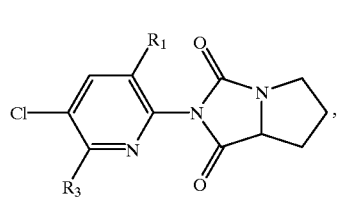
(I₉₅)

where the meaning of the respective substituents $R_1$ and $R_3$ are given in Table A, thus disclosing 412 specific compounds of the formula $I_{95}$.

Table 96: A further preferred group of compounds of the formula I has the formula

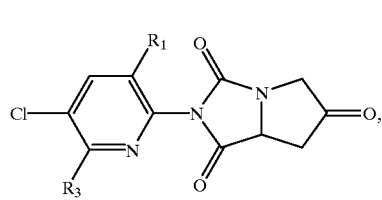
(I₉₆)

where the meaning of the respective substituents $R_1$ and $R_3$ are given in Table A, thus disclosing 412 specific compounds of the formula $I_{96}$.

Table 97: A further preferred group of compounds of the formula I has the formula

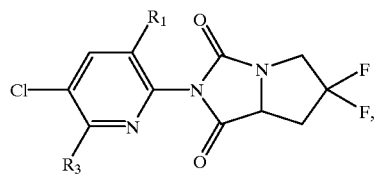
(I₉₇)

where the meaning of the respective substituents $R_1$ and $R_3$ are given in Table A, thus disclosing 412 specific compounds of the formula $I_{97}$.

Table 98: A further preferred group of compounds of the formula I has the formula

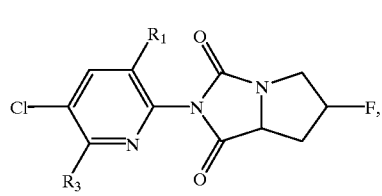
(I₉₈)

where the meaning of the respective substituents $R_1$ and $R_3$e given in Table A, thus disclosing 412 specific compounds of the formula $I_{98}$.

Table 99: A further preferred group of compounds of the formula I has the formula

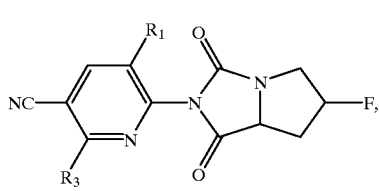

(I$_{99}$)

where the meaning of the respective substituents $R_1$ and $R_3$ are given in Table A, thus disclosing 412 specific compounds of the formula $I_{99}$.

Table 100: A further preferred group of compounds of the formula I has the formula

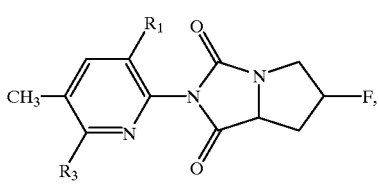

(I$_{100}$)

where the meaning of the respective substituents $R_1$ and $R_3$ are given in Table A, thus disclosing 412 specific compounds of the formula $I_{100}$.

Table 101: A further preferred group of compounds of the formula I has the formula

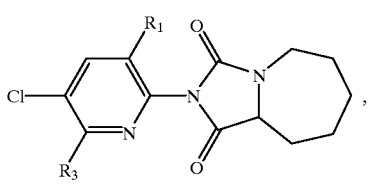

(I$_{101}$)

where the meaning of the respective substituents $R_1$ and $R_3$ are given in Table A, thus disclosing 412 specific compounds of the formula $I_{101}$.

Table 102: A further preferred group of compounds of the formula I has the formula

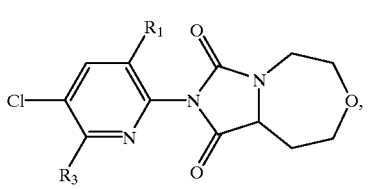

(I$_{102}$)

where the meaning of the respective substituents $R_1$ and $R_3$ are given in Table A, thus disclosing 412 specific compounds of the formula $I_{102}$.

Table 103: A further preferred group of compounds of the formula I has the formula

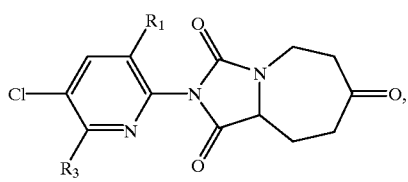

(I$_{103}$)

where the meaning of the respective substituents $R_1$ and $R_3$ are given in Table A, thus disclosing 412 specific compounds of the formula $I_{103}$.

Table 104: A further preferred group of compounds of the formula I has the formula

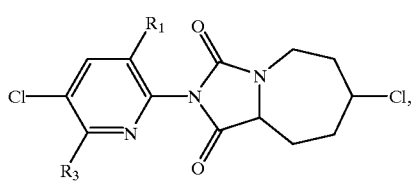

(I$_{104}$)

where the meaning of the respective substituents $R_1$ and $R_3$ are given in Table A, thus disclosing 412 specific compounds of the formula $I_{104}$.

Table 105: A further preferred group of compounds of the formula I has the formula

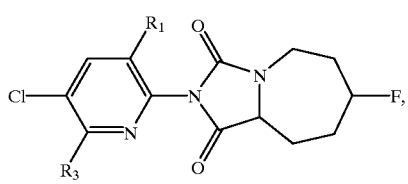

(I$_{105}$)

where the meaning of the respective substituents $R_1$ and $R_3$ are given in Table A, thus disclosing 412 specific compounds of the formula $I_{105}$.

Table 106: A further preferred group of compounds of the formula I has the formula

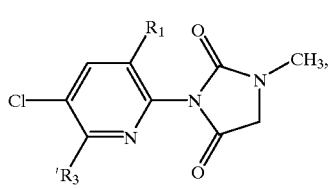

(I$_{106}$)

where the meaning of the respective substituents $R_1$ and $R_3$ are given in Table A, thus disclosing 412 specific compounds of the formula $I_{106}$.

Table 107: A further preferred group of compounds of the formula I has the formula

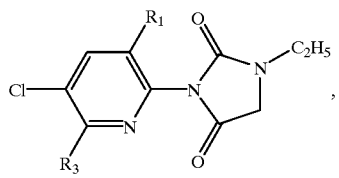 (I₁₀₇)

where the meaning of the respective substituents $R_1$ and $R_3$ are given in Table A, thus disclosing 412 specific compounds of the formula $I_{107}$.

Table 108: A further preferred group of compounds of the formula I has the formula

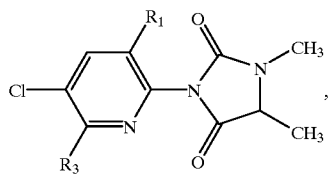 (I₁₀₈)

where the meaning of the respective substituents $R_1$ and $R_3$ are given in Table A, thus disclosing 412 specific compounds of the formula $I_{108}$.

Table 109: A further preferred group of compounds of the formula I has the formula

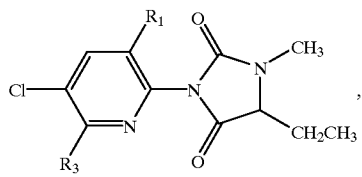 (I₁₀₉)

where the meaning of the respective substituents $R_1$ and $R_3$ are given in Table A, thus disclosing 412 specific compounds of the formula $I_{109}$.

Table 110: A further preferred group of compounds of the formula I has the formula

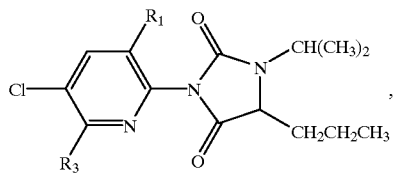 (I₁₁₀)

where the meaning of the respective substituents $R_1$ and $R_3$ are given in Table A, thus disclosing 412 specific compounds of the formula $I_{110}$.

Table 111: A further preferred group of compounds of the formula I has the formula

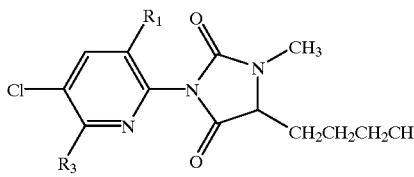 (I₁₁₁)

where the meaning of the respective substituents $R_1$ and $R_3$ are given in Table A, thus disclosing 412 specific compounds of the formula $I_{111}$.

Table 112: A further preferred group of compounds of the formula I has the formula

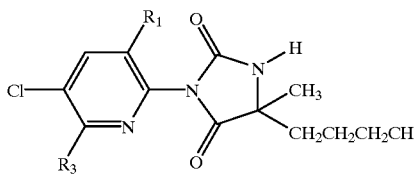 (I₁₁₂)

where the meaning of the respective substituents $R_1$ and $R_3$ are given in Table A, thus disclosing 412 specific compounds of the formula $I_{112}$.

Table 113: A further preferred group of compounds of the formula I has the formula

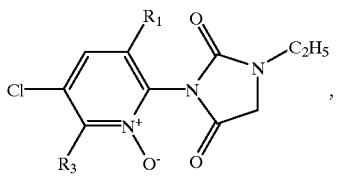 (I₁₁₃)

where the meaning of the respective substituents $R_1$ and $R_3$ are given in Table A, thus disclosing 412 specific compounds of the formula $I_{113}$.

Table 114: A further preferred group of compounds of the formula I has the formula

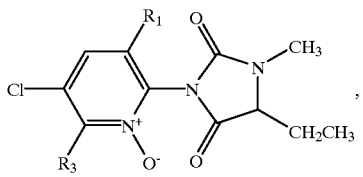 (I₁₁₄)

where the meaning of the respective substituents $R_1$ and $R_3$ are given in Table A, thus disclosing 412 specific compounds of the formula $I_{114}$.

Table 115: A further preferred group of compounds of the formula I has the formula

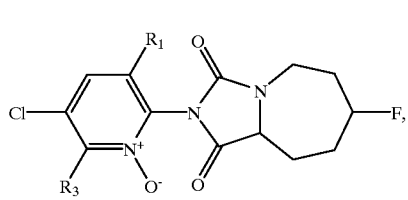

(I₁₁₅)

where the meaning of the respective substituents $R_1$ and $R_3$ are given in Table A, thus disclosing 412 specific compounds of the formula $I_{115}$.

Table 116: A further preferred group of compounds of the formula I has the formula

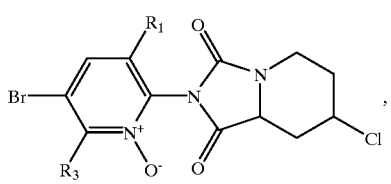

(I₁₁₆)

where the meaning of the respective substituents $R_1$ and $R_3$ are given in Table A, thus disclosing 412 specific compounds of the formula $I_{116}$.

Table 117: A further preferred group of compounds of the formula I has the formula

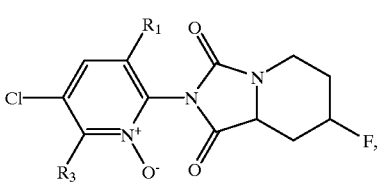

(I₁₁₇)

where the meaning of the respective substituents $R_1$ and $R_3$ are given in Table A, thus disclosing 412 specific compounds of the formula $I_{117}$.

Table 118: A further preferred group of compounds of the formula I has the formula

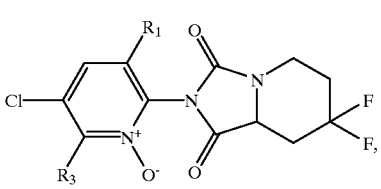

(I₁₁₈)

where the meaning of the respective substituents $R_1$ and $R_3$ are given in Table A, thus disclosing 412 specific compounds of the formula $I_{118}$.

Table 119: A further preferred group of compounds of the formula I has the formula

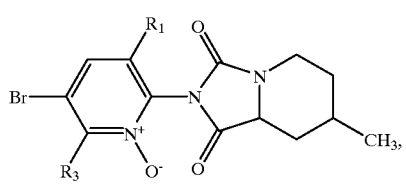

(I₁₁₉)

where the meaning of the respective substituents $R_1$ and $R_3$ are given in Table A, thus disclosing 412 specific compounds of the formula $I_{119}$.

Table 120: A further preferred group of compounds of the formula I has the formula

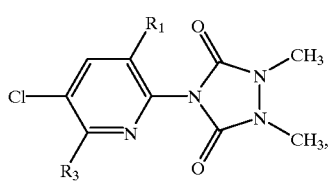

(I₁₂₀)

where the meaning of the respective substituents $R_1$ and $R_3$ are given in Table A, thus disclosing 412 specific compounds of the formula $I_{120}$.

Table 121: A further preferred group of compounds of the formula I has the formula

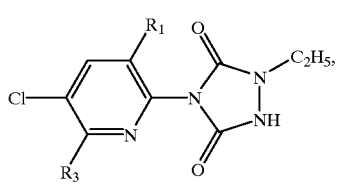

(I₁₂₁)

where the meaning of the respective substituents $R_1$ and $R_3$ are given in Table A, thus disclosing 412 specific compounds of the formula $I_{121}$.

Table 122: A further preferred group of compounds of the formula I has the formula

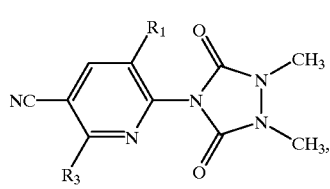

(I₁₂₂)

where the meaning of the respective substituents $R_1$ and $R_3$ are given in Table A, thus disclosing 412 specific compounds of the formula $I_{122}$.

Table 123: A further preferred group of compounds of the formula I has the formula

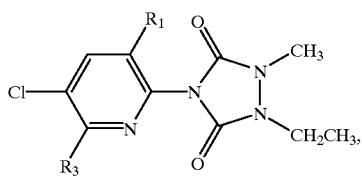

(I₁₂₃)

where the meaning of the respective substituents $R_1$ and $R_3$ are given in Table A, thus disclosing 412 specific compounds of the formula $I_{123}$.

Table 124: A further preferred group of compounds of the formula I has the formula

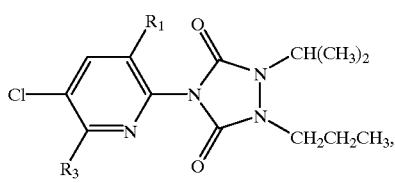

(I₁₂₄)

where the meaning of the respective substituents $R_1$ and $R_3$ are given in Table A, thus disclosing 412 specific compounds of the formula $I_{124}$.

Table 125: A further preferred group of compounds of the formula I has the formula

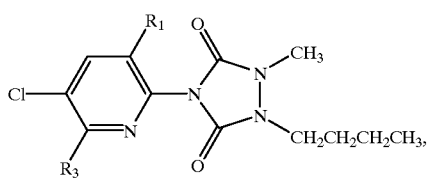

(I₁₂₅)

where the meaning of the respective substituents $R_1$ and $R_3$ are given in Table A, thus disclosing 412 specific compounds of the formula $I_{125}$.

Table 126: A further preferred group of compounds of the formula I has the formula

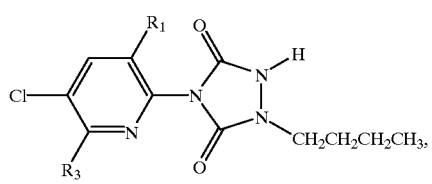

(I₁₂₆)

where the meaning of the respective substituents $R_1$ and $R_3$ are given in Table A, thus disclosing 412 specific compounds of the formula $I_{126}$.

Table 127: A further preferred group of compounds of the formula I has the formula

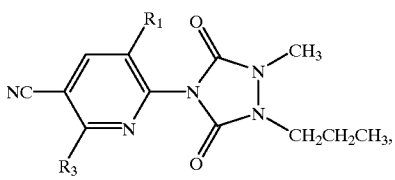

(I₁₂₇)

where the meaning of the respective substituents $R_1$ and $R_3$ are given in Table A, thus disclosing 412 specific compounds of the formula $I_{127}$.

Table 128: A further preferred group of compounds of the formula I has the formula

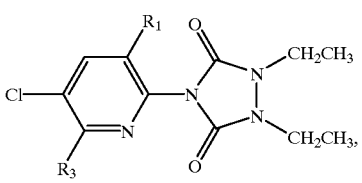

(I₁₂₈)

where the meaning of the respective substituents $R_1$ and $R_3$ are given in Table A, thus disclosing 412 specific compounds of the formula $I_{128}$.

Table 129: A further preferred group of compounds of the formula I has the formula

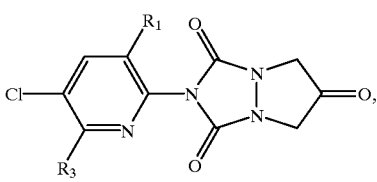

(I₁₂₉)

where the meaning of the respective substituents $R_1$ and $R_3$ are given in Table A, thus disclosing 412 specific compounds of the formula $I_{129}$.

Table 130: A further preferred group of compounds of the formula I has the formula

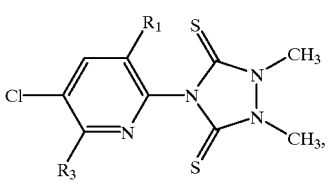

(I₁₃₀)

where the meaning of the respective substituents $R_1$ and $R_3$ are given in Table A, thus disclosing 412 specific compounds of the formula $_{130}$.

Table 131: A further preferred group of compounds of the formula I has the formula

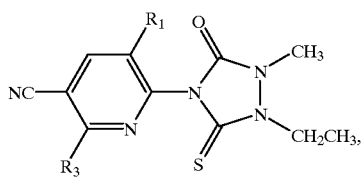
(I₁₃₁)

where the meaning of the respective substituents $R_1$ and $R_3$ are given in Table A, thus disclosing 412 specific compounds of the formula $I_{131}$.

Table 132: A further preferred group of compounds of the formula I has the formula

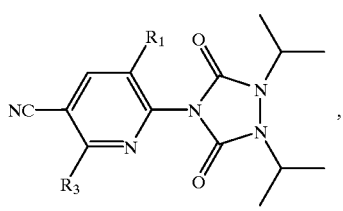
(I₁₃₂)

where the meaning of the respective substituents $R_1$ and $R_3$ are given in Table A, thus disclosing 412 specific compounds of the formula $I_{132}$.

Table 133: A further preferred group of compounds of the formula I has the formula

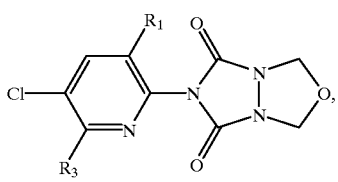
(I₁₃₃)

where the meaning of the respective substituents $R_1$ and $R_3$ are given in Table A, thus disclosing 412 specific compounds of the formula $I_{133}$.

Table 134: A further preferred group of compounds of the formula I has the formula

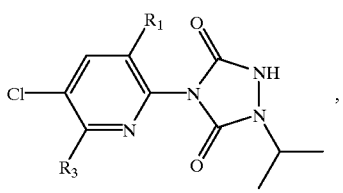
(I₁₃₄)

where the meaning of the respective substituents $R_1$ and $R_3$ are given in Table A, thus disclosing 412 specific compounds of the formula $I_{134}$ Table 135: A further preferred group of compounds of the formula I has the formula

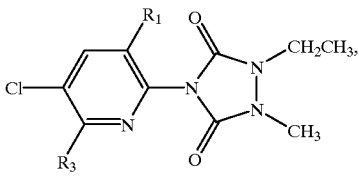
(I₁₃₅)

where the meaning of the respective substituents $R_1$ and $R_3$ are given in Table A, thus disclosing 412 specific compounds of the formula $I_{135}$.

Table 136: A further preferred group of compounds of the formula I has the formula

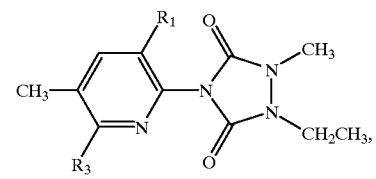
(I₁₃₆)

where the meaning of the respective substituents $R_1$ and $R_3$ are given in Table A, thus disclosing 412 specific compounds of the formula $I_{136}$.

Table 137: A further preferred group of compounds of the formula I has the formula

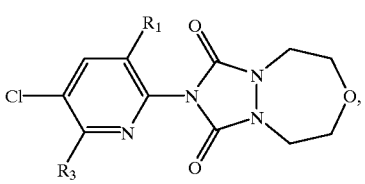
(I₁₃₇)

where the meaning of the respective substituents $R_1$ and $R_3$ are given in Table A, thus disclosing 412 specific compounds of the formula $I_{137}$.

Table 138: A further preferred group of compounds of the formula I has the formula

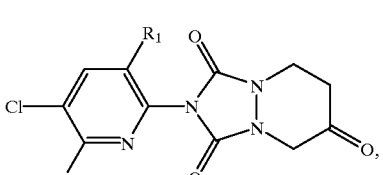
(I₁₃₈)

where the meaning of the respective substituents $R_1$ and $R_3$ are given in Table A, thus disclosing 412 specific compounds of the formula $I_{138}$.

Table 139: A further preferred group of compounds of the formula I has the formula

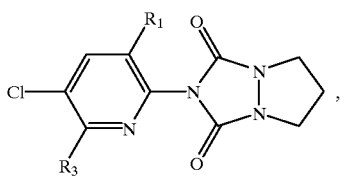

(I$_{139}$)

where the meaning of the respective substituents $R_1$ and $R_3$ are given in Table A, thus disclosing 412 specific compounds of the formula I$_{139}$.

Table 140: A further preferred group of compounds of the formula I has the formula

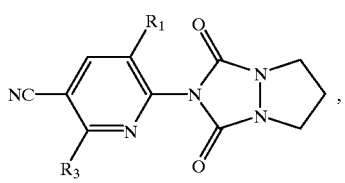

(I$_{140}$)

where the meaning of the respective substituents $R_1$ and $R_3$ are given in Table A, thus disclosing 412 specific compounds of the formula I$_{140}$ Table 141: A further preferred group of compounds of the formula I has the formula

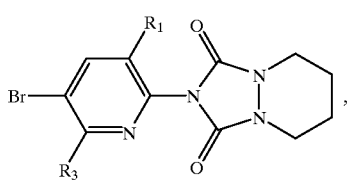

(I$_{141}$)

where the meaning of the respective substituents $R_1$ and $R_3$ are given in Table A, thus disclosing 412 specific compounds of the formula I$_{141}$.

Table 142: A further preferred group of compounds of the formula I has the formula

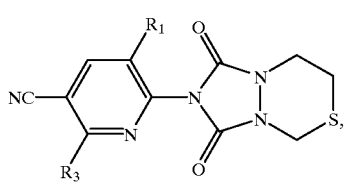

(I$_{142}$)

where the meaning of the respective substituents $R_1$ and $R_3$ are given in Table A, thus disclosing 412 specific compounds of the formula I$_{142}$.

Table 143: A further preferred group of compounds of the formula I has the formula

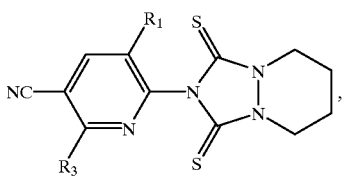

(I$_{143}$)

where the meaning of the respective substituents $R_1$ and $R_3$ are given in Table A, thus disclosing 412 specific compounds of the formula I$_{143}$.

Table 144: A further preferred group of compounds of the formula I has the formula

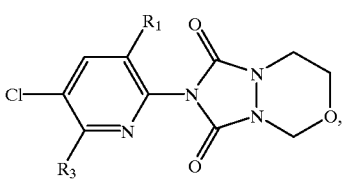

(I$_{144}$)

where the meaning of the respective substituents $R_1$ and $R_3$ are given in Table A, thus disclosing 412 specific compounds of the formula I$_{144}$.

Table 145: A further preferred group of compounds of the formula I has the formula

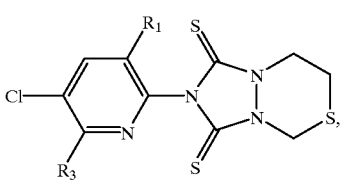

(I$_{145}$)

where the meaning of the respective substituents $R_1$ and $R_3$ are given in Table A, thus disclosing 412 specific compounds of the formula I$_{145}$.

Table 146: A further preferred group of compounds of the formula I has the formula

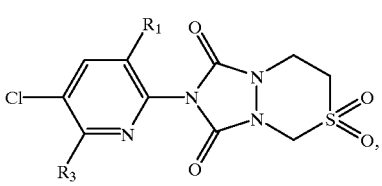

(I$_{146}$)

where the meaning of the respective substituents $R_1$ and $R_3$ are given in Table A, thus disclosing 412 specific compounds of the formula I$_{146}$.

Table 147: A further preferred group of compounds of the formula I has the formula

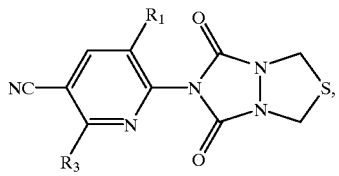

(I_{147})

where the meaning of the respective substituents $R_1$ and $R_3$ are given in Table A, thus disclosing 412 specific compounds of the formula $I_{147}$.

Table 148: A further preferred group of compounds of the formula I has the formula

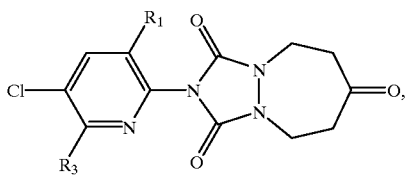

(I_{148})

where the meaning of the respective substituents $R_1$ and $R_3$ are given in Table A, thus disclosing 412 specific compounds of the formula $I_{148}$.

Table 149: A further preferred group of compounds of the formula I has the formula

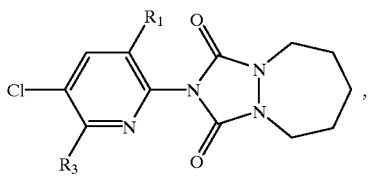

(I_{149})

where the meaning of the respective substituents $R_1$ and $R_3$ are given in Table A, thus disclosing 412 specific compounds of the formula $I_{149}$.

Table 150: A further preferred group of compounds of the formula I has the formula

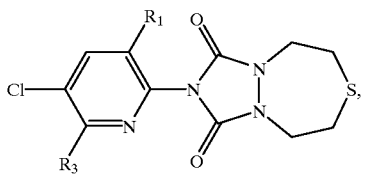

(I_{150})

where the meaning of the respective substituents $R_1$ and $R_3$ are given in Table A, thus disclosing 412 specific compounds of the formula $I_{150}$.

Table 151: A further preferred group of compounds of the formula I has the formula

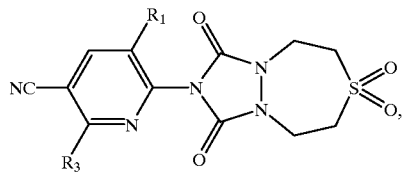

(I_{151})

where the meaning of the respective substituents $R_1$ and $R_3$ are given in Table A, thus disclosing 412 specific compounds of the formula $I_{151}$.

Table 152: A further preferred group of compounds of the formula I has the formula

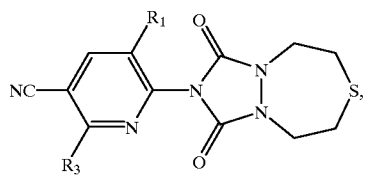

(I_{152})

where the meaning of the respective substituents $R_1$ and $R_3$ are given in Table A, thus disclosing 412 specific compounds of the formula $I_{152}$.

Table 153: A further preferred group of compounds of the formula I has the formula

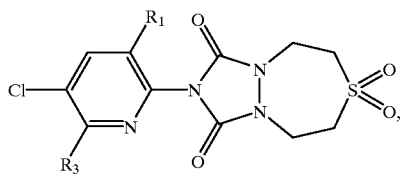

(I_{153})

where the meaning of the respective substituents $R_1$ and $R_3$ are given in Table A, thus disclosing 412 specific compounds of the formula $I_{153}$.

Table 154: A further preferred group of compounds of the formula I has the formula

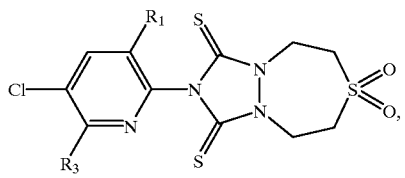

(I_{154})

where the meaning of the respective substituents $R_1$ and $R_3$ are given in Table A, thus disclosing 412 specific compounds of the formula $I_{154}$.

Table 155: A further preferred group of compounds of the formula I has the formula

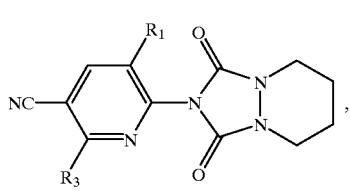

(I₁₅₅)

where the meaning of the respective substituents $R_1$ and $R_3$ are given in Table A, thus disclosing 412 specific compounds of the formula $I_{155}$.

Table 156: A further preferred group of compounds of the formula I has the formula

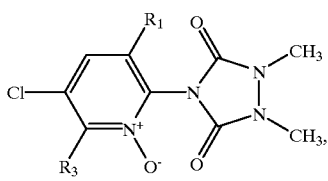

(I₁₅₆)

where the meaning of the respective substituents $R_1$ and $R_3$ are given in Table A, thus disclosing 412 specific compounds of the formula $I_{156}$.

Table 157: A further preferred group of compounds of the formula I has the formula

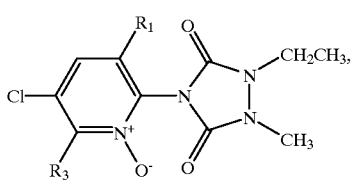

(I₁₅₇)

where the meaning of the respective substituents $R_1$ and $R_3$ are given in Table A, thus disclosing 412 specific compounds of the formula $I_{157}$.

Table 158: A further preferred group of compounds of the formula I has the formula

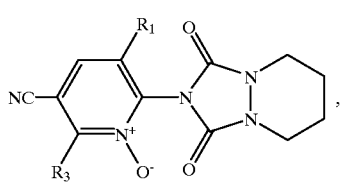

(I₁₅₈)

where the meaning of the respective substituents $R_1$ and $R_3$ are given in Table A, thus disclosing 412 specific compounds of the formula $I_{158}$.

Table 159: A further preferred group of compounds of the formula I has the formula

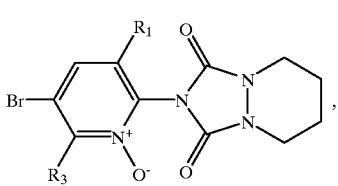

(I₁₅₉)

where the meaning of the respective substituents $R_1$ and $R_3$ are given in Table A, thus disclosing 412 specific compounds of the formula $I_{159}$.

Table 160: A further preferred group of compounds of the formula I has the formula

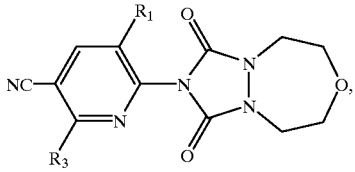

(I₁₆₀)

where the meaning of the respective substituents $R_1$ and $R_3$ are given in Table A, thus disclosing 412 specific compounds of the formula $I_{160}$.

Table 161: A further preferred group of compounds of the formula I has the formula

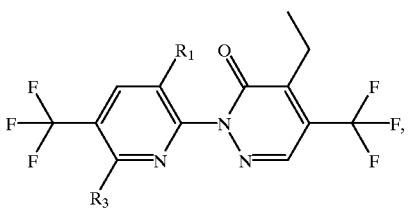

(I₁₆₁)

where the meaning of the respective substituents $R_1$ and $R_3$ are given in Table A, thus disclosing 412 specific compounds of the formula $I_{161}$.

Table 162: A further preferred group of compounds of the formula I has the formula

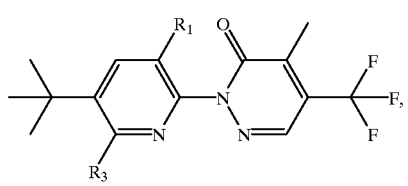

(I₁₆₂)

where the meaning of the respective substituents $R_1$ and $R_3$ are given in Table A, thus disclosing 412 specific compounds of the formula $I_{162}$.

Table 163: A further preferred group of compounds of the formula I has the formula

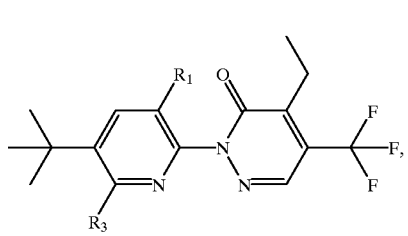
(I₁₆₃)

where the meaning of the respective substituents $R_1$ and $R_3$ are given in Table A, thus disclosing 412 specific compounds of the formula $I_{163}$.

Table 164: A further preferred group of compounds of the formula I has the formula

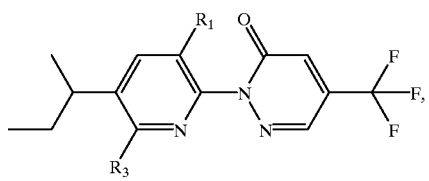
(I₁₆₄)

where the meaning of the respective substituents $R_1$ and $R_3$ are given in Table A, thus disclosing 412 specific compounds of the formula $I_{164}$.

Table 165: A further preferred group of compounds of the formula I has the formula

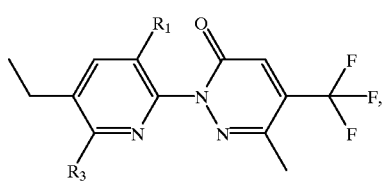
(I₁₆₅)

where the meaning of the respective substituents $R_1$ and $R_3$ are given in Table A, thus disclosing 412 specific compounds of the formula $I_{165}$.

Table 166: A further preferred group of compounds of the formula I has the formula

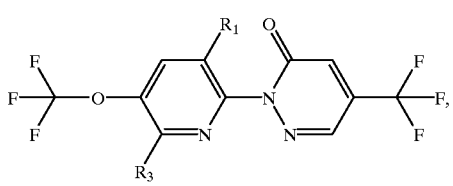
(I₁₆₆)

where the meaning of the respective substituents $R_1$ and $R_3$ are given in Table A, thus disclosing 412 specific compounds of the formula $I_{166}$.

Table 167: A further preferred group of compounds of the formula I has the formula

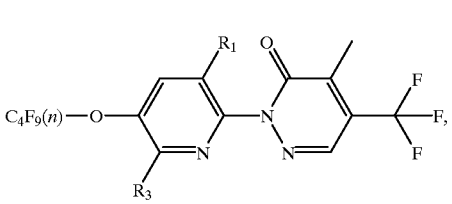
(I₁₆₇)

where the meaning of the respective substituents $R_1$ and $R_3$ are given in Table A, thus disclosing 412 specific compounds of the formula $I_{167}$.

Table 168: A further preferred group of compounds of the formula I has the formula

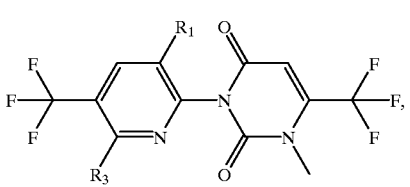
(I₁₆₈)

where the meaning of the respective substituents $R_1$ and $R_3$ are given in Table A, thus disclosing 412 specific compounds of the formula $I_{168}$.

Table 169: A further preferred group of compounds of the formula I has the formula

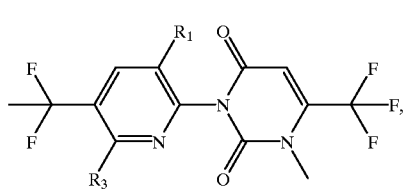
(I₁₆₉)

where the meaning of the respective substituents $R_1$ and $R_3$ are given in Table A, thus disclosing 412 specific compounds of the formula $I_{169}$.

Table 170: A further preferred group of compounds of the formula I has the formula

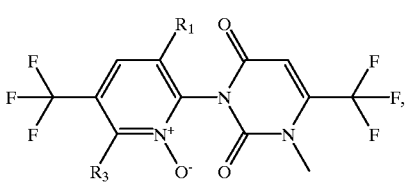
(I₁₇₀)

where the meaning of the respective substituents $R_1$ and $R_3$ are given in Table A, thus disclosing 412 specific compounds of the formula $I_{170}$.

Table 171: A further preferred group of compounds of the formula I has the formula

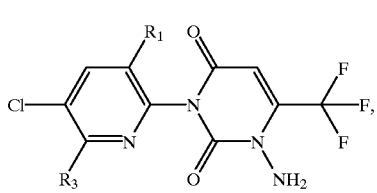

(I₁₇₁)

where the meaning of the respective substituents $R_1$ and $R_3$ are given in Table A, thus disclosing 412 specific compounds of the formula $I_{171}$.

Table 172: A further preferred group of compounds of the formula I has the formula

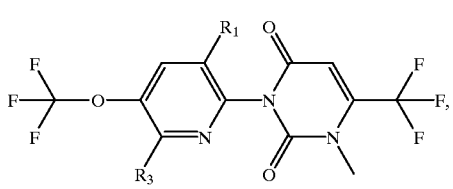

(I₁₇₂)

where the meaning of the respective substituents $R_1$ and $R_3$ are given in Table A, thus disclosing 412 specific compounds of the formula $I_{172}$.

Table 173: A further preferred group of compounds of the formula I has the formula

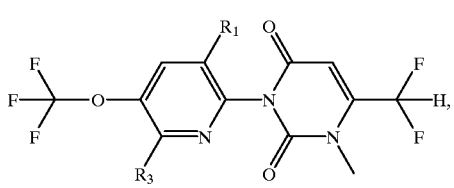

(I₁₇₃)

where the meaning of the respective substituents $R_1$ and $R_3$ are given in Table A, thus disclosing 412 specific compounds of the formula $I_{173}$.

Table 174: A further preferred group of compounds of the formula I has the formula

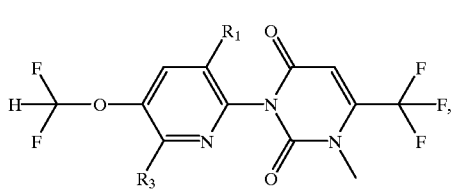

(I₁₇₄)

where the meaning of the respective substituents $R_1$ and $R_3$ are given in Table A, thus disclosing 412 specific compounds of the formula $I_{174}$.

Table 175: A further preferred group of compounds of the formula I has the formula

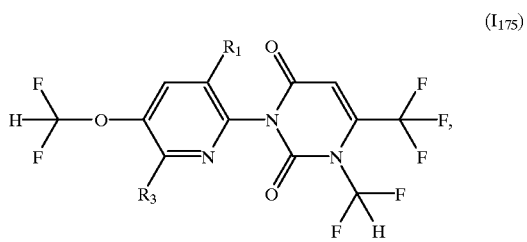

(I₁₇₅)

where the meaning of the respective substituents $R_1$ and $R_3$ are given in Table A, thus disclosing 412 specific compounds of the formula $I_{175}$.

Table 176: A further preferred group of compounds of the formula I has the formula

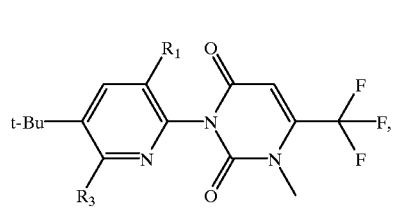

(I₁₇₆)

where the meaning of the respective substituents $R_1$ and $R_3$ are given in Table A, thus disclosing 412 specific compounds of the formula $I_{176}$.

Table 177: A further preferred group of compounds of the formula I has the formula

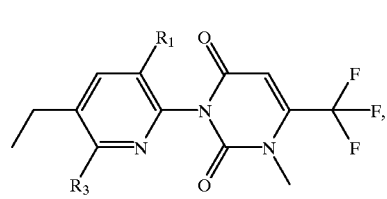

(I₁₇₇)

where the meaning of the respective substituents $R_1$ and $R_3$ are given in Table A, thus disclosing 412 specific compounds of the formula $I_{177}$.

Table 178: A further preferred group of compounds of the formula I has the formula

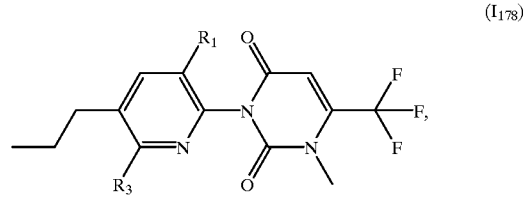

(I₁₇₈)

where the meaning of the respective substituents $R_1$ and $R_3$ are given in Table A, thus disclosing 412 specific compounds of the formula $I_{178}$.

Table 179: A further preferred group of compounds of the formula I has the formula

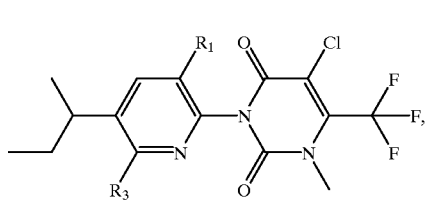

(I$_{179}$)

where the meaning of the respective substituents R$_1$ and R$_3$ are given in Table A, thus disclosing 412 specific compounds of the formula I$_{179}$.

Table 180: A further preferred group of compounds of the formula I has the formula

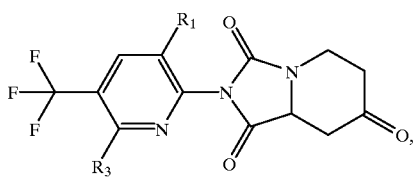

(I$_{180}$)

where the meaning of the respective substituents R$_1$ and R$_3$ are given in Table A, thus disclosing 412 specific compounds of the formula I$_{180}$.

Table 181: A further preferred group of compounds of the formula I has the formula

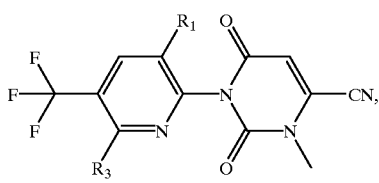

(I$_{181}$)

where the meaning of the respective substituents R$_1$ and R$_3$ are given in Table A, thus disclosing 412 specific compounds of the formula I$_{181}$.

Table 182: A further preferred group of compounds of the formula I has the formula

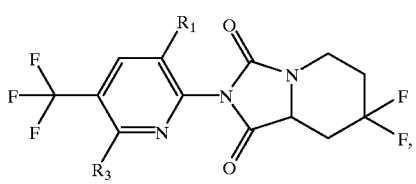

(I$_{182}$)

where the meaning of the respective substituents R$_1$ and R$_3$ are given in Table A, thus disclosing 412 specific compounds of the formula I$_{182}$.

Table 183: A further preferred group of compounds of the formula I has the formula

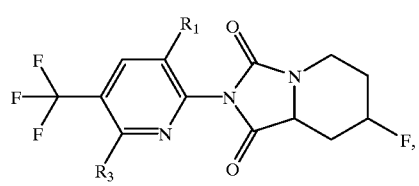

(I$_{183}$)

where the meaning of the respective substituents R$_1$ and R$_3$ are given in Table A, thus disclosing 412 specific compounds of the formula I$_{183}$.

Table 184: A further preferred group of compounds of the formula I has the formula

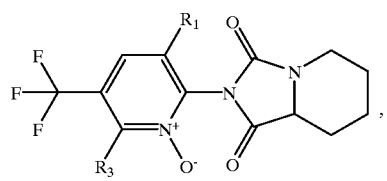

(I$_{184}$)

where the meaning of the respective substituents R$_1$ and R$_3$ are given in Table A, thus disclosing 412 specific compounds of the formula I$_{184}$.

Table 185: A further preferred group of compounds of the formula I has the formula

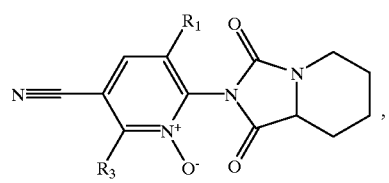

(I$_{185}$)

where the meaning of the respective substituents R$_1$ and R$_3$ are given in Table A, thus disclosing 412 specific compounds of the formula I$_{185}$.

Table 186: A further preferred group of compounds of the formula I has the formula

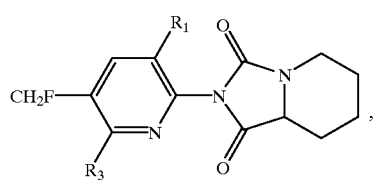

(I$_{186}$)

where the meaning of the respective substituents R$_1$ and R$_3$ are given in Table A, thus disclosing 412 specific compounds of the formula I$_{186}$.

Table 187: A further preferred group of compounds of the formula I has the formula

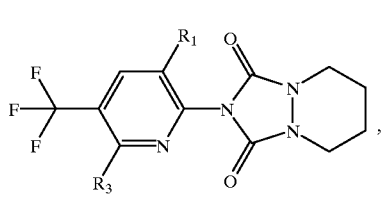

(I₁₈₇)

where the meaning of the respective substituents $R_1$ and $R_3$ are given in Table A, thus disclosing 412 specific compounds of the formula $I_{187}$.

Table 188: A further preferred group of compounds of the formula I has the formula

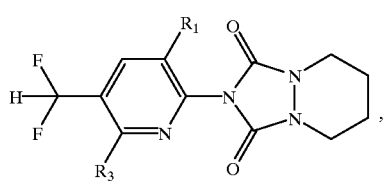

(I₁₈₈)

where the meaning of the respective substituents $R_1$ and $R_3$ are given in Table A, thus disclosing 412 specific compounds of the formula $I_{188}$.

Table 189: A further preferred group of compounds of the formula I has the formula

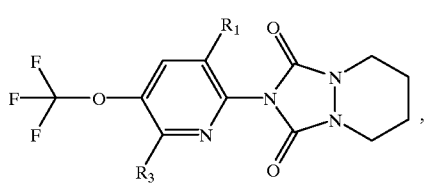

(I₁₈₉)

where the meaning of the respective substituents $R_1$ and $R_3$ are given in Table A, thus disclosing 412 specific compounds of the formula $I_{189}$.

Table 190: A further preferred group of compounds of the formula I has the formula

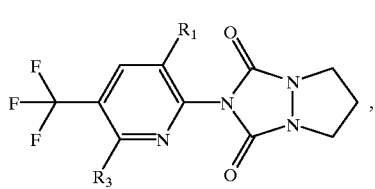

(I₁₉₀)

where the meaning of the respective substituents $R_1$ and $R_3$ are given in Table A, thus disclosing 412 specific compounds of the formula $I_{190}$.

Table 191: A further preferred group of compounds of the formula I has the formula

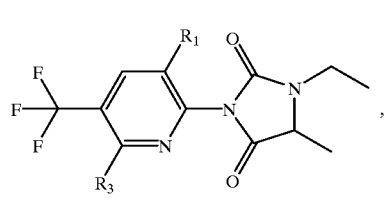

(I₁₉₁)

where the meaning of the respective substituents $R_1$ and $R_3$ are given in Table A, thus disclosing 412 specific compounds of the formula $I_{191}$.

Table 192: A further preferred group of compounds of the formula I has the formula

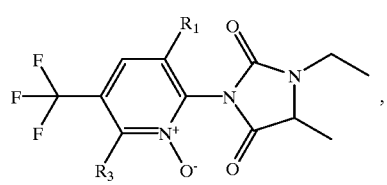

(I₁₉₂)

where the meaning of the respective substituents $R_1$ and $R_3$ are given in Table A, thus disclosing 412 specific compounds of the formula $I_{192}$.

Table 193: A further preferred group of compounds of the formula I has the formula

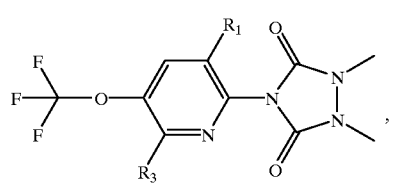

(I₁₉₃)

where the meaning of the respective substituents $R_1$ and $R_3$ are given in Table A, thus disclosing 412 specific compounds of the formula $I_{193}$.

Table 194: A further preferred group of compounds of the formula I has the formula

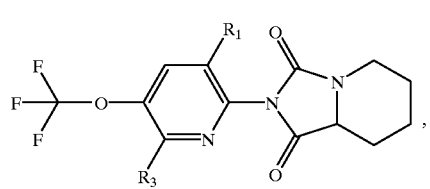

(I₁₉₄)

where the meaning of the respective substituents $R_1$ and $R_3$ are given in Table A, thus disclosing 412 specific compounds of the formula $I_{194}$.

TABLE A

| Comp. No. | R₁ | R₃ |
|---|---|---|
| .001 | F | NH$_2$ |
| .002 | F | OH |
| .003 | F | SH |
| .004 | F | SO$_2$Cl |
| .005 | F | NH(CH$_3$) |
| .006 | F | N(CH$_2$CH$_3$)$_2$ |
| .007 | F | NH(COCH$_3$) |
| .008 | F | NH(CH$_2$CH=CH$_2$) |
| .009 | F | N(CH$_3$)(CH$_2$C≡CH) |
| .010 | F | N(SO$_2$CH$_3$)$_2$ |
| .011 | F | NH(SO$_2$CH$_2$CH$_3$) |
| .012 | F | N(CH$_2$CH=CH$_2$)(SO$_2$CH$_2$CH$_3$) |
| .013 | F | N(CH$_2$C≡CH)(SO$_2$CH(CH$_3$)$_2$) |
| .014 | F | N(CH$_2$CF$_3$)(CHO) |
| .015 | F | NH(CH$_2$C$_6$H$_5$) |
| .016 | F | OCH$_3$ |
| .017 | F | OCH$_2$CH$_3$ |
| .018 | F | OCH(CH$_3$)$_2$ |
| .019 | F | OCH(CH$_3$)CH$_2$CH$_2$CH$_3$ |
| .020 | F | OCH$_2$CH=CH$_2$ |
| .021 | F | OCH(CH$_3$)CH=CH$_2$ |
| .022 | F | OCH$_2$C≡CH |
| .023 | F | OCH(CH$_3$)C≡CH |
| .024 | F | OCH(cyclopentyl)$_2$ |
| .025 | F | OCH$_2$OCH$_2$C$_6$H$_5$ |
| .026 | F | OCH$_2$(C$_6$H$_5$) |
| .027 | F | OCH$_2$(2-F—C$_6$H$_5$) |
| .028 | F | OCH(CH$_3$)(4-CH$_3$—C$_6$H$_5$) |
| .029 | F | OC$_6$H$_5$ |
| .030 | F | O(4-pyrimidyl) |
| .031 | F | OCH$_2$CH$_2$Cl |
| .032 | F | OCH$_2$CH=CHCl |
| .033 | F | OCH$_2$CH$_2$OH |
| .034 | F | OCH$_2$OCH$_3$ |
| .035 | F | OCH$_2$CH$_2$OCH$_2$CH$_3$ |
| .036 | F | OCH$_2$CH$_2$OCH$_2$CH$_2$OCH$_2$CH$_3$ |
| .037 | F | OCH(CH$_3$)CH$_2$OCH$_2$CH=CH$_2$ |
| .038 | F | OCOCH$_3$ |
| .039 | F | OCOOCH$_3$ |
| .040 | F | OCOCH$_2$C$_6$H$_5$ |
| .041 | F | OCH$_2$SCH$_3$ |
| .042 | F | OCH$_2$CH$_2$SCH$_2$CH$_3$ |
| .043 | F | OCH$_2$COOH |
| .044 | F | OCH(CH$_3$)COOH |
| .045 | F | (R)-OCH(CH$_3$)COOH |
| .046 | F | (S)-OCH(CH$_3$)COOH |
| .047 | F | OCH$_2$COOCH$_2$CH$_3$ |
| .048 | F | OCH(CH$_3$)COOCH$_3$ |
| .049 | F | OCH(CH$_3$)COOCH$_2$CH=CH$_2$ |
| .050 | F | OCH(CH$_3$)COOCH$_2$(C$_6$H$_5$) |
| .051 | F | OCH(CH$_3$)CH$_2$COOH |
| .052 | F | OCH(CH$_3$)CH$_2$COOCH$_2$CH$_3$ |
| .053 | F | OCH$_2$COSCH$_3$ |
| .054 | F | OCH(CH$_3$)COSCH$_2$CH$_3$ |
| .055 | F | OCH(CH$_3$)COSCH(CH$_3$)$_2$ |
| .056 | F | OCH$_2$CONH$_2$ |
| .057 | F | OCH$_2$CON(CH$_2$CH$_3$)$_2$ |
| .058 | F | OCH(CH$_3$)CON(CH$_3$)$_2$ |
| .059 | F | OCH(CH$_3$)CONH(CH$_2$CH=CH$_2$) |
| .060 | F | OCH(CH$_3$)CON(CH$_3$)(CH$_2$C≡CH) |
| .061 | F | OCH(CH$_3$)CON(CH$_2$C$_6$H$_5$)$_2$ |
| .062 | F | OCH(CH$_3$)CON(CH$_3$)(C$_6$H$_5$) |
| .063 | F | OCH$_2$COOCH$_2$CH$_2$SCH$_3$ |
| .064 | F | OCH(CH(CH$_3$)$_2$)COOH |
| .065 | F | OCH(CH$_3$)COOCH$_2$CH$_2$OCH$_2$CH$_3$ |
| .066 | F | OCH(C$_6$H$_5$)COOH |
| .067 | F | (R)-OCH(C$_6$H$_5$)COOH |
| .068 | F | (S)-OCH(C$_6$H$_5$)COOH |
| .069 | F | OCH(C$_6$H$_5$)COOCH$_3$ |
| .070 | F | OCH(C$_6$H$_5$)COOCH(CH$_3$)C≡CH |
| .071 | F | OCH(C$_6$H$_5$)COOCH$_2$C$_6$H$_5$ |
| .072 | F | OCH(C$_6$H$_5$)COSCH(CH$_3$)$_2$ |
| .073 | F | OCH(C$_6$H$_5$)CONH$_2$ |
| .074 | F | OCH(C$_6$H$_5$)CONH(CH$_2$C≡CH) |
| .075 | F | OCH(C$_6$H$_5$)CON(CH$_2$CH=CH$_2$)$_2$ |
| .076 | F | OCH(C$_6$H$_5$)CON(CH$_3$)CH$_2$C$_6$H$_5$ |
| .077 | F | OCH(C$_6$H$_5$)CONH(CH$_2$(2-F—C$_6$H$_5$)) |
| .078 | F | OCH(C$_6$H$_5$)CONH(cyclopropyl) |
| .079 | F | OCH$_2$CH$_2$COOH |
| .080 | F | OCH$_2$CH$_2$COOCH$_2$CH$_3$ |
| .081 | F | OCH(CH$_3$)CH$_2$COOH |
| .082 | F | SCH$_3$ |
| .083 | F | SCH(CH$_3$)$_2$ |
| .084 | F | SCH$_2$CH=CH$_2$ |
| .085 | F | SCH$_2$C$_6$H$_5$ |
| .086 | F | SCH$_2$CH$_2$OCH$_3$ |
| .087 | F | SC$_6$H$_5$ |
| .088 | F | SCH$_2$COOH |
| .089 | F | SCH$_2$COOCH$_2$C$_6$H$_5$ |
| .090 | F | SCH(CH$_3$)COOH |
| .091 | F | SCH(CH$_3$)COOCH$_3$ |
| .092 | F | SCH(CH$_3$)COOCH$_2$CH=CH$_2$ |
| .093 | F | SCH(CH$_3$)COSCH$_3$ |
| .094 | F | SCH(CH$_3$)CON(CH$_3$)$_2$ |
| .095 | F | SCH(CH$_3$)CONH(CH$_2$CH=CH$_2$) |
| .096 | F | SOCH$_2$CH$_3$ |
| .097 | F | SO$_2$CH$_3$ |
| .098 | F | SO$_2$NH$_2$ |
| .099 | F | SO$_2$N(CH$_3$)$_2$ |
| .100 | F | SO$_2$N(CH$_2$CH$_3$)$_2$ |
| .101 | F | SO$_2$N(CH$_3$)(CH$_2$(4-CH$_3$—C$_6$H$_5$)) |
| .102 | F | SO$_2$NHCH$_2$CH$_2$OCH$_3$ |
| .103 | F | SCOOCH$_3$ |
| .104 | F | SCON(CH$_3$)$_2$ |
| .105 | F | SCONHCH$_2$CH=CH$_2$ |
| .106 | F | SCOOCH$_2$CHCH$_2$ |
| .107 | F | SCON(CH$_2$CH$_3$)COCF$_3$ |
| .108 | Cl | NH$_2$ |
| .109 | Cl | OH |
| .110 | Cl | SH |
| .111 | Cl | SO$_2$Cl |
| .112 | Cl | NH(CH$_3$) |
| .113 | Cl | N(CH$_2$CH$_3$)$_2$ |
| .114 | Cl | NH(COCH$_3$) |
| .115 | Cl | NH(CH$_2$CH=CH$_2$) |
| .116 | Cl | N(CH$_3$)(CH$_2$C≡CH) |
| .117 | Cl | N(SO$_2$CH$_3$)$_2$ |
| .118 | Cl | NH(SO$_2$CH$_2$CH$_3$) |
| .119 | Cl | N(CH$_2$CH=CH$_2$)(SO$_2$CH$_2$CH$_3$) |
| .120 | Cl | N(CH$_2$C≡CH)(SO$_2$CH(CH$_3$)$_2$) |
| .121 | Cl | N(CH$_2$CF$_3$)(CHO) |
| .122 | Cl | NH(CH$_2$C$_6$H$_5$) |
| .123 | Cl | OCH$_3$ |
| .124 | Cl | OCH$_2$CH$_3$ |
| .125 | Cl | OCH(CH$_3$)$_2$ |
| .126 | Cl | OCH(CH$_3$)CH$_2$CH$_2$CH$_3$ |
| .127 | Cl | OCH$_2$CH=CH$_2$ |
| .128 | Cl | OCH(CH$_3$)CH=CH$_2$ |
| .129 | Cl | OCH$_2$C≡CH |
| .130 | Cl | OCH(CH$_3$)C≡CH |
| .131 | Cl | OCH(cyclopentyl) |
| .132 | Cl | OCH$_2$(C$_6$H$_5$) |
| .133 | Cl | OCH$_2$(2-F—C$_6$H$_5$) |
| .134 | Cl | OCH(CH$_3$)(4-CH$_3$—C$_6$H$_5$) |
| .135 | Cl | OC$_6$H$_5$ |
| .136 | Cl | O(4-pyrimidyl) |
| .137 | Cl | OCH$_2$CH$_2$Cl |
| .138 | Cl | OCH$_2$CH=CHCl |
| .139 | Cl | OCH$_2$CH$_2$OH |
| .140 | Cl | OCH$_2$OCH$_3$ |
| .141 | Cl | OCH$_2$CH$_2$OCH$_2$CH$_3$ |
| .142 | Cl | OCH$_2$CH$_2$OCH$_2$CH$_2$OCH$_2$CH$_3$ |
| .143 | Cl | OCH(CH$_3$)CH$_2$OCH$_2$CH=CH$_2$ |
| .144 | Cl | OCOCH$_3$ |
| .145 | Cl | OCOOCH$_3$ |
| .146 | Cl | OCOCH$_2$C$_6$H$_5$ |
| .147 | Cl | OCH$_2$SCH$_3$ |
| .148 | Cl | OCH$_2$CH$_2$SCH$_2$CH$_3$ |
| .149 | Cl | OCH$_2$COOH |
| .150 | Cl | OCH(CH$_3$)COOH |
| .151 | Cl | (R)-OCH(CH$_3$)COOH |
| .152 | Cl | (S)-OCH(CH$_3$)COOH |
| .153 | Cl | OCH$_2$COOCH$_2$CH$_3$ |
| .154 | Cl | OCH(CH$_3$)COOCH$_3$ |

TABLE A-continued

| Comp. No. | $R_1$ | $R_3$ |
|---|---|---|
| .155 | Cl | $OCH(CH_3)COOCH_2CH=CH_2$ |
| .156 | Cl | $OCH(CH_3)COOCH_2(C_6H_5)$ |
| .157 | Cl | $OCH(CH_3)CH_2COOH$ |
| .158 | Cl | $OCH(CH_3)CH_2COOCH_2CH_3$ |
| .159 | Cl | $OCH_2COSCH_3$ |
| .160 | Cl | $OCH(CH_3)COSCH_2CH_3$ |
| .161 | Cl | $OCH(CH_3)COSCH(CH_3)_2$ |
| .162 | Cl | $OCH_2CONH_2$ |
| .163 | Cl | $OCH_2CON(CH_2CH_3)_2$ |
| .164 | Cl | $OCH(CH_3)CON(CH_3)_2$ |
| .165 | Cl | $OCH(CH_3)CONH(CH_2CH=CH_2)$ |
| .166 | Cl | $OCH(CH_3)CON(CH_3)(CH_2C\equiv CH)$ |
| .167 | Cl | $OCH(CH_3)CON(CH_2C_6H_5)_2$ |
| .168 | Cl | $OCH(CH_3)CON(CH_3)(C_6H_5)$ |
| .169 | Cl | $OCH_2COOCH_2CH_2SCH_3$ |
| .170 | Cl | $OCH(CH(CH_3)_2)COOH$ |
| .171 | Cl | $OCH(CH_3)COOCH_2CH_2OCH_2CH_3$ |
| .172 | Cl | $OCH(C_6H_5)COOH$ |
| .173 | Cl | $(R)-OCH(C_6H_5)COOH$ |
| .174 | Cl | $(S)-OCH(C_6H_5)COOH$ |
| .175 | Cl | $OCH(C_6H_5)COOCH_3$ |
| .176 | Cl | $OCH(C_6H_5)COOCH(CH_3)C\equiv CH$ |
| .177 | Cl | $OCH(C_6H_5)COOCH_2C_6H_5$ |
| .178 | Cl | $OCH(C_6H_5)COSCH(CH_3)_2$ |
| .179 | Cl | $OCH(C_6H_5)CONH_2$ |
| .180 | Cl | $OCH(C_6H_5)CONH(CH_2C\equiv CH)$ |
| .181 | Cl | $OCH(C_6H_5)CON(CH_2CH=CH_2)_2$ |
| .182 | Cl | $OCH(C_6H_5)CON(CH_3)CH_2C_6H_5$ |
| .183 | Cl | $OCH(C_6H_5)CONH(CH_2(2-F-C_6H_5))$ |
| .184 | Cl | $OCH(C_6H_5)CONH(cyclopropyl)$ |
| .185 | Cl | $OCH_2CH_2COOH$ |
| .186 | Cl | $OCH_2CH_2COOCH_2CH_3$ |
| .187 | Cl | $OCH(CH_3)CH_2COOH$ |
| .188 | Cl | $SCH_3$ |
| .189 | Cl | $SCH(CH_3)_2$ |
| .190 | Cl | $SCH_2CH=CH_2$ |
| .191 | Cl | $SCH_2C_6H_5$ |
| .192 | Cl | $SCH_2CH_2OCH_3$ |
| .193 | Cl | $SC_6H_5$ |
| .194 | Cl | $SCH_2COOH$ |
| .195 | Cl | $SCH_2COOCH_2C_6H_5$ |
| .196 | Cl | $SCH(CH_3)COOH$ |
| .197 | Cl | $SCH(CH_3)COOCH_2CH_3$ |
| .198 | Cl | $SCH(CH_3)COOCH_2CH=CH_2$ |
| .199 | Cl | $SCH(CH_3)COSCH_3$ |
| .200 | Cl | $SCH(CH_3)CON(CH_3)_2$ |
| .201 | Cl | $SCH(CH_3)CONH(CH_2CH=CH_2)$ |
| .202 | Cl | $SOCH_2CH_3$ |
| .203 | Cl | $SO_2CH_3$ |
| .204 | Cl | $SO_2NH_2$ |
| .205 | Cl | $SO_2N(CH_3)_2$ |
| .206 | Cl | $SO_2N(CH_2CH_3)_2$ |
| .207 | Cl | $SO_2N(CH_3)(CH_2(4-CH_3-C_6H_5))$ |
| .208 | Cl | $SO_2NHCH_2CH_2OCH_3$ |
| .209 | Cl | $SCOOCH_3$ |
| .210 | Cl | $SCON(CH_3)_2$ |
| .211 | Cl | $SCONHCH_2CH=CH_2$ |
| .212 | Cl | $SCOOCH_2CH=CH_2$ |
| .213 | Cl | $SCON(CH_2CH_3)COCF_3$ |
| .214 | H | $NH_2$ |
| .215 | H | $OH$ |
| .216 | H | $SH$ |
| .217 | H | $SO_2Cl$ |
| .218 | H | $NH(CH_2C_6H_5)$ |
| .219 | H | $N(CH_2CH=CH_2)_2$ |
| .220 | H | $N(SO_2CH_3)_2$ |
| .221 | H | $NH(SO_2CH_2CH_3)$ |
| .222 | H | $NH(COCH_3)$ |
| .223 | H | $OCH_3$ |
| .224 | H | $OCH_2CH_3$ |
| .225 | H | $OCH_2CH=CH_2$ |
| .226 | H | $OCH_2C\equiv CH$ |
| .227 | H | $OCH_2C_6H_5$ |
| .228 | H | $OCH_2CH_2Cl$ |
| .229 | H | $OCH_2CH_2OH$ |
| .230 | H | $OCH_2OCH_3$ |
| .231 | H | $OCH_2CH_2OCH_2CH_3$ |
| .232 | H | $OCH_2CH_2OCH_2CH_2OCH_3$ |
| .233 | H | $OCOCH_3$ |
| .234 | H | $OCOOCH_3$ |
| .235 | H | $OCH_2SCH_3$ |
| .236 | H | $OCH_2CH_2SCH_3$ |
| .237 | H | $OCH_2COOH$ |
| .238 | H | $OCH_2COOCH_3$ |
| .239 | H | $OCH_2COOCH_2C_6H_5$ |
| .240 | H | $OCH_2CONH(CH_3)$ |
| .241 | H | $OCH(CH_3)COOH$ |
| .242 | H | $OCH(CH_3)COOCH_2CH_3$ |
| .243 | H | $OCH(CH_3)COOCH_2CH=CH_2$ |
| .244 | H | $OCH(CH_3)COOCH_2C_6H_5$ |
| .245 | H | $OCH(CH_3)CONH_2$ |
| .246 | H | $OCH(CH_3)CONH(CH_2CH=CH_2)$ |
| .247 | H | $OCH(CH_3)CON(CH_3)_2$ |
| .248 | H | $OCH(CH_3)COSCH(CH_3)_2$ |
| .249 | H | $OCH(C_6H_5)COOH$ |
| .250 | H | $OCH(C_6H_5)COOCH_3$ |
| .251 | H | $OCH(C_6H_5)COOCH_2CH=CH_2$ |
| .252 | H | $OCH(C_6H_5)CONH_2$ |
| .253 | H | $OCH(C_6H_5)CONH(CH_2CH_3)$ |
| .254 | H | $OCH(C_6H_5)CON(CH_3)_2$ |
| .255 | H | $OCH(C_6H_5)COSCH_3$ |
| .256 | H | $OCH(C_6H_5)COSCH(CH_3)_2$ |
| .257 | H | $OCH(CH_3)CH_2COOH$ |
| .258 | H | $OCH(CH_3)CH_2COOCH_2CH_3$ |
| .259 | H | $SCH_3$ |
| .260 | H | $SCH(CH_3)_2$ |
| .261 | H | $SCH_2C_6H_5$ |
| .262 | H | $SCH(CH_3)COOH$ |
| .263 | H | $SCH(CH_3)COOCH_2CH_3$ |
| .264 | H | $SO_2NH_2$ |
| .265 | H | $SO_2NH(CH_2CH=CH_2)$ |
| .266 | H | $SO_2N(CH_3)_2$ |
| .267 | H | $SCOCH_3$ |
| .268 | H | $SCOOCH_2CH_3$ |
| .269 | $CH_3$ | $NH_2$ |
| .270 | $CH_3$ | $OH$ |
| .271 | $CH_3$ | $SH$ |
| .272 | $CH_3$ | $SO_2C$ |
| .273 | $CH_3$ | $NH(CH_2C_6H_5)$ |
| .274 | $CH_3$ | $N(CH_2CH=CH_2)_2$ |
| .275 | $CH_3$ | $N(SO_2CH_3)_2$ |
| .276 | $CH_3$ | $NH(SO_2CH_2CH_3)$ |
| .277 | $CH_3$ | $NH(COCH_3)$ |
| .278 | $CH_3$ | $OCH_3$ |
| .279 | $CH_3$ | $OCH_2CH_3$ |
| .280 | $CH_3$ | $OCH_2CH=CH_2$ |
| .281 | $CH_3$ | $OCH_2C\equiv CH$ |
| .282 | $CH_3$ | $OCH_2C_6H_5$ |
| .283 | $CH_3$ | $OCH_2CH_2Cl$ |
| .284 | $CH_3$ | $OCH_2CH_2OH$ |
| .285 | $CH_3$ | $OCH_2OCH_3$ |
| .286 | $CH_3$ | $OCH_2CH_2OCH_2CH_3$ |
| .287 | $CH_3$ | $OCH_2CH_2OCH_2CH_2OCH_3$ |
| .288 | $CH_3$ | $OCOCH_3$ |
| .289 | $CH_3$ | $OCOOCH_3$ |
| .290 | $CH_3$ | $OCH_2SCH_3$ |
| .291 | $CH_3$ | $OCH_2CH_2SCH_3$ |
| .292 | $CH_3$ | $OCH_2COOH$ |
| .293 | $CH_3$ | $OCH_2COOCH_3$ |
| .294 | $CH_3$ | $OCH_2COOCH_2C_6H_5$ |
| .295 | $CH_3$ | $OCH_2CONH(CH_3)$ |
| .296 | $CH_3$ | $OCH(CH_3)COOH$ |
| .297 | $CH_3$ | $OCH(CH_3)COOCH_2CH_3$ |
| .298 | $CH_3$ | $OCH(CH_3)COOCH_2CH=CH_2$ |
| .299 | $CH_3$ | $OCH(CH_3)COOCH_2C_6H_5$ |
| .300 | $CH_3$ | $OCH(CH_3)CONH_2$ |
| .301 | $CH_3$ | $OQH(CH_3)CONH(CH_2CH=CH_2)$ |
| .302 | $CH_3$ | $OCH(CH_3)CON(CH_3)_2$ |
| .303 | $CH_3$ | $OCH(CH_3)COSCH(CH_3)_2$ |
| .304 | $CH_3$ | $OCH(C_6H_5)COOH$ |
| .305 | $CH_3$ | $OCH(C_6H_5)COOCH_3$ |
| .306 | $CH_3$ | $OCH(C_6H_5)COOCH_2CH=CH_2$ |
| .307 | $CH_3$ | $OCH(C_6H_5)CONH_2$ |
| .308 | $CH_3$ | $OCH(C_6H_5)CONH(CH_2CH_3)$ |

TABLE A-continued

| Comp. No. | R₁ | R₃ |
|---|---|---|
| .309 | CH₃ | OCH(C₆H₅)CON(CH₃)₂ |
| .310 | CH₃ | OCH(C₆H₅)COSCH₃ |
| .311 | CH₃ | OCH(C₆H₅)COSCH(CH₃)₂ |
| .312 | CH₃ | OCH(CH₃)CH₂COOH |
| .313 | CH₃ | OCH(CH₃)CH₂COOCH₂CH₃ |
| .314 | CH₃ | SCH₃ |
| .315 | CH₃ | SCH(CH₃)₂ |
| .316 | CH₃ | SCH₂C₆H₅ |
| .317 | CH₃ | SCH(CH₃)COOH |
| .318 | CH₃ | SCH(CH₃)COOCH₂CH₃ |
| .319 | CH₃ | SO₂NH₂ |
| .320 | CH₃ | SO₂NH(CH₂CH=CH₂) |
| .321 | CH₃ | SO₂N(CH₃)₂ |
| .322 | CH₃ | SCOCH₃ |
| .323 | CH₃ | SCOOCH₂CH₃ |
| .324 | H | N-imidazolyl |
| .325 | F | N-imidazolyl |
| .326 | Cl | N-imidazolyl |
| .327 | CH₃ | N-imidazolyl |
| .328 | F | N-1,2,4-triazol-1-yl |
| .329 | F | N-1,2,4-triazol-4-yl |
| .330 | F | N-1,2,3-triazol-1-yl |
| .331 | Cl | N-1,2,4-triazol-1-yl |
| .332 | Cl | N-1,2,4-triazol-4-yl |
| .333 | Cl | N-1,2,3-triazol-1-yl |
| .334 | Cl | N-pyrrolidinyl |
| .335 | F | N-pyrrolidinyl |
| .336 | F | N-pipendinyl |
| .337 | F | N-(4-methyl-piperazinyl) |
| .338 | Cl | N-pyrazolyl |
| .339 | CH₃ | N-pyrazolyl |
| .340 | F | N-pyrazolyl |
| .341 | H | N-1,2,4-triazol-1-yl |
| .342 | H | N-1,2,3-triazol-1-yl |
| .343 | H | N-pyrrolidinyl |
| .344 | H | N-piperidinyl |
| .345 | H | N-(4-methyl-piperazinyl) |
| .346 | H | N-morpholinyl |
| .347 | F | N-morpholinyl |
| .348 | CH₃ | N-imidazolyl |
| .349 | F | N(CH₃)₂ |
| .350 | F | OCH₂CH₂OCH₂CH₂OCH₃ |
| .351 | F | OCH₂COOCH₂CH₃ |
| .352 | F | OCH(CH₃)COOCH₂CH₃ |
| .353 | F | OCH₂CH(OH)CH₂OH |
| .354 | F | OCH₂COOC(CH₃)3 |
| .355 | F | OCH₂CH₂C₆H₅ |
| .356 | F | N(CH₂C≡CH)(SO₂CH₂CH₃) |
| .357 | F | OCH₂CH₂CH₂CH₃ |
| .358 | F | OCH(C₆H₅)COOCH₂CH₃ |
| .359 | F | OCH₂CH₂CH₂COOCH₂CH₃ |
| .360 | F | OCH₂CH₂CH₃ |
| .361 | F | OCH₂CH=CHCl |
| .362 | F | OCH₂COOCH₂C₆H₅ |
| .363 | F | OCH₂CN |
| .364 | H | OCH₂CN |
| .365 | F | OCH₂CF₃ |
| .366 | F | OCH₂CONH₂ |
| .367 | F | OC₃H₇-n |
| .368 | H | OCH₂CF₃ |
| .369 | H | OCH₂CONH₂ |
| .370 | Cl | OCH₂CONH₂ |
| .371 | Cl | OCH₂CN |
| .372 | F | OCH(CH₃)CN |
| .373 | F | OCH(CH₃)CF₃ |
| .374 | H | OSO₂CH₃ |
| .375 | H | OSO₂CH₃ |
| .376 | F | OSO₂CF₃ |
| .377 | F | OSO₂C₄F₉ |
| .378 | H | OSO₂C₄F₉ |
| .379 | H | SO₂C₂H₅ |
| .380 | F | SO₂CH₃ |
| .381 | Cl | SO₂CH₃ |
| .382 | Cl | SO₂CF₃ |
| .383 | F | SO₂CH₃ |
| .384 | F | SO₂C₆H₅ |
| .385 | F | SO₂C₆H₄-4Cl |
| .386 | H | SO₂C₆H₅ |
| .387 | Cl | SO₂C₆H₅ |
| .388 | F | OCH₂CONH(CH₃) |
| .389 | F | OCH₂CON(CH₃)₂ |
| .390 | H | OCH₂CON(CH₃)₂ |
| .391 | H | Cl |
| .392 | H | Br |
| .393 | H | I |
| .394 | F | F |
| .395 | H | F |
| .396 | F | Cl |
| .397 | F | Br |
| .398 | F | I |
| .399 | Cl | Cl |
| .400 | Cl | F |
| .401 | Cl | Br |
| .402 | F | OC(CH₃)₂COOCH₂CHCH₂ |
| .403 | F | OC(CH₃)₂COOCH₂CCH |
| .404 | F | OCH(CH₃)COOCH₂CHCH₂ |
| .405 | Cl | OC(CH₃)₂COOCH₂CHCH₂ |
| .406 | H | OC(CH₃)₂COOCH₂CHCH₂ |
| .407 | H | OCH(CF₃)CH₂COOC₂H₅ |
| .408 | F | OCH(CF₃)CH₂COOC₂H₅ |
| .409 | F | OCH(CH₃)CH₂COOCH₃ |
| .410 | F | OCH(CH₃)CH₂COOCH₃ |
| .411 | H | OCH(CH₃)CH₂COOCH₃ |
| .412 | H | OCH(CH₃)CH₂COOC₂H₅ |

Table 500: A preferred group of compounds of the formula I has the formula

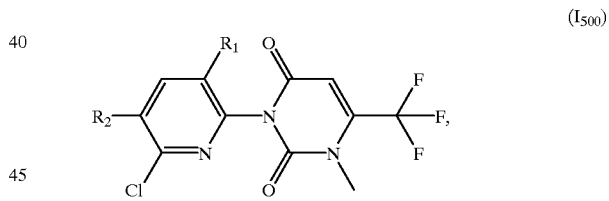

(I₅₀₀)

where the meanings of the respective substituents $R_1$ and $R_2$ are given in Table B, thus disclosing 168 specific compounds of the formula $I_{500}$.

Table 501: A further preferred group of compounds of the formula I has the formula

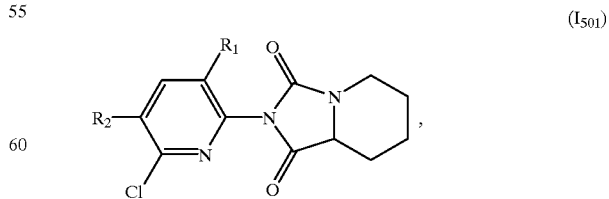

(I₅₀₁)

where the meanings of the respective substituents $R_1$ and $R_2$ are given in Table B, thus disclosing 168 specific compounds of the formula $I_{501}$.

Table 502: A further preferred group of compounds of the formula I has the formula

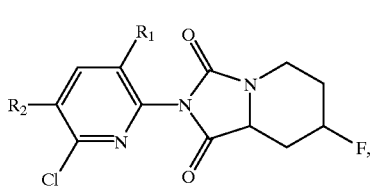

(I₅₀₂)

where the meanings of the respective substituents R₁ and R₂ are given in Table B, thus disclosing 168 specific compounds of the formula I₅₀₂.

Table 503: A further preferred group of compounds of the formula I has the formula

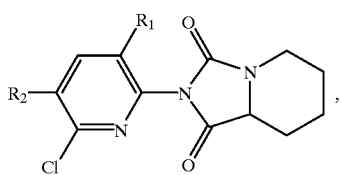

(I₅₀₃)

where the meanings of the respective substituents R₁ and R₂ are given in Table B, thus disclosing 168 specific compounds of the formula I₅₀₃.

Table 504: A further preferred group of compounds of the formula I has the formula

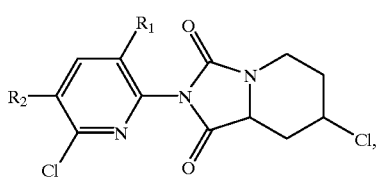

(I₅₀₄)

where the meanings of the respective substituents R₁ and R₂ are given in Table B, thus disclosing 168 specific compounds of the formula I₅₀₄.

Table 505: A further preferred group of compounds of the formula I has the formula

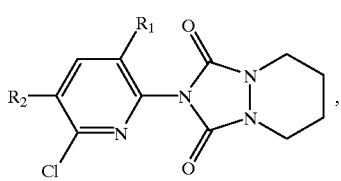

(I₅₀₅)

where the meanings of the respective substituents R₁ and R₂ are given in Table B, thus disclosing 168 specific compounds of the formula I₅₀₅.

Table 506: A further preferred group of compounds of the formula I has the formula

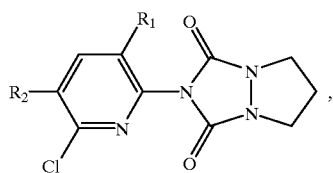

(I₅₀₆)

where the meanings of the respective substituents R₁ and R₂ are given in Table B, thus disclosing 168 specific compounds of the formula I₅₀₆.

Table 507: A further preferred group of compounds of the formula I has the formula

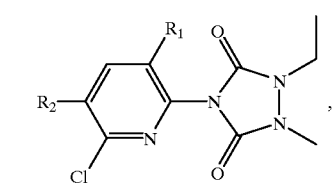

(I₅₀₇)

where the meanings of the respective substituents R₁ and R₂ are given in Table B, thus disclosing 168 specific compounds of the formula I₅₀₇.

Table 508: A further preferred group of compounds of the formula I has the formula

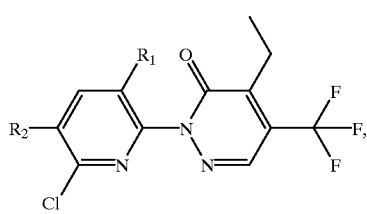

(I₅₀₈)

where the meanings of the respective substituents R₁ and R₂ are given in Table B, thus disclosing 168 specific compounds of the formula I₅₀₈.

Table 509: A further preferred group of compounds of the formula I has the formula

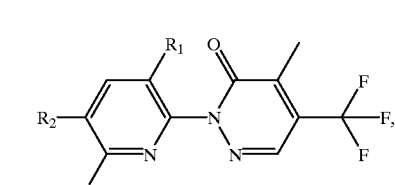

(I₅₀₉)

where the meanings of the respective substituents R₁ and R₂ are given in Table B, thus disclosing 168 specific compounds of the formula I₅₀₉.

Table 510: A further preferred group of compounds of the formula I has the formula

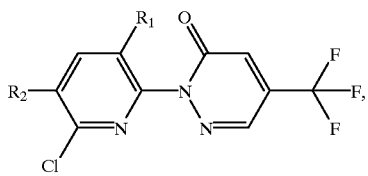
($I_{510}$)

where the meanings of the respective substituents $R_1$ and $R_2$ are given in Table B, thus disclosing 168 specific compounds of the formula $I_{510}$.

Table 511: A further preferred group of compounds of the formula I has the formula

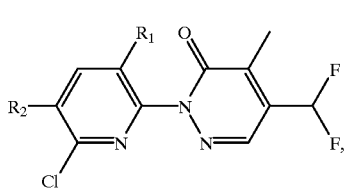
($I_{511}$)

where the meanings of the respective substituents $R_1$ and $R_2$ are given in Table B, thus disclosing 168 specific compounds of the formula $I_{511}$.

Table 512: A further preferred group of compounds of the formula I has the formula

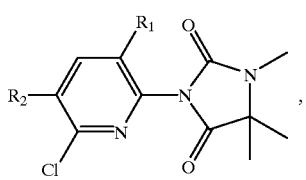
($I_{512}$)

where the meanings of the respective substituents $R_1$ and $R_2$ are given in Table B, thus disclosing 168 specific compounds of the formula $I_{512}$.

TABLE B

| Comp. No. | $R_1$ | $R_2$ |
|---|---|---|
| .001 | F | $NH_2$ |
| .002 | F | OH |
| .003 | F | $OCH_3$ |
| .004 | F | $OCH_2CH_3$ |
| .005 | F | $OCH(CH_3)_2$ |
| .006 | F | $OCH(CH_3)CH_2CH_2CH_3$ |
| .007 | F | $OCH_2CH=CH_2$ |
| .008 | F | $OCH(CH_3)CH=CH_2$ |
| .010 | F | $OCH_2C\equiv CH$ |
| .011 | F | $OCH(CH_3)C\equiv CH$ |
| .012 | F | $OCH_2OCH_2C_6H_5$ |
| .013 | F | $OCH_2(C_6H_5)$ |
| .014 | F | $OCH_2(2\text{-}F\text{---}C_6H_4)$ |
| .015 | F | $OCH(CH_3)(4\text{-}CH_3\text{---}C_6H_4)$ |
| .016 | F | $OC_6H_5$ |
| .017 | F | $OCH_2CH=CHCl$ |
| .018 | F | $OCH_2CH_2OH$ |
| .019 | F | $OCH_2OCH_3$ |
| .020 | F | $OCH_2CH_2OCH_2CH_3$ |

TABLE B-continued

| Comp. No. | $R_1$ | $R_2$ |
|---|---|---|
| .021 | F | $OCH_2CH_2OCH_2CH_2OCH_2CH_3$ |
| .022 | F | $OCH(CH_3)CH_2OCH_2CH=CH_2$ |
| .023 | F | $OCOCH_3$ |
| .024 | F | $OCOOCH_3$ |
| .025 | F | $OCOCH_2C_6H_5$ |
| .026 | F | $OCH_2SCH_3$ |
| .027 | F | $OCH_2CH_2SCH_2CH_3$ |
| .028 | F | $OCH_2COOCH_2CH_3$ |
| .029 | F | $OCH(CH_3)COOCH_3$ |
| .030 | F | $OCH(CH_3)_2COOCH_2CH=CH_2$ |
| .031 | F | O-tert-butyl |
| .032 | F | $OCH(CH_3)CH_2COOCH_2CH_3$ |
| .033 | F | $OCH_2COSCH_3$ |
| .034 | F | $OCH_2CONH_2$ |
| .035 | F | $OCH_2CON(CH_2CH_3)_2$ |
| .036 | F | $OCH(CH_3)CON(CH_3)_2$ |
| .037 | F | $OCH(CH_3)CONH(CH_2CH=CH_2)$ |
| .038 | F | $OCH(CH_3)CON(CH_3)(CH_2C\equiv CH)$ |
| .039 | F | $OCH(C_6H_5)CONH_2$ |
| .040 | F | $OCH(C_6H_5)CONH(CH_2C\equiv CH)$ |
| .041 | F | $OCH(C_6H_5)CON(CH_2CH=CH_2)_2$ |
| .042 | F | $OCH_2CH_2COOCH_2CH_3$ |
| .100 | Cl | $NH_2$ |
| .101 | Cl | OH |
| .102 | Cl | $NH(CH_3)$ |
| .103 | Cl | $OCH_3$ |
| .104 | Cl | $OCH_2CH_3$ |
| .105 | Cl | $OCH(CH_3)_2$ |
| .106 | Cl | $OCH(CH_3)CH_2CH_2CH_3$ |
| .107 | Cl | $OCH_2CH=CH_2$ |
| .108 | Cl | $OCH(CH_3)CH=CH_2$ |
| .109 | Cl | $OCH_2C\equiv CH$ |
| .110 | Cl | $OCH(CH_3)C\equiv CH$ |
| .111 | Cl | $OCH(\text{cyclopentyl})$ |
| .112 | Cl | $OCH_2(C_6H_5)$ |
| .113 | Cl | $OCH_2(2\text{-}F\text{---}C_6H_4)$ |
| .114 | Cl | $OCH(CH_3)(4\text{-}CH_3\text{---}C_6H_4)$ |
| .115 | Cl | $OC_6H_5$ |
| .116 | Cl | $OCH_2CH_2Cl$ |
| .117 | Cl | $OCH_2CH=CHCl$ |
| .118 | Cl | $OCH_2CH(Cl)CH_2$ |
| .119 | Cl | $OCH_2OCH_3$ |
| .120 | Cl | $OCH_2CH_2OCH_2CH_3$ |
| .121 | Cl | $OCH_2CH_2OCH_2CH_2OCH_2CH_3$ |
| .122 | Cl | $OCH(CH_3)CH_2OCH_2CH=CH_2$ |
| .123 | Cl | $OCOCH_3$ |
| .124 | Cl | $OCH_2SCH_3$ |
| .125 | Cl | $OCH_2CH_2SCH_2CH_3$ |
| .126 | Cl | $OCH_2COOH$ |
| .127 | Cl | $OCH(CH_3)COOH$ |
| .128 | Cl | (R)-$OCH(CH_3)COOH$ |
| .129 | Cl | (S)-$OCH(CH_3)COOH$ |
| .130 | Cl | $OCH_2COOCH_2CH_3$ |
| .131 | Cl | $OCH(CH_3)COOCH_3$ |
| .132 | Cl | $OCH(CH_3)COOCH_2CH=CH_2$ |
| .133 | Cl | $OCH(CH_3)COOCH_2(C_6H_5)$ |
| .134 | Cl | $OCH(CH_3)CH_2COOH$ |
| .135 | Cl | $OCH(CH_3)CH_2COOCH_2CH_3$ |
| .136 | Cl | $OCH_2CONH_2$ |
| .137 | Cl | $OCH_2CON(CH_2CH_3)_2$ |
| .138 | Cl | $OCH(CH_3)CON(CH_3)_2$ |
| .139 | Cl | $OCH(CH_3)CONH(CH_2CH=CH_2)$ |
| .140 | Cl | $OCH(CH_3)CON(CH_3)(CH_2C\equiv CH)$ |
| .141 | F | $OCH(CH_3)$-cyclopropyl |
| .142 | F | $OCH(CH_3)CH_2COOCH_3$ |
| .143 | H | $OCH(CH_3)CH_2COOCH_3$ |
| .144 | Cl | $OCH(C_6H_5)COOCH_3$ |
| .145 | Cl | $OCH(C_6H_5)COOCH(CH_3)C\equiv CH$ |
| .146 | Cl | $OCH(C_6H_5)COOCH_2C_6H_5$ |
| .147 | Cl | $OCH(C_6H_5)COSCH(CH_3)_2$ |
| .148 | Cl | $OCH(C_6H_5)CONH_2$ |
| .149 | Cl | $OCH(C_6H_5)CONH(CH_2C\equiv CH)$ |
| .150 | Cl | $OCH(C_6H_5)CONH(\text{cyclopropyl})$ |
| .151 | Cl | $OCH_2C(Cl)CH_2$ |
| .152 | Cl | $OCH_2CHCH\text{---}Cl$ |

TABLE B-continued

| Comp. No. | R₁ | R₂ |
|---|---|---|
| .153 | H | NH₂ |
| .154 | H | OH |
| .155 | H | OCH₃ |
| .156 | H | OCH₂CH₃ |
| .157 | H | OCH₂CH=CH₂ |
| .158 | H | OCH₂C≡CH |
| .159 | H | OCH₂C₆H₅ |
| .160 | H | OCH₂CH₂Cl |
| .161 | H | OCH₂CH₂OH |
| .162 | H | OCH₂OCH₃ |
| .163 | H | OCH₂CH₂OCH₂CH₃ |
| .164 | H | OCH₂CH₂OCH₂CH₂OCH₃ |
| .165 | H | OCOCH₃ |
| .166 | H | OCOOCH₃ |
| .167 | H | OCH₂SCH₃ |
| .168 | H | OCH₂CH₂SCH₃ |
| .169 | H | OCH₂COOCH₃ |
| .170 | H | OCH₂COOCH₂C₆H₅ |
| .171 | H | OCH₂CONH(CH₃) |
| .172 | H | OCH(CH₃)COOCH₂CH₃ |
| .173 | H | OCH(CH₃)COOCH₂CH=CH₂ |
| .174 | H | OCH(CH₃)COOCH₂C₆H₅ |
| .175 | H | OCH(CH₃)CONH₂ |
| .176 | H | OCH(CH₃)CONH(CH₂CH=CH₂) |
| .177 | H | OCH(CH₃)CON(CH₃)₂ |
| .178 | H | OCH(C₆H₅)COOCH₃ |
| .179 | H | OCH(C₆H₅)COOCH₂CH=CH₂ |
| .180 | H | OCH(C₆H₅)CONH₂ |
| .181 | H | OCH(C₆H₅)CONH(CH₂CH₃) |
| .182 | H | OCH(C₆H₅)CON(CH₃)₂ |
| .183 | F | OCH(CF₃)CH₂COOC₂H₅ |
| .184 | CH₃ | OCH₃ |
| .185 | CH₃ | OCH₂CH₃ |
| .186 | CH₃ | OCH₂CH=CH₂ |
| .187 | CH₃ | OCH₂C≡CH |
| .188 | CH₃ | OCH₂C₆H₅ |
| .189 | CH₃ | OCH₂OCH₃ |
| .190 | CH₃ | OCH₂CH₂OCH₂CH₃ |
| .191 | CH₃ | OCH₂SCH₃ |
| .192 | CH₃ | OCH₂CF₃ |
| .193 | CH₃ | OCH(CH₃)CONH₂ |
| .194 | F | OCH₂CH₂OCH₂CH₂OCH₃ |
| .195 | F | OCH₂COOCH₂CH₃ |
| .196 | F | OCH(CH₃)COOCH₂CH₃ |
| .197 | F | NO₂ |
| .198 | F | OCH₂COOC(CH₃)3 |
| .199 | F | OCH₂CH₂C₆H₅ |
| .200 | F | OCH₂CH₂CH₂CH₃ |
| .201 | F | OCH₂-cyclopropyl |
| .202 | F | OCH₂CH₂CH₃ |
| .203 | F | OCH₂CH=CHCl |
| .204 | F | OCH₂COOCH₂C₆H₅ |
| .147 | F | OCH₂CN |
| .148 | H | OCH₂CN |
| .149 | F | OCH₂CF₃ |
| .150 | F | OC₃H₇-n |
| .151 | H | OCH₂CF₃ |
| .152 | H | OCH₂CONH₂ |
| .153 | Cl | OCH₂CN |
| .154 | F | OCH(CH₃)CN |
| .155 | F | OCH(CH₃)CF₃ |
| .156 | H | OSO₂CH₃ |
| .157 | H | OSO₂CH₃ |
| .158 | F | OSO₂CF₃ |
| .159 | F | OSO₂C₄F₉ |
| .160 | H | OSO₂C₄F₉ |
| .161 | F | OCH₂CONH(CH₃) |
| .162 | F | OCH₂CON(CH₃)₂ |
| .163 | H | OCH₂CON(CH₃)₂ |
| .164 | F | OCH(CH₃)CF₃ |
| .165 | F | I |
| .166 | Cl | NO₂ |
| .167 | F | OC(CH₃)₂COOCH₂CHCH₂ |
| .168 | F | OC(CH₃)₂COOCH₂CCH |

Table 600: A preferred group of compounds of the formula III

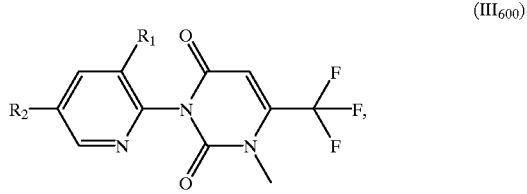

(III₆₀₀)

where the meanings of the respective substituents R₁ and R₂ are given in Table C, thus disclosing 25 specific compounds of the formula III₆₀₀.

Table 601: A further preferred group of compounds of the formula III has the formula

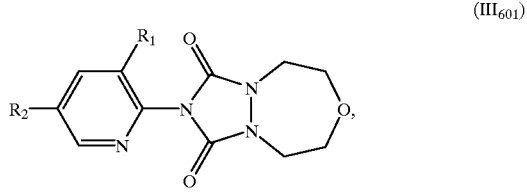

(III₆₀₁)

where the meanings of the respective substituents R₁ and R₂ are given in Table C, thus disclosing 25 specific compounds of the formula III₆₀₁.

Table 602: A further preferred group of compounds of the formula III has the formula

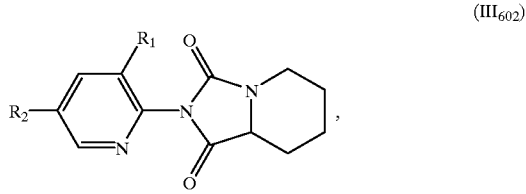

(III₆₀₂)

where the meanings of the respective substituents R₁ and R₂ are given in Table C, thus disclosing 25 specific compounds of the formula III₆₀₂.

Table 603: A further preferred group of compounds of the formula III has the formula

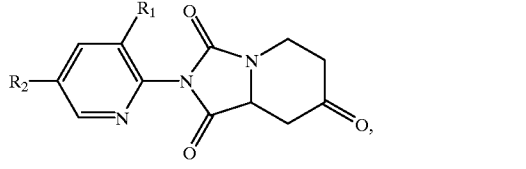

(III₆₀₃)

where the meanings of the respective substituents R₁ and R₂ are given in Table C, thus disclosing 25 specific compounds of the formula III₆₀₃.

Table 604: A further preferred group of compounds of the formula III has the formula

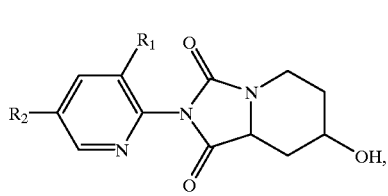

(III$_{604}$)

where the meanings of the respective substituents R$_1$ and R$_2$ are given in Table C, thus disclosing 25 specific compounds of the formula III$_{604}$.

Table 605: A further preferred group of compounds of the formula III has the formula

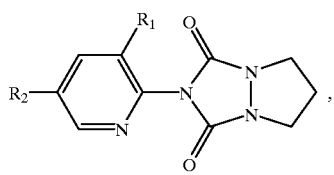

(III$_{605}$)

where the meanings of the respective substituents R$_1$ and R$_2$ are given in Table C, thus disclosing 25 specific compounds of the formula III605.

Table 606: A further preferred group of compounds of the formula III has the formula

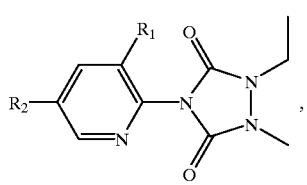

(III$_{606}$)

where the meanings of the respective substituents R$_1$ and R$_2$ are given in Table C, thus disclosing 25 specific compounds of the formula III$_{606}$.

Table 607: A further preferred group of compounds of the formula III has the formula

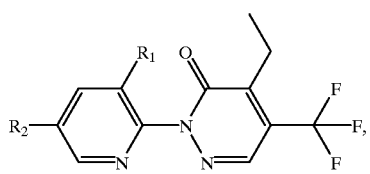

(III$_{607}$)

where the meanings of the respective substituents R$_1$ and R$_2$ are given in Table C, thus disclosing 25 specific compounds of the formula III$_{607}$.

Table 608: A further preferred group of compounds of the formula III has the formula

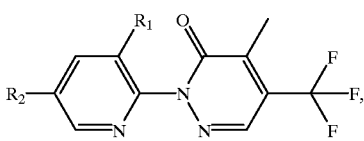

(III$_{608}$)

where the meanings of the respective substituents R$_1$ and R$_2$ are given in Table C, thus disclosing 25 specific compounds of the formula III$_{608}$.

Table 609: A further preferred group of compounds of the formula III has the formula

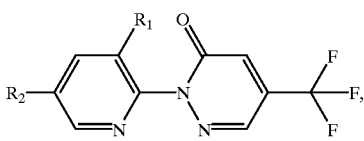

(III$_{609}$)

where the meanings of the respective substituents R$_1$ and R$_2$ are given in Table C, thus disclosing 25 specific compounds of the formula III$_{609}$.

Table 610: A further preferred group of compounds of the formula III has the formula

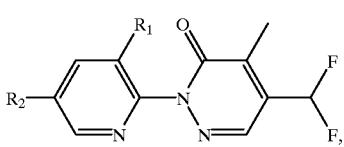

(III$_{610}$)

where the meanings of the respective substituents R$_1$ and R$_2$ are given in Table C, thus disclosing 25 specific compounds of the formula III$_{610}$.

Table 611: A further preferred group of compounds of the formula III has the formula

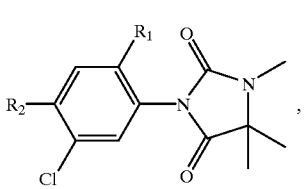

(III$_{611}$)

where the meanings of the respective substituents R$_1$ and R$_2$ are given in Table C, thus disclosing 25 specific compounds of the formula I$_{611}$.

Table 612: A further preferred group of compounds of the formula III has the formula

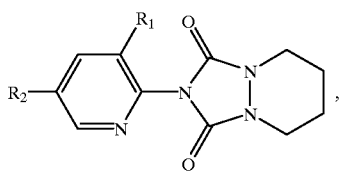

(III$_{612}$)

where the meanings of the respective substituents $R_1$ and $R_2$ are given in Table C, thus disclosing 25 specific compounds of the formula III$_{612}$.

Table 613: A further preferred group of compounds of the formula III has the formula

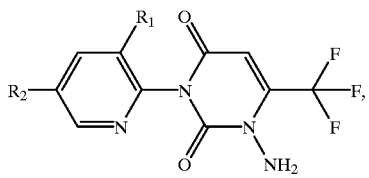

(III$_{613}$)

where the meanings of the respective substituents $R_1$ and $R_2$ are given in Table C, thus disclosing 25 specific compounds of the formula III$_{613}$.

Table 614: A further preferred group of compounds of the formula III has the formula

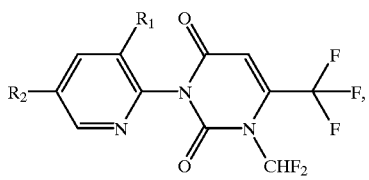

(III$_{614}$)

where the meanings of the respective substituents $R_1$ and $R_2$ are given in Table C, thus disclosing 25 specific compounds of the formula III$_{614}$.

Table 615: A further preferred group of compounds of the formula III has the formula

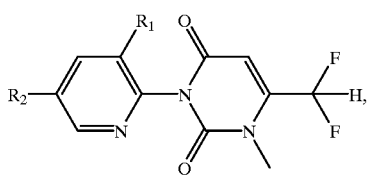

(III$_{615}$)

where the meanings of the respective substituents $R_1$ and $R_2$ are given in Table C, thus disclosing 25 specific compounds of the formula III$_{615}$.

Table 616: A further preferred group of compounds of the formula III has the formula

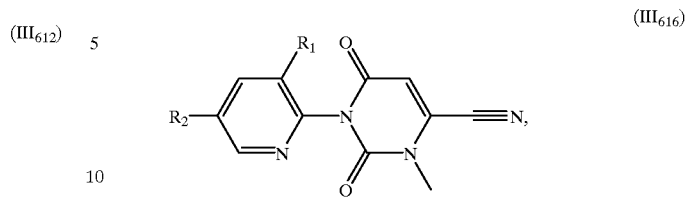

(III$_{616}$)

where the meanings of the respective substituents $R_1$ and $R_2$ are given in Table C, thus disclosing 25 specific compounds of the formula III$_{616}$.

Table 637: A further preferred group of compounds of the formula III has the formula

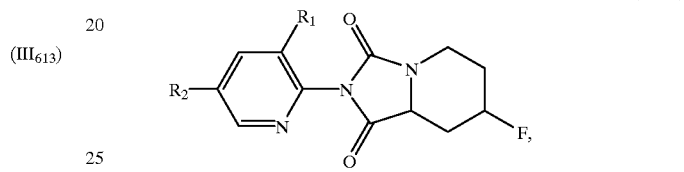

(III$_{637}$)

where the meanings of the respective substituents $R_1$ and $R_2$ are given in Table C, thus disclosing 25 specific compounds of the formula III$_{637}$.

Table 638: A further preferred group of compounds of the formula III has the formula

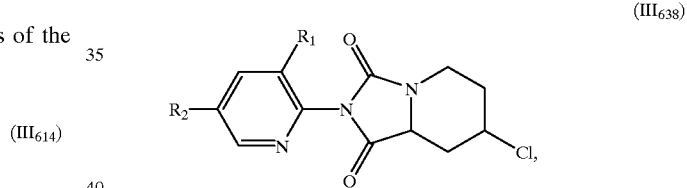

(III$_{638}$)

where the meanings of the respective substituents $R_1$ and B2 are given in Table C, thus disclosing 25 specific compounds of the formula III$_{638}$.

TABLE C

| Comp. No. | $R_1$ | $R_2$ |
|---|---|---|
| .001 | F | Cl |
| .002 | F | CN |
| .003 | F | OCH$_3$ |
| .004 | F | OCF$_3$ |
| .005 | F | CF$_3$ |
| .006 | F | Br |
| .007 | F | NO$_2$ |
| .008 | F | CH$_3$ |
| .009 | F | OCH$_2$C≡CH |
| .010 | Cl | CN |
| .011 | Cl | OCH$_3$ |
| .012 | Cl | OCF$_3$ |
| .013 | Cl | CF$_3$ |
| .014 | Cl | Br |
| .015 | Cl | NO$_2$ |
| .016 | Cl | CH$_3$ |
| .017 | Cl | Cl |
| .018 | Cl | CF$_2$H |
| .019 | H | F |
| .020 | H | Cl |
| .021 | H | Br |
| .022 | H | CF$_3$ |

TABLE C-continued

| Comp. No. | $R_1$ | $R_2$ |
|---|---|---|
| .023 | H | $OCF_3$ |
| .024 | H | $NO_2$ |
| .025 | H | CN |

Table 617: A preferred group of compounds of the formula IV has the formula

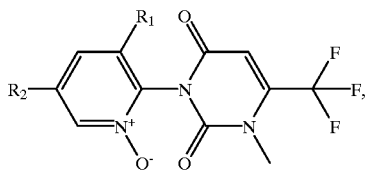

($IV_{617}$)

where the meanings of the respective substituents $R_1$ and $R_2$ are given in Table D, thus disclosing 25 specific compounds of the formula $IV_{617}$.

Table 618: A further preferred group of compounds of the formula IV has the formula

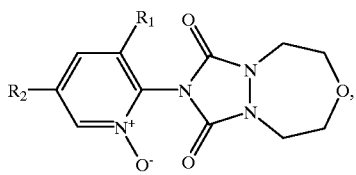

($IV_{618}$)

where the meanings of the respective substituents $R_1$ and $R_2$ are given in Table D, thus disclosing 25 specific compounds of the formula $IV_{618}$.

Table 619: A further preferred group of compounds of the formula IV has the formula

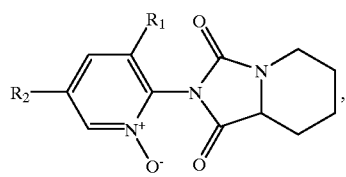

($IV_{619}$)

where the meanings of the respective substituents $R_1$ and $R_2$ are given in Table D, thus disclosing 25 specific compounds of the formula $IV_{619}$.

Table 620: A further preferred group of compounds of the formula IV has the formula

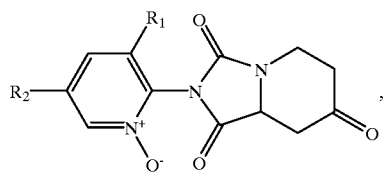

($IV_{620}$)

where the meanings of the respective substituents $R_1$ and $R_2$ are given in Table D, thus disclosing 25 specific compounds of the formula $IV_{620}$.

Table 621: A further preferred group of compounds of the formula IV has the formula

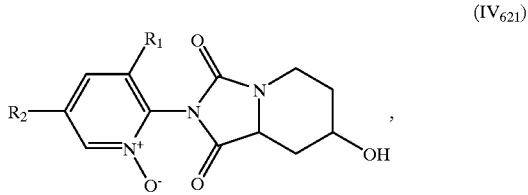

($IV_{621}$)

where the meanings of the respective substituents $R_1$ and $R_2$ are given in Table D, thus disclosing 25 specific compounds of the formula $IV_{621}$.

Table 622: A further preferred group of compounds of the formula IV has the formula

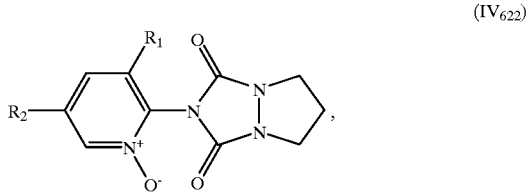

($IV_{622}$)

where the meanings of the respective substituents $R_1$ and $R_2$ are given in Table D, thus disclosing 25 specific compounds of the formula $IV_{622}$.

Table 623: A further preferred group of compounds of the formula IV has the formula

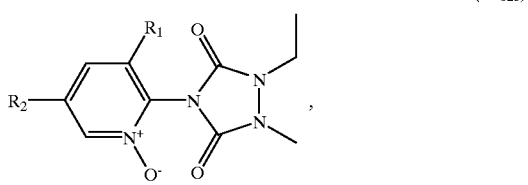

($IV_{623}$)

where the meanings of the respective substituents $R_1$ and $R_2$ are given in Table D, thus disclosing 25 specific compounds of the formula $IV_{623}$.

Table 624: A further preferred group of compounds of the formula IV has the formula

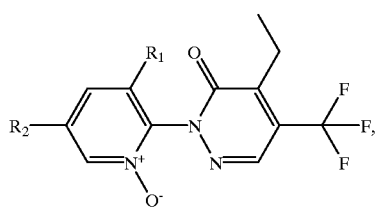

($IV_{624}$)

where the meanings of the respective substituents $R_1$ and $R_2$ are given in Table D, thus disclosing 25 specific compounds of the formula $IV_{624}$.

Table 625: A further preferred group of compounds of the formula IV has the formula

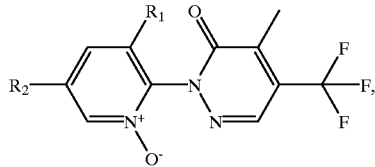

(IV$_{625}$)

where the meanings of the respective substituents R$_1$ and R$_2$ are given in Table D, thus disclosing 25 specific compounds of the formula IV$_{625}$.

Table 626: A further preferred group of compounds of the formula IV has the formula

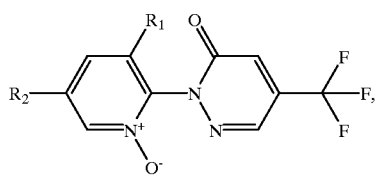

(IV$_{626}$)

where the meanings of the respective substituents R$_1$ and R$_2$ are given in Table D, thus disclosing 25 specific compounds of the formula IV$_{626}$.

Table 627: A further preferred group of compounds of the formula IV has the formula

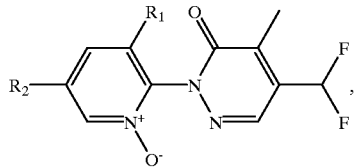

(IV$_{627}$)

where the meanings of the respective substituents R$_1$ and R$_2$ are given in Table D, thus disclosing 25 specific compounds of the formula IV$_{627}$.

Table 628: A further preferred group of compounds of the formula IV has the formula

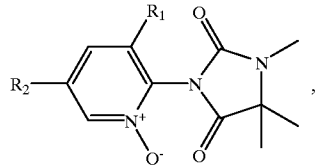

(IV$_{628}$)

where the meanings of the respective substituents R$_1$ and R$_2$ are given in Table D, thus disclosing 25 specific compounds of the formula IV$_{628}$.

Table 629 A further preferred group of compounds of the formula IV has the formula

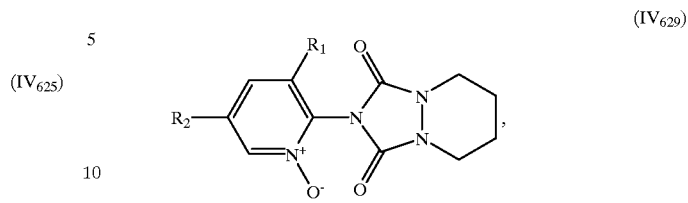

(IV$_{629}$)

where the meanings of the respective substituents R$_1$ and R$_2$ are given in Table D, thus disclosing 25 specific compounds of the formula IV$_{629}$.

Table 630: A further preferred group of compounds of the formula IV has the formula

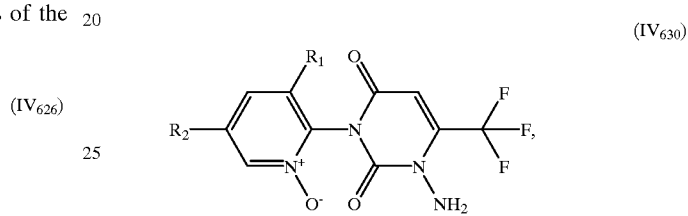

(IV$_{630}$)

where the meanings of the respective substituents R$_1$ and R$_2$ are given in Table D, thus disclosing 25 specific compounds of the formula IV$_{630}$.

Table 631: A further preferred group of compounds of the formula IV has the formula

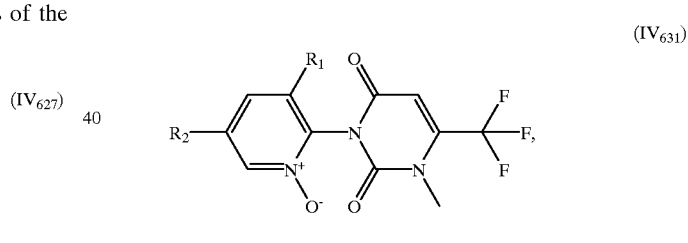

(IV$_{631}$)

where the meanings of the respective substituents R$_1$ and R$_2$ are given in Table D, thus disclosing 25 specific compounds of the formula IV$_{631}$.

Table 632: A further preferred group of compounds of the formula IV has the formula

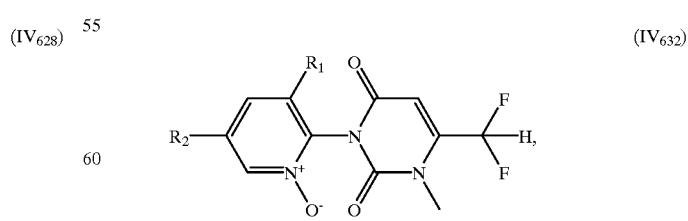

(IV$_{632}$)

where the meanings of the respective substituents R$_1$ and R$_2$ are given in Table D, thus disclosing 25 specific compounds of the formula IV$_{632}$.

Table 633: A further preferred group of compounds of the formula IV has the formula

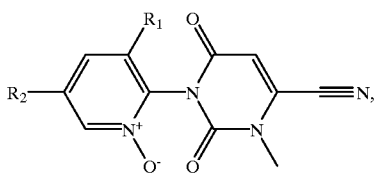
(IV$_{633}$)

where the meanings of the respective substituents $R_1$ and $R_2$ are given in Table D, thus disclosing 25 specific compounds of the formula IV$_{633}$.

Table 634: A further preferred group of compounds of the formula IV has the formula

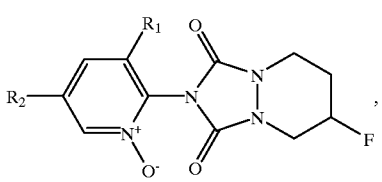
(IV$_{634}$)

where the meanings of the respective substituents $R_1$ and $R_2$ are given in Table D, thus disclosing 25 specific compounds of the formula IV$_{634}$.

Table 635: A further preferred group of compounds of the formula IV has the formula

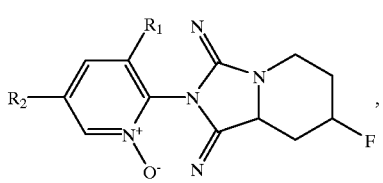
(IV$_{635}$)

where the meanings of the respective substituents $R_1$ and $R_2$ are given in Table D, thus disclosing 25 specific compounds of the formula IV$_{635}$.

Table 636: A further preferred group of compounds of the formula IV has the formula

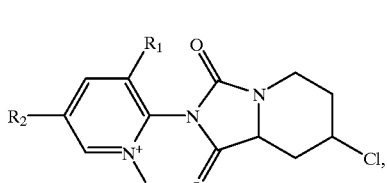
(IV$_{636}$)

where the meanings of the respective substituents $R_1$ and $R_2$ are given in Table D, thus disclosing 25 specific compounds of the formula IV$_{636}$.

TABLE D

| Comp. No. | $R_1$ | $R_2$ |
|---|---|---|
| .001 | F | Cl |
| .002 | F | CN |

TABLE D-continued

| Comp. No. | $R_1$ | $R_2$ |
|---|---|---|
| .003 | F | OCH$_3$ |
| .004 | F | OCF$_3$ |
| .005 | F | CF$_3$ |
| .006 | F | Br |
| .007 | F | NO$_2$ |
| .008 | F | CH$_3$ |
| .009 | F | OCH$_2$C≡CH |
| .010 | Cl | CN |
| .011 | Cl | OCH$_3$ |
| .012 | Cl | OCF$_3$ |
| .013 | Cl | CF$_3$ |
| .014 | Cl | Br |
| .015 | Cl | NO$_2$ |
| .016 | Cl | CH$_3$ |
| .017 | Cl | Cl |
| .018 | Cl | CF$_2$H |
| .019 | H | F |
| .020 | H | Cl |
| .021 | H | Br |
| .022 | H | CF$_3$ |
| .023 | H | OCF$_3$ |
| .024 | H | NO$_2$ |
| .025 | H | CN |

Table E: Physicochemical data for compounds in the above-mentioned tables which have been prepared. The figure before the dot indicates the number of the table, for example 1.367 means compound No. 367 of Table A in Table 1, and 500.003 means Compound No. 003 of Table B in Table 500.

| Comp. No. | Physicochemical data |
|---|---|
| 1.001 | $^1$H NMR (CDCl$_3$; δ ppm): 7.62 (d, 1H); 6.38 (s, 1H); 5.83 (s, 2H); 3.47 (s, 3H). |
| 1.002 | m.p. 200–202° C. (Example H5) |
| 1.016 | m.p. 120–122° C. |
| 1.017 | oil; n$_D^{40}$ 1.5139 |
| 1.020 | oil; n$_D^{39}$ 1.5240 |
| 1.022 | m.p. 119–121° C. |
| 1.025 | oil; n$_D^{30}$ 1.5345 |
| 1.026 | m.p. 146–147° C. |
| 1.047 | m.p. 123–125° C. |
| 1.048 | m.p. 128–130° C. |
| 1.123 | m.p. 168–170° C. |
| 1.363 | m.p. 57–59° C. |
| 1.365 | n$_D^{35}$ 1.4881 |
| 1.366 | m.p. 115–117° C. |
| 1.367 | oil; n$_D^{40}$ 1.5037 |
| 1.396 | m.p. 113–115° C. |
| 1.399 | m.p. 183–184° C. |
| 1.402 | m.p. 115–117° C. |
| 3.394 | m.p. 145–147° C. |
| 3.396 | m.p. 146–148° C. |
| 31.002 | m.p. 161–163° C. |
| 31.017 | m.p. 80–82° C. |
| 31.022 | m.p. 88–90° C. |
| 31.365 | $^1$H-NMR (CDCl$_3$): 8.10 ppm (s, 1H); 7.76 ppm (d, 1H); 7.34 ppm (s, 1H); 4.76 ppm (m, 2H) |
| 31.396 | $^1$H-NMR (CDCl$_3$): 8.12 ppm (s, 1H); 7.83 ppm (d, 1H); 7.35 ppm (s, 1H) |
| 81.396 | m.p. 192–193° C. |
| 82.002 | $^1$H-NMR (CDCl$_3$): 7.73 ppm (d, 1H); 5.19 ppm (broad d, 1H); 4.42 ppm (m, 1H); 4.17 ppm (m, 1H); 3.33 ppm (m, 1H); 2.62 ppm (m, 1H); 1.68–2.23 ppm (2xm, 3H) (isomer B) |
| 82.365 | $^1$H-NMR (CDCl$_3$): 7.72 ppm (d, 1H); 5.20 ppm (broad d, 1H); 4.73 ppm (m, 2H); 4.40 ppm (m, 1H); 4.15 ppm (m, 1H); 3.33 ppm (m, 1H); 2.65 ppm (m, 1H); 2.15 ppm (m, 1H); 1.64–1.94 ppm (m, 2H) (isomer B) |
| 155.396 | m.p. 223–225° C. |
| 500.002 | m.p. 189–192° C. |

-continued

| Comp. No. | Physicochemical data |
|---|---|
| 500.003 | m.p. 143–145° C. |
| 500.004 | m.p. 149–151° C. |
| 500.007 | $n_D^{39}$ 1.5186 |
| 500.009 | m.p. 69–71° C. |
| 500.027 | m.p. 139–141° C. |
| 500.028 | m.p. 80–81° C. |
| 500.029 | $n_D^{35}$ 1.5093 |
| 500.033 | m.p. 193–195° C. |
| 500.144 | m.p. 106–108° C. |
| 500.147 | m.p. 134–136° C. |
| 500.149 | m.p. 141–143° C. |
| 510.002 | $^1$H-NMR (CDCl$_3$): 8.14 ppm (s, 1H); 7.38 ppm (d, 1H); 7.22 ppm (s, 1H) |
| 510.004 | m.p. 92–94° C. |
| 510.010 | $^1$H-NMR (CDCl$_3$): 8.10 ppm (s, 1H); 7.84 ppm (d, 1H); 7.33 ppm (s, 1H); 4.90 ppm (s, 2H); 2.71 ppm (s, 1H) |
| 600.001 | m.p. 133–134° C. |
| 600.021 | m.p. 161–163° C. |
| 609.001 | m.p. 114–116° C. |
| 613.001 | m.p. 183–184° C. |
| 617.001 | m.p. 142–143° C. |
| 626.001 | m.p. 143–145° C. |
| 634.001 | m.p. 180–183° C. (isomer B) |
| 635.001 | m.p. 183–185° C.; $^1$H-NMR (CDCl$_3$): 8.30 ppm (s, 1H); 7.25 ppm (d, 1H); 5.19 ppm (d, 1H); 4.41 ppm (m, 1H); 4.17 ppm (m, 1H); 3.32 ppm (m, 1H); 2.61 ppm (m, 1H); 2.14 ppm (m, 1H); 1.61–2.20 ppm (m, 2H) (isomer B) |
| 637.001 | m.p. 189–191° C. |
| 638.001 | m.p. 150–152° C. |

Examples of specific formulations of active ingredients of the formula I, such as emulsion concentrates, solutions, wettable powders, coated granules, extruder granules, dusts and suspension concentrates, are described in WO 97/34485 on pages 9 to 13.

BIOLOGICAL EXAMPLES

Example B1

Herbicidal Action Before Plant Emergence (Pre-emergence Action)

Monocotyledonous and dicotyledonous test plants are sown in standard soil in plastic pots. Immediately after sowing, the test substances are sprayed on as aqueous suspensions (prepared from a 25% strength wettable powder (Example F3, b) in accordance with WO 97/34485) or as emulsions (prepared from a 25% strength emulsion concentrate (Example F1, c) in accordance with WO 97/34485), corresponding to a dosage of 2 kg of a.i./ha (500 l of water/ha). The test plants are subsequently grown in the greenhouse under optimal conditions. After a test period of 3 weeks, the experiment is evaluated using a nine-level key (1=complete damage, 9=no effect). Score figures of 1 to 4 (in particular 1 to 3) signify a good to very good herbicidal action.

Test plants: Lolium, Setaria, Sinapis, Solanum, Stellaria, Ipomea.

The compounds according to the invention exhibit good herbicidal activity.

Examples of the good herbicidal activity of the compounds of the formula I are given in Table B1.

TABLE B1

Pre-emergence action:

| Active ingredient No. | Test plant: | | | | | | Dose [g a.i./ha] |
|---|---|---|---|---|---|---|---|
| | Lolium | Setaria | Sinapis | Solanum | Stellaria | Ipomoea | |
| 1.002 | 7 | 1 | 1 | 1 | 5 | 1 | 2000 |
| 1.016 | 1 | 1 | 1 | 1 | 1 | 1 | 2000 |
| 1.017 | 1 | 1 | 1 | 1 | 1 | 1 | 2000 |
| 1.020 | 1 | 1 | 1 | 1 | 1 | 1 | 2000 |
| 1.022 | 1 | 1 | 1 | 1 | 1 | 1 | 2000 |
| 1.025 | 3 | 1 | 1 | 1 | 3 | 1 | 2000 |
| 1.026 | 1 | 1 | 1 | 1 | 3 | 1 | 2000 |
| 1.047 | 5 | 1 | 1 | 1 | 7 | 1 | 2000 |
| 1.048 | 1 | 1 | 1 | 1 | 1 | 1 | 2000 |
| 1.363 | 3 | 1 | 2 | 1 | 1 | 7 | 2000 |
| 1.365 | 1 | 1 | 1 | 1 | 1 | 1 | 2000 |
| 1.366 | 3 | 1 | 1 | 1 | 3 | 1 | 2000 |
| 1.367 | 1 | 1 | 1 | 1 | 1 | 1 | 2000 |
| 1.396 | 1 | 1 | 1 | 1 | 1 | 1 | 2000 |
| 1.402 | 1 | 1 | 1 | 1 | 1 | 4 | 2000 |
| 500.007 | | 4 | | 1 | | | 2000 |
| 500.009 | 2 | 1 | 3 | 1 | 1 | 3 | 2000 |
| 500.029 | | 4 | | 1 | | | 2000 |
| 500.033 | | 2 | | 1 | | | 2000 |
| 500.144 | | 2 | | 1 | | | 2000 |
| 500.147 | | 1 | | 1 | | | 2000 |

The same results are obtained when the compounds of the formula I are formulated as described in Examples F2 and F4 to F8 in accordance with WO 97/34485.

Example B2

Post-emergence Herbicidal Action

Monocotyledonous and dicotyledonous test plants are grown in the greenhouse in plastic pots containing standard soil and, in the 4- to 6-leaf stage, sprayed with an aqueous suspension of the test substances of the formula I, prepared from a 25% strength wettable powder (Example F3, b) in accordance with WO 97/34485) or with an emulsion of the test substances of the formula I, prepared from a 25% strength emulsion concentrate (Example F1, c) in accordance with WO 97/34485), corresponding to a dosage of 2 kg/ a.i./ha (500 l of water/ha). The test plants are subsequently grown on in the greenhouse under optimal conditions. After a test period of approximately 18 days, the experiment is evaluated using a nine-level key (1=complete damage, 9=no effect). Score figures of 1 to 4 (in particular 1 to 3) signify a good to very good herbicidal action. In this experiment, the compounds of the formula I exhibit a potent herbicidal activity.

Test plants: Lolium, Setaria, Sinapis, Solanum, Stellaria, Ipomea.

In this experiment, again, the compounds of the formula I exhibit a potent herbicidal activity.

Examples of the good herbicidal activity of the compounds of the formula I are given in Table B2.

TABLE B2

| Active ingredient No. | Post-emergence action: Test plant: | | | | | | Dose [g a.i./ha] |
|---|---|---|---|---|---|---|---|
| | Lolium | Setaria | Sinapis | Solanum | Stellaria | Ipomoea | |
| 1.002 | 6 | 5 | 2 | 1 | 5 | 1 | 2000 |
| 1.016 | 1 | 1 | 1 | 1 | 1 | 1 | 2000 |
| 1.017 | 1 | 1 | 1 | 1 | 1 | 1 | 2000 |
| 1.020 | 1 | 1 | 1 | 1 | 1 | 1 | 2000 |
| 1.022 | 1 | 1 | 1 | 1 | 1 | 1 | 2000 |
| 1.025 | 1 | 3 | 1 | 1 | 1 | 1 | 2000 |
| 1.026 | 3 | 3 | 1 | 1 | 3 | 1 | 2000 |
| 1.047 | 3 | 1 | 1 | 1 | 4 | 1 | 2000 |
| 1.048 | 1 | 1 | 1 | 1 | 1 | 1 | 2000 |
| 1.363 | 1 | 1 | 1 | 1 | 1 | 1 | 2000 |
| 1.365 | 1 | 1 | 1 | 1 | 1 | 1 | 2000 |
| 1.366 | 1 | 1 | 1 | 1 | 1 | 1 | 2000 |
| 1.367 | 1 | 1 | 1 | 1 | 1 | 1 | 2000 |
| 1.396 | 3 | 3 | 1 | 1 | 3 | 1 | 2000 |
| 1.402 | 1 | 1 | 1 | 1 | 1 | 1 | 2000 |
| 500.004 | | | 2 | 1 | | 3 | 2000 |
| 500.009 | 1 | 1 | 1 | 1 | 1 | 1 | 2000 |
| 500.029 | | | 1 | 1 | | 1 | 2000 |
| 500.033 | | | 1 | 1 | | 1 | 2000 |
| 500.147 | | | 1 | 1 | | 1 | 2000 |
| 500.149 | | | 1 | 1 | | 1 | 2000 |

The same results are obtained when the compounds of the formula I are formulated as described in Examples F2 and F4 to F8 in accordance with WO 97/34485.

The active ingredients of the formula I of the invention may also be used for weed control as a mixture with known herbicides as co-herbicides, for example as ready-mixes or as a 'tank-mix'. Examples of co-herbicides which are suitable as components in mixtures with the active ingredients of the formula I are the following:

Compound of the formula I+acetochlor; compound of the formula I+acifluorfen; compound of the formula I+aclonifen; compound of the formula I+alachlor; compound of the formula I+ametryn; compound of the formula I+aminotriazole; compound of the formula I+amidosulfuron; compound of the formula I+asulam; compound of the formula I+atrazine; compound of the formula I+BAY FOE 5043; compound of the formula I+benazolin; compound of the formula I+bensulfuron; compound of the formula I+bentazone; compound of the formula I+bifenox; compound of the formula I+bispyribac-sodium; compound of the formula I+bialaphos; compound of the formula I+bromacil; compound of the formula I+bromoxynil; compound of the formula I+bromophenoxim; compound of the formula I+butachlor; compound of the formula I+butylate; compound of the formula I+cafenstrole; compound of the formula I+carbetamide; compound of the formula I+chloridazone; compound of the formula I+chlorimuron-ethyl; compound of the formula I+chlorbromuron; compound of the formula I+chlorsulfuron; compound of the formula I+chlortoluron; compound of the formula I+cinosulfuron; compound of the formula I+clethodim; compound of the formula I+clodinafop; compound of the formula I+clomazone; compound of the formula I+clopyralid; compound of the formula I+cloransulam; compound of the formula I+cyanazine; compound of the formula I+cyhalofop; compound of the formula I+dalapon; compound of the formula I+2,4-D; compound of the formula I+2,4-DB; compound of the formula I+desmetryn; compound of the formula I+desmedipham; compound of the formula I+dicamba; compound of the formula I+diclofop; compound of the formula I+difenzoquat metilsulfate; compound of the formula I+diflufenican; compound of the formula I+dimefuron; compound of the formula I+dimepiperate; compound of the formula I+dimethachlor; compound of the formula I+dimethametryn; compound of the formula I+dimethenamid; compound of the formula I+S-dimethenamid; compound of the formula I+dinitramine; compound of the formula I+dinoterb; compound of the formula I+dipropetryn; compound of the formula I+diuron; compound of the formula I+diquat; compound of the formula I+DSMA; compound of the formula I+EPTC; compound of the formula I+esprocarb; compound of the formula I+ethalfluralin; compound of the formula I+ethametsulfuron; compound of the formula I+ethephon; compound of the formula I+ethofumesate; compound of the formula I+ethoxysulfuron; compound of the formula I+fenclorim; compound of the formula I+flamprop; compound of the formula I+fluazasulfuron; compound of the formula I+fluazifop; compound of the formula I+flumetralin; compound of the formula I+flumetsulam; compound of the formula I+fluometuron; compound of the formula I+flurchloridone; compound of the formula I+fluoxaprop; compound of the formula I+fluroxypyr; compound of the formula I+fluthiacet-methyl; compound of the formula I+fluxofenim; compound of the formula I+fomesafen; compound of the formula I+glufosinate; compound of the formula I+glyphosate; compound of the formula I+halosulfuron; compound of the formula I+haloxyfop; compound of the formula I+hexazinone; compound of the formula I+imazamethabenz; compound of the formula I+imazapyr; compound of the formula I+imazaquin; compound of the formula I+imazethapyr; compound of the formula I+imazosulfuron; compound of the formula I+ioxynil; compound of the formula I+isoproturon; compound of the formula I+isoxaben; compound of the formula I+isoxaflutole; compound of the formula I+Karbutylate; compound of the formula I+lactofen; compound of the formula I+lenacil; compound of the formula I+linuron; compound of the formula I+MCPP; compound of the formula I+metamitron; compound of the formula I+metazachlor; compound of the formula I+methabenzthiazuron; compound of the formula I+methazole; compound of the formula I+metobromuron; compound of the formula I+metolachlor; compound of the formula I+S-metolachlor; compound of the formula I+metosulam; compound of the formula I+metribuzin; compound of the formula I+metsulfuron-methyl; compound of the formula I+molinate; compound of the formula I+MCPA; compound of the formula I+MSMA; compound of the formula I+napropamide; compound of the formula I+NDA-402989; compound of the formula I+nefenacet; compound of the formula I+nicosulfuron; compound of the formula I+norflurazon; compound of the formula I+oryzalin; compound of the formula I+oxadiazon; compound of the formula I+oxasulfuron; compound of the formula I+oxyfluorfen; compound of the formula I+paraquat; compound of the formula I+pendimethalin; compound of the formula I+phenmedipham; compound of the formula I+fenoxaprop-P-ethyl (R); compound of the formula I+picloram; compound of the formula I+pretilachlor; compound of the formula I+primisulfuron; compound of the formula I+prometon; compound of the formula I+prometryn; compound of the formula I+propachlor; compound of the formula I+propanil; compound of the formula I+propazine; compound of the formula I+propaquizafop; compound of the formula I+propyzamide; compound of the formula I+prosulfuron; compound of the formula I+pyrazolynate; compound of the formula I+pyrazosulfuron-ethyl; compound of the formula I+pyrazoxyphen; compound of the formula I+pyridate; compound of the formula I+pyriminobac-methyl; compound of the formula I+pyrithiobac-sodium; compound of the formula I+quinclorac; compound of the formula I+quizalofop; compound of the formula I+rimsulfuron; compound of the formula I+Sequestren; compound of the formula I+sethoxydim; compound of the formula I+simetryn; compound of the formula I+simazine; compound of the formula I+sulcotrione; compound of the formula I+sulfosate; compound of the formula I+sulfosulfuron-methyl; compound of the formula I+tebutam; compound of the formula I+tebuthiuron; compound of the formula I+terbacil; compound of the formula I+terbumeton; compound of the formula I+terbuthylazine; compound of the formula I+terbutryn; compound of the formula I+thiazafluron; compound of the formula I+thiazopyr; compound of the formula I+thifensulfuron-methyl; compound of the formula I+thiobencarb; compound of the formula I+tralkoxydim; compound of the formula I+tri-allate; compound of the formula I+triasulfuron; compound of the formula I+trifluralin; compound of the formula I+tribenuron-methyl; compound of the formula I+triclopyr; compound of the formula I+triflusulfuron; compound of the formula I+trinexapac-ethyl, and esters and salts of these components with which the compound of the formula I can be mixed, for example those mentioned in The Pesticide Manual, Eleventh Edition, 1997, BCPC.

What is claimed is:
1. A compound of the formula I

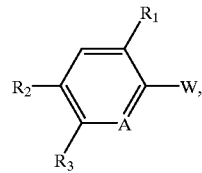

(I)

in which

A =N— or

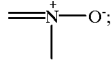

$R_1$ is hydrogen, fluorine, chlorine, bromine or methyl;
$R_2$ is $C_1$–$C_4$alkyl, $C_1$–$C_4$haloalkyl, halogen, $R_6O$—, nitro, amino or cyano;
$R_3$ is halogen, nitro, amino, $R_4NH$—, $R_4R_5N$—, azido or $ClS(O)_2$—;
$R_4$ and $R_5$ independently of one another are $C_1$–$C_8$alkyl, $C_3$–$C_8$alkenyl, $C_3$–$C_8$alkynyl, $C_3$–$C_6$cycloalkyl, $C_1$–$C_8$haloalkyl, $C_3$–$C_8$haloalkenyl, HCO—, $C_1$–$C_4$alkylcarbonyl, $C_1$–$C_4$haloalkylcarbonyl, $C_1$–$C_4$alkylsulfonyl, $C_1$–$C_4$haloalkylsulfonyl, benzyl or benzyl which is mono- to trisubstituted on the phenyl ring by halogen, $C_1$–$C_4$alkyl or $C_1$–$C_4$haloalkyl; or $R_4$ and $R_5$ together with the N atom to which they are bonded form a saturated or unsaturated heterocyclic ring which contains O, N or S as further hetero atoms and which can be substituted by halogen, $C_1$–$C_3$alkyl, $C_1$–$C_3$haloalkyl, $C_1$–$C_3$alkoxy, $C_1$–$C_4$alkoxycarbonyl, $C_1$–$C_3$alkylS(O)$_{n1}$—, nitro or cyano; or
$R_3$ is $R_6O$—;

$R_6$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl, cyano-$C_1$–$C_8$alkyl, $C_3$–$C_8$haloalkenyl, hydroxy-$C_1$–$C_4$alkyl, $C_1$–$C_4$alkoxy-$C_1$–$C_4$alkyl, $C_3$–$C_6$alkenyloxy-$C_1$–$C_4$alkyl, $C_3$–$C_6$alkynyloxy-$C_1$–$C_4$alkyl, $C_1$–$C_4$alkoxy-$C_1$–$C_4$alkoxy-$C_1$–$C_4$alkyl, $C_1$–$C_4$alkylthio-$C_1$–$C_4$alkyl, $C_1$–$C_8$alkylcarbonyl, $C_1$–$C_8$alkoxycarbonyl, $C_3$–$C_8$alkenyloxycarbonyl, benzyloxy-$C_1$— or —$C_2$alkyl, benzylcarbonyl, benzyloxycarbonyl, phenyl,phenyl-$C_2$–$C_8$alkyl, benzyl, pyridyl, pyrimidinyl, pyrazinyl or pyridazinyl, it being possible for these aromatic and heteroaromatic rings to be optionally mono- to trisubstituted by halogen, $C_1$–$C_4$alkyl or $C_1$–$C_4$haloalkyl; or $R_6$ is $R_7X_1C(O)$—$C_1$–$C_8$alkyl- or

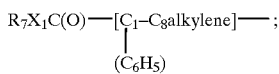

$X_1$ is oxygen, sulfur or

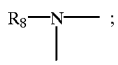

$R_7$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl, $C_3$–$C_8$haloalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is mono- to trisubstituted by halogen, $C_1$–$C_4$alkyl or $C_1$–$C_4$haloalkyl, or benzyl or benzyl which is mono- to trisubstituted on the phenyl ring by halogen, $C_1$–$C_4$alkyl or $C_1$–$C_4$haloalkyl;

$R_8$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl or benzyl; or $R_3$ is $R_9S(O)_{n1}$—;

$n_1$ is 0, 1 or 2;

$R_9$ is $C_1$–$C_8$alkyl, $C_3$–$C_8$alkenyl, $C_3$–$C_8$alkynyl, $C_3$–$C_6$cycloalkyl, $C_1$–$C_8$haloalkyl, carboxy-$C_1$–$C_4$alkyl, $C_1$–$C_4$alkoxycarbonyl-$C_1$–$C_4$alkyl, benzyloxycarbonyl-$C_1$–$C_4$alkyl, $C_1C_4$alkylthio-$C(O)$—$C_1$–$C_4$alkyl, $C_3$–$C_5$alkenyloxycarbonyl-$C_1$–$C_4$alkyl, $C_1$–$C_4$alkylaminocarbonyl-$C_1$–$C_4$alkyl, di-$C_1$–$C_4$alkylaminocarbonyl-$C_1$–$C_4$alkyl, $C_3$–$C_5$alkenylaminocarbonyl-$C_1$–$C_4$alkyl, $C_3$–$C_8$haloalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is mono- to trisubstituted by halogen, $C_1$–$C_4$alkyl or $C_1$–$C_4$haloalkyl, or benzyl or benzyl which is mono- to trisubstituted on the phenyl ring by halogen, $C_1$–$C_4$alkyl or $C_1$–$C_4$haloalkyl, and, it $n_1$ is 0, $R_9$ is additionally hydrogen, $C_1$–$C_8$alkylcarbonyl, $R_{10}X_2C(O)$— or $R_{10}X_2C(O)$—$C_1$— or —$C_2$alkyl;

$X_2$ is oxygen, sulfur or

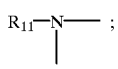

$R_{10}$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl, $C_3$–$C_8$haloalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is mono- to trisubstituted by halogen, $C_1$–$C_4$alkyl or $C_1$–$C_4$haloalkyl, or benzyl or benzyl which is mono- to trisubstituted on the phenyl ring by halogen, $C_1$–$C_4$alkyl or $C_1$–$C_4$haloalkyl;

$R_{11}$ is hydrogen, $C_1$–$C_8$alkyl or $C_3$–$C_8$alkenyl; or $R_3$ is $R_{12}R_{13}NS(O)_2$—;

$R_{12}$ is hydrogen, $C_1$–$C_8$alkyl, $C_2$–$C_8$alkenyl, $C_3$–$C_8$alkynyl or $C_3$–$C_6$cycloalkyl;

$R_{13}$ is hydrogen, $C_1$–$C_8$alkyl, $C_3$–$C_8$alkenyl, $C_3$–$C_8$alkynyl, $C_1$–$C_8$haloalkyl, $C_1$–$C_4$alkoxy-$C_1$–$C_4$alkyl, $C_1$–$C_4$alkylcarbonyl, $C_1$–$C_4$haloalkylcarbonyl, benzyl, benzoyl, or benzyl or benzoyl which are mono- to trisubstituted on the phenyl ring by halogen, $C_1$–$C_4$alkyl or $C_1$–$C_4$haloalkyl;

W is a group

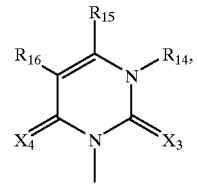 (W$_1$)

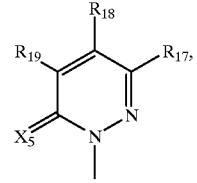 (W$_2$)

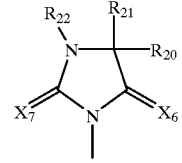 (W$_3$)

or

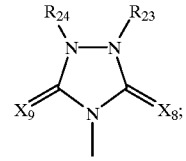 (W$_4$)

$R_{14}$ is $C_1$–$C_3$alkyl, $C_1$–$C_3$haloalkyl or amino;

$R_{15}$ is $C_1$–$C_3$haloalkyl, $C_1$–$C_3$alkyl-$S(O)_{n2}$—, $C_1$–$C_3$haloalkyl-$S(O)_{n2}$— or cyano; or $R_{15}$ and $R_{14}$ together form a $C_3$ or $C_4$alkylene bridge which can be substituted by halogen, $C_1$–$C_3$haloalkyl or cyano;

$n_2$ is 0, 1 or 2;

$R_{16}$ is hydrogen, $C_1$–$C_3$alkyl, halogen, $C_1$–$C_3$haloalkyl or cyano; or $R_{16}$ and $R_{15}$ together form a $C_3$- or $C_4$alkylene bridge which can be substituted by halogen, $C_1$–$C_3$haloalkyl or cyano;

$R_{17}$ is hydrogen, $C_1$–$C_3$alkyl, halogen or cyano;

$R_{18}$ is $C_1$–$C_3$haloalkyl; or $R_{18}$ and $R_{17}$ together form a $C_3$- or $C_4$alkylene or $C_3$- or $C_4$alkenylene bridge, both of which can be substituted by halogen, $C_1$–$C_3$alkyl or $C_1$–$C_3$haloalkyl;

$R_{19}$ is hydrogen, $C_1$–$C_3$alkyl or halogen; or $R_{19}$ and $R_{18}$ together form a $C_3$- or $C_4$alkylene or $C_3$- or $C_4$alkenylene bridge, both of which can be substituted by halogen, $C_1$–$C_3$alkyl or $C_1$–$C_3$haloalkyl;

$R_{20}$ and $R_{21}$ independently of one another are hydrogen or $C_1$–$C_4$alkyl; or $R_{20}$ and $R_{21}$ together are a group of

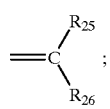

$R_{25}$ and $R_{26}$ independently of one another are $C_1$–$C_4$alkyl; or $R_{25}$ and $R_{26}$ together form a $C_4$- or $C_5$alkylene bridge;

$R_{22}$ is hydrogen or $C_1$–$C_3$alkyl; or $R_{22}$ and $R_{21}$ together form a $C_3$–$C_5$alkylene bridge which can be interrupted by oxygen and substituted by halogen, $C_1$–$C_4$alkyl, $C_1$–$C_3$haloalkyl, $C_2$–$C_4$alkenyl, $C_1$–$C_3$alkylcarbonyloxy, $C_1$–$C_3$alkoxycarbonyl, $C_1$–$C_3$alkylsulfonyloxy, hydroxyl or =O;

$R_{23}$ and $R_{24}$ independently of one another are hydrogen or $C_1$–$C_3$alkyl; or $R_{23}$ and $R_{24}$ together form a $C_2$–$C_5$alkylene bridge which can be interrupted by oxygen, sulfur, —C(O)— or —S(O)$_2$—; and $X_3$, $X_4$, $X_5$, $X_6$, $X_7$, $X_8$ and $X_9$ independently of one another are oxygen or sulfur, or an agrochemically tolerated salt or stereoisomer of such a compound of the formula I.

2. A compound of the formula I according to claim 1, in which $R_2$ is methyl, halogen, hydroxyl, nitro, amino or cyano; $R_3$ is nitro, amino, $R_4$NH, $R_4R_5$N—, azido or CIS(O)$_2$—; $R_9$, if $n_1$ is 0, is additionally hydrogen, $C_1$–$C_8$alkylcarbonyl or $R_{10}X_2$C(O)—; $R_{13}$ is hydrogen, $C_1$–$C_8$alkyl, $C_3$–$C_8$alkenyl, $C_3$–$C_8$alkynyl, $C_1$–$C_8$haloalkyl, $C_1$–$C_4$alkoxy-$C_1$–$C_4$alkyl, $C_1$–$C_4$alkylcarbonyl, $C_1$–$C_4$haloalkylcarbonyl, benzoyl or benzoyl which is mono- to trisubstituted on the phenyl ring by halogen, $C_1$–$C_4$alkyl or $C_1$–$C_4$haloalkyl.

3. A herbicidal and plant-growth-inhibitory composition which comprises a herbicidally active content of a compound of the formula I

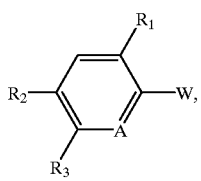

(I)

in which $R_1$, $R_2$, $R_3$, A and W have the meanings given in claim 1; and an inert carrier.

4. A herbicidal and plant-growth-inhibitory composition as claimed in claim 3 comprising, as additional component, at least one further co-herbicide.

5. A method of controlling undesirable vegetation, which comprises applying a herbicidally effective amount of an active ingredient of the formula I

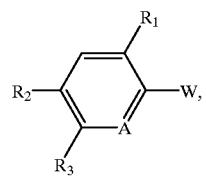

(I)

in which $R_1$, $R_2$, $R_3$, A and W have the meanings given in claim 1; or a composition comprising an active ingredient of the formula I to the plants or their environment.

6. A process for the preparation of a compound of the formula $I_a$, $I_{aa}$, $I_b$ or $I_{bb}$

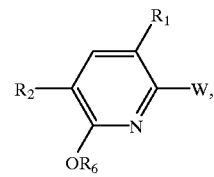

($I_a$)

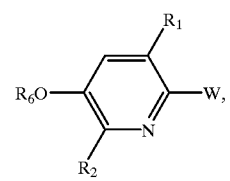

($I_{aa}$)

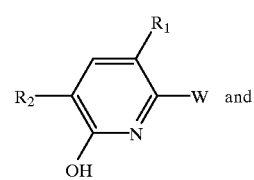

($I_b$)

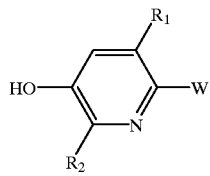

($I_{bb}$)

in which $R_1$ is hydrogen, fluorine, chlorine, bromine or methyl;

$R_2$ is $C_1$–$C_4$alkyl, $C_1$–$C_4$haloalkyl, halogen, $R_6$O—, nitro, amino or cyano;

$R_6$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl, cyano-$C_1$–$C_8$alkyl, $C_3$–$C_8$haloalkenyl, hydroxy- $C_1$–$C_4$alkyl, $C_1$–$C_4$alkoxy-$C_1$–$C_4$alkyl, $C_3$–$C_6$alkenyloxy-$C_1$–$C_4$alkyl, $C_3$–$C_6$alkynyloxy-$C_1$–$C_4$alkyl, $C_1$–$C_4$alkoxy-$C_1$–$C_4$alkoxy-$C_1$–$C_4$alkyl, $C_1$–$C_4$alkylthio-$C_1$–$C_4$alkyl, $C_1$–$C_8$alkylcarbonyl, $C_1$–$C_8$alkoxycarbonyl, $C_3$–$C_8$alkenyloxycarbonyl, benzyloxy-$C_1$- or —$C_2$akyl, benzylcarbonyl, benzyloxycarbonyl, phenyl,phenyl-$C_2$–$C_8$alkyl, benzyl, pyridyl, pyrimidinyl, pyrazinyl or pyridazinyl, it being possible for these aromatic and heteroaromatic rings to be optionally mono- to trisubstituted by halogen, $C_1$–$C_4$alkyl or $C_1$–$C_4$haloalkyl; or $R_6$ is $R_7X_1C(O)$—$C_1$–$C_8$alkyl- or

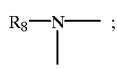

$X_1$ is oxygen, sulfur or

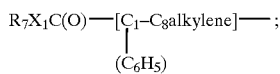

$R_7$ is hydrogen, $C_1$–$C_8$alkyl, $C_3$–$C_8$alkenyl, $C_3$–$C_8$alkynyl, $C_3$–$C_6$cycloalkyl, $C_1$–$C_6$haloalkyl, $C_3$–$C_8$haloalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is mono- to trisubstituted by halogen, $C_1$–$C_4$alkyl or $C_1$–$C_4$haloalkyl, or benzyl or benzyl which is mono- to trisubstituted on the phenyl ring by halogen, $C_1$–$C_4$alkyl or $C_1$–$C_4$haloalkyl;

$R_8$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl or benzyl; or W is a group (W$_1$)

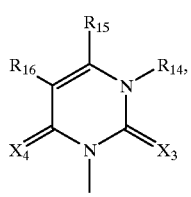

(W$_2$)

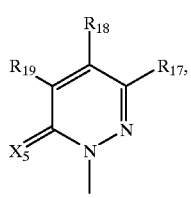

(W$_3$)

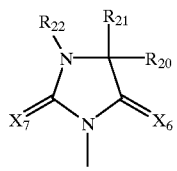

or (W$_4$)

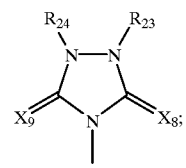

$R_{14}$ is $C_1$–$C_3$alkyl, $C_1$–$C_3$haloalkyl or amino;

$R_{15}$ is $C_1$–$C_3$haloalkyl, $C_1$–$C_3$alkyl-$S(O)_{n2}$—, $C_1$–$C_3$haloalkyl-$S(O)_{n2}$— or cyano; or $R_{15}$ and $R_{14}$ together form a $C_3$ or $C_4$alkylene bridge which can be substituted by halogen, $C_1$–$C_3$haloalkyl or cyano;

$n_2$ is 0, 1 or 2;

$R_{16}$ is hydrogen, $C_1$–$C_3$alkyl, halogen, $C_1$–$C_3$haloalkyl or cyano; or $R_{16}$ and $R_{15}$ together form a $C_3$- or $C_4$alkylene bridge which can be substituted by halogens $C_1$–$C_3$haloalkyl or cyano;

$R_{17}$ is hydrogen, $C_1$–$C_3$alkyl, halogen or cyano;

$R_{18}$ is $C_1$–$C_3$haloalkyl; or $R_{18}$ and $R_{17}$ together form a $C_3$- or $C_4$alkylene or $C_3$- or $C_4$alkenylene bridge, both of which can be substituted by halogen, $C_1$–$C_3$alkyl or $C_1$–$C_3$haloalkyl;

$R_{19}$ is hydrogen, $C_1$–$C_3$alkyl or halogen; or $R_{19}$ and $R_{18}$ together form a $C_3$- or $C_4$alkylene or $C_3$- or $C_4$alkenylene bridge, both of which can be substituted by halogen, $C_1$–$C_3$alkyl or $C_1$–$C_3$haloalkyl;

$R_{20}$ and $R_{21}$ independently of one another are hydrogen or $C_1$–$C_4$alkyl; or $R_{20}$ and $R_{21}$ together are a group of

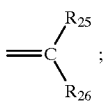

$R_{25}$ and $R_{26}$ independently of one another are $C_1$–$C_4$alkyl; or $R_{25}$ and $R_{26}$ together form a $C_4$- or $C_6$alkylene bridge;

$R_{22}$ is hydrogen or $C_1$–$C_3$alkyl; or $R_{22}$ and $R_{21}$ together form a $C_3$–$C_5$alkylene bridge which can be interrupted by oxygen and substituted by halogen, $C_1$–$C_4$alkyl, $C_1$–$C_3$haloalkyl, $C_2$–$C_4$alkenyl, $C_1$–$C_3$alkylcarbonyloxy, $C_1$–$C_3$alkoxycarbonyl, $C_1$–$C_3$alkylsulfonyloxy, hydroxyl or =O;

$R_{23}$ and $R_{24}$ independently of one another are hydrogen or $C_1$–$C_3$alkyl; or $R_{23}$ and $R_{24}$ together form a $C_2$–$C_5$alkylene bridge which can be interrupted by oxygen, sulfur, —C(O)— or —S(O)$_2$—; and $X_3$, $X_4$, $X_5$, $X_6$, $X_7$, $X_8$ and $X_9$ independently of one another are oxygen or sulfur, which comprises oxidizing a compound of the formula III

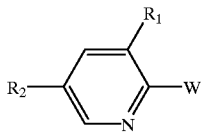
(III)

in a suitable solvent to first give the compound of the formula IV

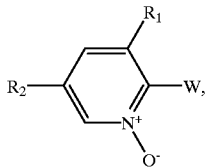
(IV)

subsequently subjecting this compound to a rearrangement in an inert solvent in the presence of an anhydride or of antimony pentachloride, which gives the compounds of the formulae $I_b$ and $I_{bb}$

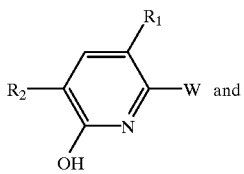
($I_b$)

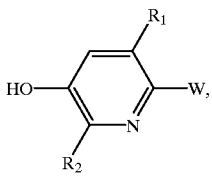
($I_{bb}$)

the radicals $R_1$, $R_2$ and W in the compounds of the formulae III, IV, $I_b$ and $I_{bb}$ having the abovementioned meanings, and converting these compounds with a compound of the formula V $R_6$—L  (V)

in which $R_6$ has the meaning given above, with the exception of $R_6$ being hydrogen, and L is a leaving group, in the presence of an inert solvent and of a base to give the isomeric compounds of the formulae $I_a$, $I_{aa}$ and II

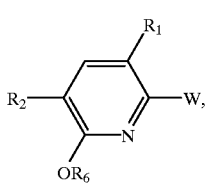
($I_a$)

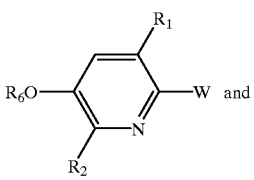
($I_{aa}$)

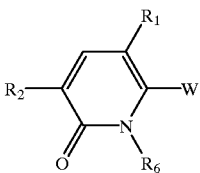
(II)

in which $R_1$, $R_2$, $R_6$ and W have the abovementioned meanings, subsequently removing the compounds of the formulae $I_a$ and $I_{aa}$ and, if appropriate, further functionalizing these compounds as defined for $R_3$ wherein $R_3$ is $R_9S(O)_{n1}$—;

$n_1$ is 0, 1 or 2;

$R_9$ is $C_1$–$C_8$alkyl, $C_3$–$C_8$alkenyl, $C_3$–$C_8$alkynyl, $C_3$–$C_6$cycloalkyl, $C_1$–$C_8$haloalkyl, carboxy-$C_1$–$C_4$alkyl, $C_1$–$C_4$alkoxycarbonyl-$C_1$–$C_4$alkyl, benzyloxycarbonyl-$C_1$–$C_4$alkyl, $C_1$–$C_4$alkylthio-C(O)—$C_1$–$C_4$alkyl, $C_3$–$C_6$alkenyloxycarbonyl-$C_1$–$C_4$alkyl, $C_1$–$C_4$alkylaminocarbonyl-$C_1$–$C_4$alkyl, di-$C_1$–$C_4$alkylaminocarbonyl-$C_1$–$C_4$alkyl, $C_3$–$C_5$alkenylaminocarbonyl-$C_1$–$C_4$alkyl, $C_3$–$C_8$haloalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is mono- to trisubstituted by halogen, $C_1$–$C_4$alkyl or $C_1$–$C_4$haloalkyl, or benzyl or benzyl which is mono- to trisubstituted on the phenyl ring by halogen, $C_1$–$C_4$alkyl or $C_1$–$C_4$haloalkyl, and, if $n_1$ is 0, $R_9$ is additionally hydrogen, $C_1$–$C_8$alkylcarbony, $R_{10}X_2C(O)$— or $R_{10}X_2C(O)$—$C_1$- or —$C_2$alkyl;

$X_2$ is oxygen, sulfur or

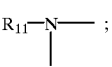

$R_{10}$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl, $C_3$–$C_8$haloalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is mono to trisubstituted by halogen, $C_1$–$C_4$alkyl or $C_1$–$C_4$haloalkyl, or benzyl or benzyl which is mono- to trisubstituted on the phenyl ring by halogen, $C_1$–$C_4$alkyl or $C_1$–$C_4$haloalkyl;

$R_{11}$ is hydrogen, $C_1$–$C_8$alkyl or $C_3$–$C_8$alkenyl; or $R_3$ is $R_{12}R_{13}NS(O)_2$—;

$R_{12}$ is hydrogen, $C_1$–$C_8$alkyl, $C_2$–$C_8$alkenyl, $C_3$–$C_8$alkynyl or $C_3$–$C_8$cycloalkyl;

$R_{13}$ is hydrogen, $C_1$–$C_8$alkyl, $C_3$–$C_6$alkenyl, $C_1$–$C_8$alkynyl, $C_1$–$C_8$haloalkyl, $C_1$–$C_4$alkoxy-$C_1$–$C_4$alkyl, $C_1$–$C_4$alkylcarbonyl, $C_1$–$C_4$haloalkylcarbonyl, benzyl, benzoyl, or benzyl or benzoyl which are mono- to trisubstituted on the phenyl ring by halogen, $C_1$–$C_4$alkyl or $C_1$–$C_4$haloalkyl.

7. A compound of the formula III

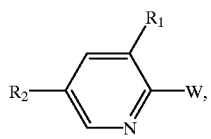
(III)

in which
R$_1$ is hydrogen, fluorine, chlorine, bromine or methyl;
R$_2$ is C$_1$–C$_4$alkyl, C$_1$–C$_4$haloalkyl, halogen, R$_6$O—, nitro, amino or cyano;
W is a group

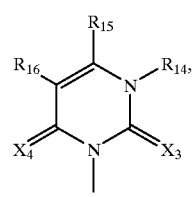
(W$_1$)

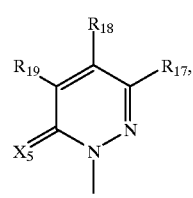
(W$_2$)

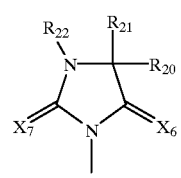
(W$_3$)

or

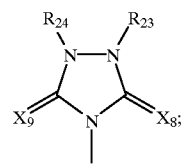
(W$_4$)

R$_{14}$ is C$_1$–C$_3$alkyl, C$_1$–C$_3$haloalkyl or amino;
R$_{15}$ is C$_1$–C$_3$haloalkyl, C$_1$–C$_3$alkyl-S(O)$_{n2}$—, C$_1$–C$_3$haloalkyl-S(O)$_{n2}$— or cyano; or
R$_{15}$ and R$_{14}$ together form a C$_3$ or C$_4$alkylene bridge which can be substituted by halogen, C$_1$–C$_3$haloalkyl or cyano;
n$_2$ is 0, 1 or 2;
R$_{16}$ is hydrogen, C$_1$–C$_3$alkyl, halogen, C$_1$–C$_3$haloalkyl or cyano; or
R$_{16}$ and R$_{15}$ together form a C$_3$- or C$_4$alkylene bridge which can be substituted by halogen, C$_1$–C$_3$haloalkyl or cyano;
R$_{17}$ is hydrogen, C$_1$–C$_3$alkyl, halogen or cyano;

R$_{18}$ is C$_1$–C$_3$haloalkyl; or
R$_{18}$ and R$_{17}$ together form a C$_3$- or C$_4$alkylene or C$_3$- or C$_4$alkenylene bridge, both of which can be substituted by halogen, C$_1$–C$_3$alkyl or C$_1$–C$_3$haloalkyl;
R$_{19}$ is hydrogen, C$_1$–C$_3$alkyl or halogen; or
R$_{19}$ and R$_{18}$ together form a C$_3$- or C$_4$alkylene or C$_3$- or C$_4$alkenylene bridge, both of which can be substituted by halogen, C$_1$–C$_3$alkyl or C$_1$–C$_3$haloalkyl;
R$_{20}$ and R$_{21}$ independently of one another are hydrogen or C$_1$–C$_4$alkyl; or
R$_{20}$ and R$_{21}$ together are a group of

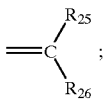
;

R$_{25}$ and R$_{26}$ independently of one another are C$_1$–C$_4$alkyl; or
R$_{25}$ and R$_{26}$ together form a C$_4$- or C$_6$alkylene bridge;
R$_{22}$ is hydrogen or C$_1$–C$_3$alkyl; or
R$_{22}$ and R$_{21}$ together form a C$_3$–C$_5$alkylene bridge which can be interrupted by oxygen and substituted by halogen, C$_1$–C$_4$alkyl, C$_1$–C$_3$haloalkyl, C$_2$–C$_4$alkenyl, C$_1$–C$_3$alkylcarbonyloxy, C$_1$–C$_3$alkoxycarbonyl, C$_1$–C$_3$alkylsulfonyloxy, hydroxyl or =O;
R$_{23}$ and R$_{24}$ independently of one another are hydrogen or C$_1$–C$_3$alkyl; or
R$_{23}$ and R$_{24}$ together form a C$_2$–C$_6$alkylene bridge which can be interrupted by oxygen, sulfur, —C(O)— or —S(O)$_2$—; and
X$_3$, X$_4$, X$_5$, X$_6$, X$_7$, X$_8$ and X$_9$ independently of one another are oxygen or sulfur.

8. A compound of the formula IV

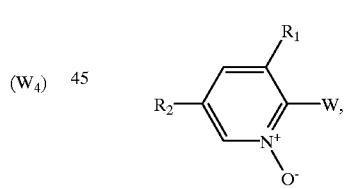
(IV)

in which
R$_1$ is hydrogen, fluorine, chlorine, bromine or methyl;
R$_2$ is C$_1$–C$_4$alkyl, C$_1$–C$_4$haloalkyl, halogen, R$_6$O—, nitro, amino or cyano;
W is a group

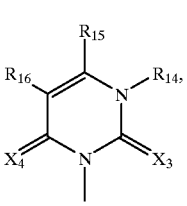
(W$_1$)

-continued

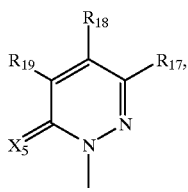
(W$_2$)

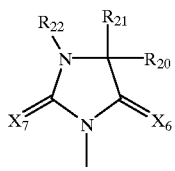
(W$_3$)

or

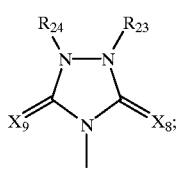
(W$_4$)

R$_{14}$ is C$_1$–C$_3$alkyl, C$_1$–C$_3$haloalkyl or amino;

R$_{15}$ is C$_{1-3}$haloalkyl, C$_1$–C$_3$alkyl-S(O)$_{n2}$—, C$_1$–C$_3$haloalkyl-S(O)$_{n2}$— or cyano;.or R$_{15}$ and R$_{14}$ together form a C$_3$ or C$_4$alkylene bridge which can be substituted by halogen, C$_1$–C$_3$haloalkyl or cyano;

n$_2$ is 0, 1 or 2;

R$_{16}$ is hydrogen, C$_1$–C$_3$alkyl, halogen, C$_1$–C$_3$haloalkyl or cyano; or R$_{16}$ and R$_{15}$ together form a C$_3$- or C$_4$alkylene bridge which can be substituted by halogen, C$_1$–C$_3$haloalkyl or cyano;

R$_{17}$ is hydrogen, C$_1$–C$_3$alkyl, halogen or cyano;

R$_{18}$ is C$_1$–C$_3$haloalkyl; or

R$_{18}$ and R$_{17}$ together form a C$_3$- or C$_4$alkylene or C$_3$- or C$_4$alkenylene bridge, both of which can be substituted by halogen, C$_1$–C$_3$alkyl or C$_1$–C$_3$haloalkyl;

R$_{19}$ is hydrogen, C$_1$–C$_3$alkyl or halogen: or

R$_{19}$ and R$_{18}$ together form a C$_3$- or C$_4$alkylene or C$_3$ or C$_4$alkenylene bridge, both of which can be substituted by halogen, C$_1$–C$_3$alkyl or C$_1$–C$_3$haloalkyl;

R$_{20}$ and R$_{21}$ independently of one another are hydrogen or C$_1$–C$_4$alkyl; or R$_{20}$ and R$_{21}$ together are a group of

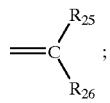

R$_{25}$ and R$_{26}$ independently of one another are C$_1$–C$_4$alkyl; or

R$_{25}$ and R$_{26}$ together form a C$_4$- or C$_5$alkylene bridge;

R$_{22}$ is hydrogen or C$_1$–C$_3$alkyl; or

R$_{22}$ and R$_{21}$ together form a C$_3$–C$_6$alkylene bridge which can be interrupted by oxygen and substituted by halogen, C$_1$–C$_4$alkyl, C$_1$–C$_3$haloalkyl, C$_2$–C$_4$alkenyl, C$_1$–C$_3$alkylcarbonyloxy, C$_1$–C$_3$alkoxycarbonyl, C$_1$–C$_3$alkylsulfonyloxy, hydroxyl or =O;

R$_{23}$ and R$_{24}$ independently of one another are hydrogen or C$_1$–C$_3$alkyl; or R$_{23}$ and R$_{24}$ together form a C$_2$–C$_5$alkylene bridge which can be interrupted by oxygen, sulfur, —C(O)— or —S(O)$_2$—: and X$_3$, X$_4$, X$_5$, X$_6$, X$_7$, X$_8$ and X$_9$ independently of one another are oxygen or sulfur.

9. A compound of the formula XVIIb

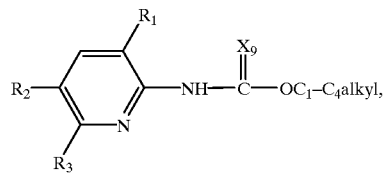
(XVIIb)

in which

R$_1$ is hydrogen, fluorine, chlorine, bromine or methyl;

R$_2$ is C$_1$–C$_4$alkyl, C$_1$–C$_4$haloalkyl, halogen, R$_6$O—, nitro, amino or cyano;

R$_3$ is halogen, nitro, amino, R$_4$NH—, R$_4$R$_5$N—, azido or ClS(O)$_2$—;

R$_4$ and R$_5$ independently of one another are C$_1$–C$_8$alkyl, C$_3$–C$_8$alkenyl, C$_3$–C$_8$alkynyl, C$_3$–C$_6$cycloalkyl, C$_1$–C$_8$haloalkyl, C$_3$–C$_8$ haloalkenyl, HCO—, C$_1$–C$_4$alkylcarbonyl, C$_1$–C$_4$haloalkylcarbonyl, C$_1$–C$_4$alkylsulfonyl, C$_1$–C$_4$haloalkylsulfonyl, benzyl or benzyl which is mono- to trisubstituted on the phenyl ring by halogen, C$_1$–C$_4$alkyl or C$_1$–C$_4$haloalkyl; or R$_4$ and R$_5$ together with the N atom to which they are bonded form a saturated or unsaturated heterocyclic ring which contains O, N or S as further hetero atoms and which can be substituted by halogen, C$_1$–C$_3$alkyl, C$_1$–C$_3$haloalkyl, C$_1$–C$_3$alkoxy, C$_1$–C$_4$alkoxycarbonyl, C$_1$–C$_3$alkylS(O)$_{n1}$—, nitro or cyano; or R$_3$ is R$_6$O—;

R$_6$ is hydrogen, C$_1$–C$_8$alkyl, C$_3$–C$_8$alkenyl, C$_3$–C$_8$alkynyl, C$_3$–C$_6$cycloalkyl, C$_1$–C$_8$haloalkyl, cyano-C$_1$–C$_8$alkyl, C$_3$–C$_8$haloalkenyl, hydroxy-C$_1$–C$_4$alkyl, C$_1$–C$_4$alkoxy-C$_1$–C$_4$alkyl, C$_3$–C$_6$alkenyloxy-C$_1$–C$_4$alkyl, C$_3$–C$_6$alkynyloxy-C$_1$–C$_4$alkyl, C$_1$–C$_4$alkoxy-C$_1$–C$_4$alkoxy-C$_1$–C$_4$alkyl, C$_1$–C$_4$alkylthio-C$_1$–C$_4$alkyl, C$_1$–C$_8$alkylcarbonyl, C$_1$–C$_8$alkoxycarbonyl, C$_3$–C$_8$alkenyloxycarbonyl, benzyloxy-C$_1$- or —C$_2$alkyl, benzylcarbonyl, benzyloxycarbonyl, phenyl,phenyl-C$_2$–C$_8$alkyl, benzyl, pyridyl, pyrimidinyl, pyrazinyl or pyridazinyl, it being possible for these aromatic and heteroaromatic rings to be optionally mono- to trisubstituted by halogen, C$_1$–C$_4$alkyl or C$_1$–C$_4$haloalkyl; or R$_6$ is R$_7$X$_1$C(O)—C$_1$–C$_8$alkyl- or R$_7$X$_1$C(O)—[C$_1$–C$_8$alkylene]—;
|
(C$_6$H$_5$)

$X_1$ is oxygen, sulfur or

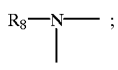 ;

$R_7$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl, $C_3$–$C_8$haloalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is mono- to trisubstituted by halogen, $C_1$–$C_4$alkyl or $C_1$–$C_4$haloalkyl, or benzyl or benzyl which is mono- to trisubstituted on the phenyl ring by halogen, $C_1$–$C_4$alkyl or $C_1$–$C_4$haloalkyl;

$R_8$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl or benzyl; or $R_3$ is hydrogen or $R_9S(O)_{n1}$—;

$n_1$ is 0, 1 or 2;

$R_9$ is $C_1$–$C_8$alkyl, $C_3$–$C_8$alkenyl, $C_3$–$C_8$alkynyl, $C_3$–$C_6$cycloalkyl, $C_1$–$C_8$haloalkyl, carboxy-$C_1$–$C_4$alkyl, $C_1$–$C_4$alkoxycarbonyl-$C_1$–$C_4$alkyl, benzyloxycarbonyl-$C_1$–$C_4$alkyl, $C_1$–$C_4$alkylthio-C(O)—$C_1$–$C_4$alkyl, $C_3$–$C_6$alkenyloxycarbonyl-$C_1$–$C_4$alkyl, $C_1$–$C_4$alkylaminocarbonyl-$C_1$–$C_4$alkyl, di-$C_1$–$C_4$alkylaminocarbonyl-$C_{-C4}$alkyl, $C_3$–$C_5$alkenylaminocarbonyl-$C_1$–$C_4$alkyl, $C_3$–$C_8$haloalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is mono- to trisubstituted by halogen, $C_1$–$C_4$alkyl or $C_1$–$C_4$haloalkyl, or benzyl or benzyl which is mono- to trisubstituted on the phenyl ring by halogen, $C_1$–$C_4$alkyl or $C_1$–$C_4$haloalkyl, and, if $n_1$ is 0, $R_9$ is additionally hydrogen, $C_1$–$C_8$alkylcarbonyl, $R_{10}X_2C(O)$— or $R_{10}X_2C(O)$—$C_1$- or —$C_2$alkyl;

$X_2$ is oxygen, sulfur or

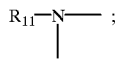 ;

$R_{10}$ is hydrogen, $C_1$–$C_8$alkyl, $C_3$–$C_8$alkenyl, $C_3$–$C_8$alkynyl, $C_3$–$C_6$cycloalkyl, $C_1$–$C_8$haloalkyl, $C_3$–$C_8$haloalkenyl, $C_1$–$C_4$alkoxy-$C_1$–$C_4$alkyl, $C_3$–$C_6$alkenyloxy-$C_1$–$C_4$alkyl, $C_1$–$C_4$alkylthio-$C_1$–$C_4$alkyl, phenyl, phenyl which is mono- to trisubstituted by halogen, $C_1$–$C_4$alkyl or $C_1$–$C_4$haloalkyl, or benzyl or benzyl which is mono- to trisubstituted on the phenyl ring by halogen, $C_1$–$C_4$alkyl or $C_1$–$C_4$haloalkyl;

$R_{11}$ is hydrogen, $C_1$–$C_8$alkyl or $C_3$–$C_8$alkenyl; or $R_3$ is $R_{12}R_{13}NS(O)_2$—;

$R_{12}$ is hydrogen, $C_1$–$C_8$alkyl, $C_2$–$C_8$alkenyl, $C_3$–$C_8$alkynyl or $C_3$–$C_6$cycloalkyl;

$R_{13}$ is hydrogen, $C_1$–$C_8$alkyl, $C_3$–$C_8$alkenyl, $C_3$–$C_8$alkynyl, $C_1$–$C_8$haloalkyl, $C_1C_4$alkoxy-$C_1$–$C_4$alkyl, $C_1$–$C_4$alkylcarbonyl, $C_1$–$C_4$haloalkylcarbonyl, benzyl, benzoyl, or benzyl or benzoyl which are mono- to trisubstituted on the phenyl ring by halogen, $C_1$–$C_4$alkyl or $C_1$–$C_4$haloalkyl; and $X_9$ is oxygen or sulfur.

* * * * *